US010668050B2

(12) United States Patent
Fathi et al.

(10) Patent No.: US 10,668,050 B2
(45) Date of Patent: *Jun. 2, 2020

(54) COMPOSITIONS, METHODS AND KITS FOR TREATING DIARRHEA-PREDOMINANT IRRITABLE BOWEL SYNDROME

(71) Applicant: RedHill Biopharma Ltd., Tel-Aviv (IL)

(72) Inventors: Reza Fathi, Oradell, NJ (US); Gilead Raday, Palo Alto, CA (US); Guy Goldberg, Tel-Aviv (IL)

(73) Assignee: RedHill Biopharma Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/606,650

(22) Filed: May 26, 2017

(65) Prior Publication Data

US 2017/0258768 A1 Sep. 14, 2017

Related U.S. Application Data

(63) Continuation of application No. 14/644,801, filed on Mar. 11, 2015, now Pat. No. 9,675,588.

(60) Provisional application No. 62/040,136, filed on Aug. 21, 2014, provisional application No. 61/951,112, filed on Mar. 11, 2014, provisional application No. 61/951,074, filed on Mar. 11, 2014, provisional application No. 61/951,092, filed on Mar. 11, 2014.

(51) Int. Cl.
| | |
|---|---|
| *A61K 31/4178* | (2006.01) |
| *A61K 9/20* | (2006.01) |
| *A61K 9/24* | (2006.01) |
| *A61K 9/28* | (2006.01) |

(52) U.S. Cl.
CPC .......... *A61K 31/4178* (2013.01); *A61K 9/209* (2013.01); *A61K 9/2013* (2013.01); *A61K 9/2054* (2013.01); *A61K 9/2886* (2013.01); *A61K 9/2077* (2013.01)

(58) Field of Classification Search
None
See application file for complete search history.

(56) References Cited

U.S. PATENT DOCUMENTS

| | | | | |
|---|---|---|---|---|
| 6,090,411 A | * | 7/2000 | Pillay | A61K 9/0065 424/468 |
| 2007/0082857 A1 | | 4/2007 | Sawa | |
| 2008/0200508 A1 | | 8/2008 | Rariy et al. | |
| 2011/0003005 A1 | * | 1/2011 | Venkatesh | A61K 9/5073 424/494 |
| 2011/0160264 A1 | | 6/2011 | Myers et al. | |

FOREIGN PATENT DOCUMENTS

| | | |
|---|---|---|
| WO | 98/41194 A1 | 9/1998 |
| WO | 2007090082 A2 | 8/2007 |
| WO | 2009118763 A1 | 10/2009 |
| WO | 2014181195 A2 | 11/2014 |

OTHER PUBLICATIONS

Garsed, K., et al., A randomized trial of ondansetron for the treatment of irritable bowel syndrome with diarrhea, Gut Online First, published on Dec. 12, 2013 as 10.1136/gutjnl-2013-305989; see Oct. 23, 2015 IDS in application 14644801.*
Haines, Elizabeth et al., "Evaluating Outcomes Associated with a Discharge Action Plan Employing Single-Dose Home Use of Ondansetron in Patients with Acute Gastroenteritis", Open Access Emergency Medicine, Mar. 1, 2012, XP55406806, 4 pages.
Maxton, D.G. et al., "Selective 5-Hydroxytryptamine Antagonism: A Role in Irritable Bowel Syndrome and Functional Dyspepsia"? Alignment Pharmacol Ther., Aug. 31, 1996, vol. 10, No. 4, pp. 595-599.
Patka, John et al., "Randomized Controlled Trial of Ondansetron vs. Prochlorperazine in Adults in the Emergency Department", Western Journal of Emergency Medicine, vol. X11, No. 1, 5 pages, (2011).
European Search Report (EP 15761030A) dated Sep. 22, 2017, 9 pages.
Al-Ansari K. et al., "Metoclopramide Versus Ondansetron for the Treatment of Vomiting in Children with Acute Gastroenteritis", J. Pediatr. Gastroenterol nutr. Aug. 2011; 53(2): 156-60.

* cited by examiner

*Primary Examiner* — H. Sarah Park
(74) *Attorney, Agent, or Firm* — Greenberg Traurig, LLP

(57) ABSTRACT

A method of treating a patient comprises orally administering a solid oral dosage form comprising a core comprising a non-ionic polymer matrix, a first amount of ondansetron dispersed within the matrix, and a salt dispersed within the matrix, wherein the first amount of ondansetron ranges from about 9 mg to about 28 mg; a first seal coat surrounding the core, wherein the first seal coat is comprised of a non-ionic polymer matrix; and an immediate release drug layer surrounding the first seal coat and comprising a non-ionic polymer and a second amount of ondansetron dispersed therein, wherein the second amount of ondansetron ranges from about 3 mg to about 8 mg, wherein release of ondansetron from the solid oral dosage form provides exposure to ondansetron for a minimum period of 16 hours so as to result in a reduction in frequency of vomiting, nausea, diarrhea, or a combination thereof.

5 Claims, 26 Drawing Sheets

COMPOSITIONS, METHODS AND KITS FOR TREATING DIARRHEA-PREDOMINANT IRRITABLE BOWEL SYNDROME

RELATED APPLICATIONS

This application is a continuation application of U.S. patent application Ser. No. 14/644,801, filed Mar. 11, 2015, which claims priority to, and the benefit of, U.S. Provisional Application No. 61/951,074, filed Mar. 11, 2014, U.S. Provisional Application No. 61/951,092, filed Mar. 11, 2014, U.S. Provisional Application No. 61/951,112, filed Mar. 11, 2014, and U.S. Provisional Application No. 62/040,136, filed Aug. 21, 2014. The contents of each of these applications are incorporated herein by reference in their entirety.

BACKGROUND

Gastroenteritis attributable to viruses or bacteria is a condition that causes irritation and inflammation of the stomach and intestines (the gastrointestinal tract). Other causes include parasites, food allergens, drug reactions to antibiotics, and ingestion of toxic plants. Vomiting caused by acute gastroenteritis is very common in children and adolescents and is a very common reason for children and adolescents attending emergency departments. Intestinal irritation caused by gastroenteritis appears to be the main stimulus for vomiting. As the virus or bacteria invades the mucosal cells of the upper gastrointestinal tract, it disrupts the normal sodium and osmotic intracellular balance and as a result excessive intracellular fluids are lost producing cellular fluid depletion.

Acute gastritis is the irritation and inflammation of the stomach's mucous lining. Gastritis may be caused by a chemical, thermal, or bacterial insult. For example, drugs such as alcohol, aspirin, and chemotherapeutic agents may cause an attack of gastritis. Likewise, hot, spicy, rough, or contaminated foods may bring about an attack. People experiencing gastritis typically vomit.

Hyperemesis gravidarumn ("HG") is a disorder in which extreme, persistent nausea and vomiting occur during pregnancy. A woman might have hyperemesis gravidarum if she is pregnant and she vomits more than three to four times per day; so much that she loses more than 10 pounds; so much that she feels dizzy and lightheaded; or so much that she is becoming dehydrated.

Vomiting, from whatever cause, occurs because of the stimulation of the two centers located in the brain, the chemoreceptor trigger zone and the vomiting center. If a person cannot drink fluids to replenish this loss, intravenous fluids may be required to put fluid back into your body (rehydration). Antiemetic medications are known to alleviate vomiting by inhibiting the body's chemoreceptor trigger zone (CTZ) or by a more direct action on the brain's vomiting center.

Irritable bowel syndrome (IBS) is a functional gastrointestinal (GI) disorder, meaning symptoms are caused by changes in how the GI tract works. IBS is a group of symptoms that occur together. The key symptom of IBS is abdominal pain and/or discomfort. The pain or discomfort is associated with a change in the frequency or consistency of stool. The altered bowel habit may be chronic or recurrent diarrhea, or constipation. Some people have both diarrhea and constipation, just at different times. Bloating or distention in the abdomen is also common. Diarrhea is one of the symptoms often associated with IBS. IBS with diarrhea is sometimes referred to as IBS-D.

SUMMARY

Ondansetron extended release solid oral dosage form for treating either nausea, vomiting, or diarrhea symptoms are disclosed herein.

According to aspects illustrated herein, a method of treating a patient comprises orally administering, to a patient, a solid oral dosage form comprising a core comprising a non-ionic polymer matrix, a first amount of ondansetron dispersed within the matrix, and a salt dispersed within the matrix, wherein the first amount of ondansetron ranges from about 9 mg to about 28 mg; a first seal coat surrounding the core, wherein the first seal coat is comprised of a non-ionic polymer matrix; and an immediate release drug layer surrounding the first seal coat and comprising a non-ionic polymer and a second amount of ondansetron dispersed therein, wherein the second amount of ondansetron ranges from about 3 mg to about 8 mg, wherein release of ondansetron from the solid oral dosage form provides exposure to ondansetron for a minimum period of 16 hours so as to result in a reduction in frequency of either vomiting, nausea, diarrhea, or a combination thereof.

Extended release solid dosage forms are disclosed herein for reducing, treating, or preventing either nausea, vomiting or diarrhea in a subject, symptoms that can be caused by a variety of conditions. In an embodiment, nausea, vomiting or diarrhea are side effects of viral gastroenteritis in a subject. In an embodiment, nausea, vomiting or diarrhea are side effects of bacterial gastroenteritis in a subject. In an embodiment, nausea, vomiting or diarrhea are side effects of gastritis (inflammation of the gastric wall) in a subject. In an embodiment, nausea, vomiting or diarrhea are side effects of inflammatory bowel disease in a subject. In an embodiment, nausea, vomiting or diarrhea are side effects of irritable bowel syndrome in a subject. In an embodiment, nausea, vomiting or diarrhea are side effects of cholecystitis in a subject. In an embodiment, nausea, vomiting or diarrhea are side effects of dyspepsia in a subject. In an embodiment, nausea, vomiting or diarrhea are side effects of pancreatitis in a subject. In an embodiment, nausea, vomiting or diarrhea are side effects of appendicitis in a subject. In an embodiment, nausea, vomiting or diarrhea are side effects of a surgical procedure in a subject. In an embodiment, nausea, vomiting or diarrhea are side effects of hepatitis in a subject. In an embodiment, nausea, vomiting or diarrhea are side effects of peritonitis in a subject. In an embodiment, nausea, vomiting or diarrhea are side effects of gastroesophageal reflux disease in a subject. In an embodiment, nausea, vomiting or diarrhea are side effects of bowel obstructive in a subject. In an embodiment, nausea, vomiting or diarrhea are side effects of food poisoning in a subject. In an embodiment, nausea, vomiting or diarrhea are side effects of a tumor in a subject.

Extended release solid dosage forms are disclosed herein. In an embodiment, extended release solid dosage forms are disclosed herein for reducing, treating, or preventing symptoms of gastroenteritis. In an embodiment, the gastroenteritis-related symptom is vomiting. To evaluate the reduction of gastroenteritis induced vomiting after administration of solid oral dosage forms of the present invention as compared with placebo, a comparison can be made between the proportion of patients without further vomiting >30 minutes after the first dose of study medication through release from the emergency department. Secondary objectives can be a comparison between the study medication groups and placebo groups of: frequency of vomiting through 4 days following first-dose of study medication; proportion of patients receiving rescue antiemetic therapy; proportion of patients receiving intravenous fluids; proportion of patients requiring hospitalization; proportion of patients returning to emergency department/urgent care department after initial discharge; time to resumption of normal activities (work/school/household); severity of nausea; and adverse event profiles.

Extended release solid dosage forms are disclosed herein. More particularly, extended release solid dosage forms are disclosed herein for treating hyperemesis gravidarum (HG). To evaluate the treatment of HG after administration of solid oral dosage forms of the present invention, severity of emesis can be measured. In an embodiment, severity of emesis is assessed, for example, by a Pregnancy Unique Quantification of Emesis (PUQE) score. The score range varies from 3 (best) to 15 (worst). In an embodiment, severity of emesis is assessed, for example, by a Visual Analogic Scale (VAS) score. The score range swings from 0 (best) to 50 (worst).

Extended release solid dosage forms are disclosed herein. More particularly, extended release solid dosage forms are disclosed herein for treating diarrhea in a subject, symptoms that can be caused by a variety of conditions. In an embodiment, diarrhea is a side effect of viral gastroenteritis in a subject. In an embodiment, diarrhea is a side effect of bacterial gastroenteritis in a subject. In an embodiment, diarrhea is a side effect of food allergies in a subject. In an embodiment, diarrhea is a side effect of premenstrual syndrome (PMS) in a subject. In an embodiment, diarrhea is a side effect of irritable bowel syndrome in a subject. In an embodiment, diarrhea is a side effect of lactose intolerancein a subject. In an embodiment, diarrhea is a side effect of parasites in a subject. In an embodiment, diarrhea is a side effect of a bacterial infection in a subject. In an embodiment, extended release solid dosage forms of the present invention are administered for treatment of Diarrhea Predominant Irritable Bowel Syndrome (IBS-D).

In an embodiment, to evaluate the reduction of vomiting after administration of solid oral dosage forms of the present invention, vomiting symptoms, such as frequency, duration, volume, severity and distress can be measured. Frequency can be measured, for example, by the number of vomiting episodes in a specified period, duration can be measured, for example, by the number of hours of vomiting), volume can be measured, for example, in cups of vomit), severity can be measured, for example, by quantifying physical symptoms, and distress that the patient is experiencing can be measured, for example, by the resulting stress and psychological symptoms).

According to aspects illustrated herein, there is disclosed an extended release ondansetron tablet that includes a core comprising a hydrophilic swellable matrix comprising ondansetron, or a pharmaceutically acceptable salt thereof, and sodium citrate anhydrous; a first seal coating comprising hypromellose and plasACRYL™; an immediate release drug layer surrounding the first seal coating comprising ondansetron, or a pharmaceutically acceptable salt thereof, hypromellose and plasACRYL™; and a second seal coating comprising hypromellose and plasACRYL™ T20, wherein the immediate release layer is sufficiently designed to release about ¼ of a total dose of ondansetron within about 1 hour after oral administration, and wherein the core is sufficiently designed to release the remaining dose of ondansetron for a period of up to 24-hours via zero-order release. In an embodiment, the core comprises about 18 mg of ondansetron free base. In an embodiment, the core comprises about 20 mg of ondansetron free base. In an embodiment, the core comprises about 28 mg of ondansetron free base. In an embodiment, the sodium citrate anhydrous is present at a concentration in the range of about 50% to about 100% by weight of the hydrophilic swellable matrix. In an embodiment, the hydrophilic swellable matrix of the core is METHOCEL™ K4M Premium CR, the hypromellose of the first seal coating and the second seal coating is METHOCEL™ E5 Premium LV, and the hypromellose of the immediate release drug layer is METHOCEL™ E5 Premium LV. In an embodiment, the immediate release layer comprises about 6 mg of ondansetron.

According to aspects illustrated herein, there is disclosed an extended release solid dosage form that includes an internal portion, wherein the internal portion comprises a first dose of at least one serotonin antagonist; a first coating, wherein the first coating directly encapsulates the internal portion of the solid dosage form; a drug layer coating, wherein the drug layer coating directly encapsulates the first coating, wherein the drug layer coating comprises a second dose of the at least one serotonin antagonist, wherein the drug layer coating is at least 4%, by weight, of the solid dosage form, wherein the second dose is equal to at least 15%, by weight, of a total dose of the at least one serotonin antagonist in the solid dosage form, and wherein the first dose is equal to the total dose minus the second dose; and a second coating, wherein the second coating directly encapsulates the drug layer coating, wherein the internal portion has solubility in water of X, wherein the first coating, the drug layer coating, and the second coating have solubility in water of at least Y, and wherein X is less than Y. In an embodiment, the at least one serotonin-3 receptor antagonist is ondansetron hydrochloride. In an embodiment, the second dose is equal to at least 20%, by weight, of the total dose of the at least one serotonin-3 receptor antagonist in the solid dosage form. In an embodiment, the at least one serotonin-3 receptor antagonist is ondansetron hydrochloride. In an embodiment, the second dose is equal to at least 25%, by weight, of the total dose of the at least one serotonin-3 receptor antagonist in the solid dosage form. In an embodiment, the first coating and the second coating comprise a hydrophilic material. In an embodiment, the drug layer further comprises a hydrophilic material. In an embodiment, the hydrophilic material is hypromellose. In an embodiment, the first coating and the second coating are each of at least 1.5%, by weight, of the solid dosage form. In an embodiment, the ratio of the hypromellose to the at least one serotonin-3 receptor antagonist in the drug layer is about 4:6. In an embodiment, a total amount of hypromellose in the first coating, the drug layer, and the second coating is less than 4%, by weight, of the solid dosage form. In an embodiment, the core further comprises sodium citrate in an amount of less than 15%, by weight, of the core. In an embodiment, X is sufficiently less than Y so that the second dose is substantially released from the solid dosage form within less than 12 hours after the solid dosage form is exposed to an aqueous environment, and the first dose is substantially released from the solid dosage in a zero-order release profile over a period of 12 to 24 hours after the solid dosage form is exposed to the aqueous environment. In an embodiment, the aqueous environment has a pH in the range of pH 1.5 to pH 7.5. In an embodiment, the solid dosage form is compressed into a tablet. In an embodiment, the solid dosage form is formed as a capsule. In an embodiment, the core further comprises glycine in an amount of less than 20%, by weight, of the core.

According to aspects illustrated herein, there is disclosed an extended release ondansetron tablet made by compressing a sustained release core tablet and then coating the core tablet with a first seal coat followed by drug coat and finally a second seal coat, wherein the core tablet comprises a hydrophilic swellable matrix comprising ondansetron hydrochloride and sodium citrate anhydrous, wherein the first seal coat comprises comprising hypromellose and plasACRYL™, wherein the drug coat comprises ondansetron hydrochloride, hypromellose and plasACRYL™, and wherein the second seal coat comprises hypromellose and plasACRYL™ T20.

According to aspects illustrated herein, there is disclosed a solid oral dosage form that includes a core comprising a non-ionic polymer matrix, a first amount of a first antiemetic drug or a pharmaceutically acceptable salt thereof dispersed within the matrix, and a salt dispersed within the matrix; a first seal coat surrounding the core, wherein the first seal coat is comprised of a non-ionic polymer matrix; and an immediate release drug layer surrounding the first seal coat, wherein the immediate release drug layer comprises a non-ionic polymer and a second amount of a second antiemetic drug or a pharmaceutically acceptable salt thereof dispersed therein, wherein the drug layer is sufficiently designed to release the second amount of the antiemetic drug over a period of at least 1 hour, wherein the solid oral dosage form is sufficiently designed to release the first amount of the first antiemetic drug and the second amount of the second antiemetic drug over a minimum period of 16 hours.

According to aspects illustrated herein, there is disclosed a solid oral dosage form that includes a core comprising hypromellose, 18 mg of ondansetron or an equivalent amount of an ondansetron salt thereof, and sodium citrate anhydrous; a first seal coat surrounding the core and comprising hypromellose; and an immediate release drug layer surrounding the first seal coat and comprising hypromellose and 6 mg of ondansetron or an equivalent amount of an ondansetron salt thereof, the immediate release drug layer sufficient to release the ondansetron over a period of at least 1 hour, wherein the total amount of ondansetron in the dosage form is released over 24 hours.

According to aspects illustrated herein, there is disclosed a solid oral dosage form that includes a core comprising a non-ionic polymer matrix, a first amount of ondansetron or an equivalent amount of an ondansetron salt thereof dispersed within the matrix, and a salt dispersed within the matrix; a first seal coat surrounding the core, wherein the first seal coat is comprised of a non-ionic polymer matrix; and an immediate release drug layer surrounding the first seal coat, wherein the immediate release drug layer comprises a non-ionic polymer and a second amount of ondansetron or an equivalent amount of an ondansetron salt thereof dispersed therein, wherein the solid oral dosage form results in an in vitro ondansetron dissolution profile when measured in a type 2 paddle dissolution apparatus at 37° C. in aqueous solution containing distilled water at 50 rpm that exhibits: a) from about 15% to 30% of the total ondansetron is released after two and a half hours of measurement in the apparatus; b) from about 30% to 50% of the total ondansetron is released after five hours of measurement in the apparatus; and c) no less than about 75% of the total ondansetron is released after fifteen hours of measurement in the apparatus.

According to aspects illustrated herein, there is disclosed a packaged pharmaceutical preparation that includes a plurality of the solid oral dosage forms of the present invention in a sealed container and instructions for administering the dosage forms orally to effect prevention of nausea and vomiting According to aspects illustrated herein, there is disclosed a pharmaceutical preparation that includes a plurality of the solid oral dosage forms of the present invention each in a discrete sealed housing, and instructions for administering the dosage forms orally to effect prevention of nausea and vomiting.

According to aspects illustrated herein, there is disclosed a packaged pharmaceutical preparation that includes a plurality of the solid oral dosage forms of the present invention in a sealed container and instructions for administering the dosage forms orally to effect treatment of diarrhea.

According to aspects illustrated herein, there is disclosed a pharmaceutical preparation that includes a plurality of the solid oral dosage forms of the present invention each in a discrete sealed housing, and instructions for administering the dosage forms orally to effect treatment of diarrhea.

According to aspects illustrated herein, there is disclosed a solid oral dosage form which reduces vomiting symptoms in a subject. According to aspects illustrated herein, there is disclosed a solid oral dosage form which reduces the need for intravenous fluids in subjects with gastroenteritis or gastritis. According to aspects illustrated herein, there is disclosed a solid oral dosage form which reduces hospital admissions in subjects with gastroenteritis or gastritis. According to aspects illustrated herein, there is disclosed a solid oral dosage form which reduces the duration of a hospital stay in subjects with gastroenteritis or gastritis.

According to aspects illustrated herein, there is disclosed a solid oral dosage form which reduces vomiting in patients with hyperemesis gravidarumn ("HG"). A method for reducing vomiting symptoms in a patient with hyperemesis gravidarumn comprises administering a therapeutically effective amount of a solid oral dosage form of the present invention to a patient once daily; and observing a reduction in vomiting symptoms. In an embodiment, the observing a reduction in vomiting symptoms includes a scoring assessment based on the PUQE score or the VAS score.

According to aspects illustrated herein, there is disclosed a solid oral dosage form which reduces diarrhea symptoms in a subject.

A method for reducing symptoms associated with gastroenteritis or gastritis in a patient comprises administering a therapeutically effective amount of a solid oral dosage form of the present invention to a patient once daily; and observing a reduction in symptoms. In an embodiment, the observing a reduction in symptoms includes monitoring the patient to quantify at least one of frequency of vomiting, whether the patient requires rescue therapy, whether the patient receives intravenous fluids, whether the patient requires hospitalization, whether the patient is admitted to an emergency department/urgent care department, time to resume normal activities, and severity of nausea.

A method for reducing symptoms associated with inflammatory bowel disease in a patient comprises administering a therapeutically effective amount of a solid oral dosage form of the present invention to a patient once daily; and observing a reduction in symptoms. In an embodiment, the observing a reduction in symptoms includes monitoring the patient to quantify at least one of frequency of vomiting, whether the patient requires rescue therapy, whether the patient receives intravenous fluids, whether the patient requires hospitalization, whether the patient is admitted to an emergency department/urgent care department, time to resume normal activities, and severity of nausea.

A method for reducing symptoms associated with irritable bowel syndrome in a patient comprises administering a therapeutically effective amount of a solid oral dosage form of the present invention to a patient once daily; and observing a reduction in symptoms. In an embodiment, the observing a reduction in symptoms includes monitoring the patient to quantify at least one of frequency of vomiting, whether the patient requires rescue therapy, whether the patient receives intravenous fluids, whether the patient requires hospitalization, whether the patient is admitted to an emergency department/urgent care department, time to resume normal activities, and severity of nausea.

A method for reducing symptoms associated with dyspepsia in a patient comprises administering a therapeutically effective amount of a solid oral dosage form of the present invention to a patient once daily; and observing a reduction in symptoms. In an embodiment, the observing a reduction in symptoms includes monitoring the patient to quantify at least one of frequency of vomiting, whether the patient requires rescue therapy, whether the patient receives intravenous fluids, whether the patient requires hospitalization, whether the patient is admitted to an emergency department/urgent care department, time to resume normal activities, and severity of nausea.

A method for reducing symptoms associated with hyperemesis gravidarumn ("HG") in a patient comprises administering a therapeutically effective amount of a solid oral dosage form of the present invention to a patient once daily; and observing a reduction in symptoms. In an embodiment, the observing a reduction in symptoms includes monitoring the patient to quantify at least one of frequency of vomiting, whether the patient requires rescue therapy, whether the patient receives intravenous fluids, whether the patient requires hospitalization, whether the patient is admitted to an emergency department/urgent care department, time to resume normal activities, and severity of nausea.

A method for reducing symptoms associated with diarrhea in a patient comprises administering a therapeutically effective amount of a solid oral dosage form of the present invention to a patient once daily; and observing a reduction in symptoms. In an embodiment, the observing a reduction in symptoms includes monitoring the patient to quantify at least one of frequency of diarrhea, severity of diarrhea and duration of diarrhea.

A method for reducing diarrhea symptoms associated with Diarrhea Predominant Irritable Bowel Syndrome (IBS-D) in a patient comprises administering a therapeutically effective amount of a solid oral dosage form of the present invention to a patient once daily; and observing a reduction in symptoms. In an embodiment, the observing a reduction in symptoms includes monitoring the patient to quantify at least one of frequency of diarrhea, severity of diarrhea, duration of diarrhea and stool consistency.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

Figure 1:
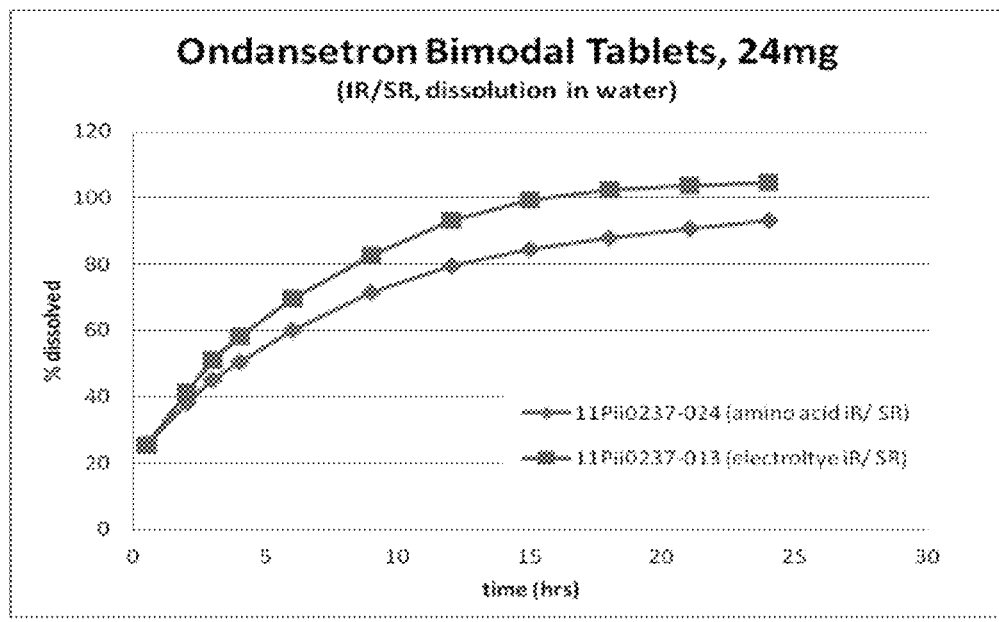
FIG. 1 illustrates the dissolution profiles of ondansetron from two embodiments of extended release solid dosage forms of the present disclosure as measured using a USP type 2 (paddle) dissolution system at 50 rpm, at a temperature of 37±0.5° with distilled water as a dissolution medium.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

As used herein the following terms have the definitions set forth below.

"Hydropathy" refers to a scale of solubility characteristics combining hydrophobicity and hydrophilicity of amino acids. More particularly this term refers to a sliding scale, similar to a pH scale, which assigns relative values which represent the relative balance between hydrophobic and hydrophilic components of an amino acid. A typical scale is set forth in Pliska et al., J. Chromatog. 216, 79, 1981, entitled Relative Hydrophobic Character of Amino Acid Side Chains, wherein glycine has a value of 0, representing a relatively equal balance between hydrophobic and hydrophilic components and may be referred to as relatively 'neutral', 'balanced', 'slightly hydrophilic'; or 'weakly hydrophobic', iso-leucine has a positive value of 1.83 and is strongly hydrophobic, and on the opposite end of the scale, aspartic acid has a negative value of −2.15 and may be characterized as strongly hydrophilic. Such a scale and the hydropathy characteristics described herein are well known and understood by those skilled in the art.

"Monolithic" refers to tablets that do not require multiple layers, special shapes, osmotic compartments and/or specialized coatings, typically without joints or seams, and are capable of being tableted on modern high speed tableting equipment.

The term "bimodal" as used herein refers to bimodal drug release profiles (fast release/slow release).

A "serotonin antagonist" or "5-HT$_3$ receptor antagonist" refers to a class of medications useful in preventing and relieving nausea and vomiting. It is believed that serotonin antagonists work by blocking the effects of the chemical serotonin, which is produced in the brain and the stomach. 5-HT$_3$ receptor antagonists efficacious in preventing and relieving nausea and vomiting include, but are not limited to, dolasetron, granisetron, ondansetron, palonosetron, tropisetron.

The term "antiemetic drug" is intended to include an antiemetic drug or a pharmaceutically acceptable salt thereof. When "ondansetron" is used, it includes the pharmaceutically acceptable salt thereof (ondansetron HCl).

Extended release solid dosage forms are provided. More particularly, the present disclosure relates to extended release bimodal solid dosage forms for the reduction of gastroenteritis induced vomiting. "Reduction of gastroenteritis induced vomiting" can be measured by monitoring the frequency (as measured, for example, by the number of vomiting episodes in a specified period), the duration (as measured, for example, by the number of hours of vomiting), the volume (as measured, for example, in cups of vomit), the severity (as measured, for example, by quantifying physical symptoms) and/or the distress the patient is experiencing (as measured, for example, by the resulting stress and psychological symptoms). In an embodiment, an extended release solid dosage form includes an internal portion, wherein the internal portion comprises a first dose of ondansetron; a first coating, wherein the first coating directly encapsulates the internal portion of the solid dosage form; a drug layer coating, wherein the drug layer coating directly encapsulates the first coating, wherein the drug layer coating comprises a second dose of ondansetron, wherein the drug layer coating is at least 4%, by weight, of the solid dosage form, wherein the second dose is equal to at least 15%, by weight, of a total dose of the ondansetron in the solid dosage form, and wherein the first dose is equal to the total dose minus the second dose; and a second coating, wherein the second coating directly encapsulates the drug layer coating, wherein the internal portion has solubility in water of X, wherein the first coating, the drug layer coating, and the second coating have solubility in water of at least Y, and wherein X is less than Y. In an embodiment, the extended release solid dosage form is capable of producing a burst of approximately 25% ondansetron, followed by a zero-order release of the remaining ondansetron over a period of between 16-20 hours. In an embodiment, the extended release solid dosage form is capable of producing a burst of approximately 25% ondansetron, followed by a zero-order release of the remaining ondansetron over a period of between 20-30 hours.

Ondansetron

Ondansetron is an effective anti-vomiting agent. Ondansetron displays central and/or peripheral action by preferentially blocking the serotonin 5-$HT_3$ receptors. Ondansetron hydrochloride (HCl) is the dihydrate, the racemic form of ondansetron. Ondansetron has the empirical formula C18H19N3O.HCl.2H2O, representing a molecular weight of 365.9. Ondansetron HCl dihydrate is a white to off-white powder that is soluble in water and normal saline.

Internal Portion ("Core") of Solid Dosage Forms of an Embodiment of the Present Disclosure As a tablet passes through the human digestive tract, it is subjected to pH values ranging from about 1.5 to about 7.4. The saliva of the mouth has a neutral pH, the stomach has a pH varying from about 1.5-4.0, and the pH of the intestines carries a pH between about 5.0-7.5. For a drug to approach zero-order release, the drug's dissolution must be independent of the pH in the surrounding environment. The internal portion ("core") of a dosage form of the present disclosure may approach zero order delivery of a drug.

Internal Portion—Electrolyte Platform

In an embodiment, the internal portion ("core") is comprised of a hydrophilic swellable matrix, in which is disposed a pharmaceutically active agent ("API") and one or more electrolytes. The "electrolyte core" is a slow release ("SR") formulation. The one or more electrolytes, either in combination with the API or another salt upon reaction in an aqueous medium, causes a hardening reaction of the matrix. The rate of outward diffusion is controlled by exposing the internal portion to an aqueous medium. This in turn causes a hardening reaction to occur in a time dependent manner from the outer boundaries towards the inner boundaries of the internal portion; the hardened reaction product, in turn limits outward diffusion of the API as the inward ingress of aqueous medium causes a progressive hardening from the outer boundaries of the internal portion in a direction towards the inner core there.

The internal portion employs the colloidal chemistry phenomenon of "salting-out" to moderate the swelling and erosion kinetics of a non-ionic polymer matrix containing the API and one or more electrolytes. The presence of these electrolytic compounds in the form of ionizable salts allows for non-collapsible diffusion channels to form; channelization agents used in the past were not ionizable, therefore, the diffusion channels were unpredictable leading to poor release profiles and lack of control. The electrolytes also contribute to a contracting micro-environment within the tablet, whose pH is mediated by the pKa of the electrolyte, thus either enhancing or suppressing the solubility of the API itself. As the matrix hydrates, the electrolytes and polymer compete for water of hydration with the API, resulting in a programmable rate of release. The internal portion is thus capable of zero-order, pH-independent release of an API for up to 24-hours, without regard to the solubility of the API itself.

Through processes of ionic interaction/complexation/molecular and/or self association between a drug and an electrolyte or electrolyte/drug combinations, homogeneously dispersed in a swellable polymer such as hydroxypropylmethylcellulose (HPMC), modify the dynamics of the matrix swelling rate and erosion of the swellable polymer, in accordance with variations in an external pH environment ranging from about 1.5-7.0. These interactions result in controlled matrix hardening. Such hardening is responsible for the control of polymer erosion/dissolution and drug release rates. By design, solvent penetrates the periphery of the tablet and a rapid initial interaction between drug and electrolyte embedded in the polymeric matrix causes immediate hardening of the outer tablet boundary, the rate of hardening consistently decreases toward the center of the matrix core in a time-dependent manner over a long period of time (e.g. 24 hours).

The differential rate of matrix hardening is the driving principle in the internal portion, which is dependent on and controlled by the rate of liquid ingress to the internal portion core. With the simultaneous time-dependent decrease in gel layer integrity, the rate of drug diffusion decreases. This phenomenon compensates for the increase in diffusion path length and decrease in the surface area of the receding core which arises from the swelling property of the polymer. Hence, better controlled, preferably zero order, drug release is achieved. The drug release process can be tailored for up to 24 hours. Control of the changes in core hardness and synchronization of the rubbery/swelling front and described receding phase boundaries as well as erosion of the dissolution front boundary (i.e. erosion of the tablet periphery) results in controlled drug release, preferably including zero order kinetics. Optionally, polymer matrix hardenings is also easily achievable through double salt interaction. This binary salt combination is also uniformly dispersed in the polymeric matrix, which through ionic interaction/complexation/molecular and/or self association, increases the relative strength and rigidity of the matrix, resulting in controlled drug release with a similar mechanism to that described above.

One hydrophilic matrix material useful in the internal portion is HPMC K4M. This is a nonionic swellable hydrophillic polymer manufactured by "The Dow Chemical Company" under the tradename "Methocel". HPMC K4M is also abbreviated as HPMC K4MP, in which the "P" refers to premium cellulose ether designed for controlled release formulations. The "4" in the abbreviation suggests that the polymer has a nominal viscosity (2% in water) of 4000. The percent of methoxyl and hydroxypropryl groups are 19-24 and 7-12, respectively. In its physical form, HPMC K4M is a free-flowing, off-white powder with a particle size limitation of 90%<100 mesh screen. There are other types of HPMC such as K100LVP, K15MP, K100MP, E4MP and E10MP CR with nominal viscosities of 100, 1500, 100000, 4000, and 10000 respectively.

Because the internal portion consists of a non-covalently bonded matrix, the manufacturing process is a fundamentally two-step process of dry-blending and direct compression.

In an embodiment, a salt is dispersed in the matrix at a concentration in the range of about 50% to about 100% by weight of the polymeric matrix. In an embodiment, the salt is selected from one or two members of the group consisting of sodium chloride, sodium bicarbonate, potassium bicarbonate, sodium citrate, sodium bisulfate, sodium sulfite, magnesium sulfate, calcium chloride, potassium chloride, and sodium carbonate.

It is believed that an interaction between drug and salt forms a complex in the surrounding swellable matrix in a layered fashion because it occurs in a time-dependent manner as the solvent media for drug release penetrates the tablet inwardly. Likewise, because the catalyst for the initiation of drug release is liquid ingress, so too is the rate of drug release controlled by the inwardly progressive hardening of the salt complex.

A binary salt system (e.g. calcium chloride and sodium carbonate) may also be used in which case the hardening reaction may be a function of interaction between the salts. Calcium chloride may be incorporated to form a complex with sodium carbonate. With this combination, the reaction products are insoluble calcium carbonate and soluble channel former, sodium chloride. Hence the calcium carbonate embeds itself in the polymer matrix, initiates hardening and slowly dissolves with liquid ingress and the subsequent creation of diffusion channels as drug diffuses out. In a similar way, other binary salt combinations display time-dependent "hardening/de-hardening" behavior.

The amount of salt to be used may be determined taking into consideration the solubility of the drug, the nature of the polymer and the required degree of matrix hardening desired. In case of diltiazem hydrochloride in a HPMC matrix, 100 mg of sodium bicarbonate provides suitable matrix hardening for zero order controlled release, while in the case of the same amount of drug in a different polymer such as polyethylene oxide, 50 mg of sodium bicarbonate appears to be ideal for the attainment of controlled zero order release.

The pharmaceutically active ingredient can be selected from the group consisting of Aprepitant (Emend), Dexamethasone, Dolasetron (Anzemet), Dronabinol (Marinol), Droperidol (Insapsine), Granisetron (Kytril), Haloperidol (Haldol), Methylprednisolone (Medrol), Metoclopramide (Reglan), Nabilone (Cesamet), Ondansetron (Zofran), Palonosetron (Aloxi), Prochlorperazine (Procomp), and pharmaceutically acceptable salts thereof, or combinations thereof.

In an embodiment, the internal portion of a solid dosage form of the present disclosure is a hydrophilic swellable polymeric matrix having dispersed within the matrix a pharmaceutically effective amount of at least one serotonin antagonist whose degree of solubilization is substantially independent of pH over a pH in the range of pH 1.5 to pH 7 0.5 and an inorganic salt, wherein the inorganic salt is present at a concentration in the range of 50% to 100% by weight of the polymeric matrix. In an embodiment, the inorganic salt is sodium citrate. In an embodiment, the hydrophilic swellable polymeric matrix is hydroxypropylmethylcellulose or polyethylene oxide.

An internal portion as described above can be prepared by a process as disclosed in U.S. Pat. No. 6,090,411, which is incorporated herein by reference for the teachings disclosed therein.

Internal Portion—Amino Acid Platform

In an embodiment, the internal portion ("core") is comprised of a hydrophilic extragranular polymer in which is dispersed a plurality of granules of an API, granulated with at least one amino acid, and an intragranular polymer. The "amino acid core" or "AA core" is a slow release ("SR") formulation. The granules are dispersed within a hydrophilic extragranular polymer to form a monolithic matrix. The extragranular polymer more rapidly hydrates relative to the intragranular polymer. The rapid hydration of the extragranular polymer assists in the approximation of a linear release profile of the drug and facilitates near 100% dissolution, while extending the duration of release and reducing the burst effect frequently encountered with extended release dosage forms. Linear release rate can be tailored to fit the needs of each application by selecting polymers for different dissolution rates. In an embodiment, a release time of 12 to 24 hours is achieved.

The intragranular polymer is combined with an API, and at least one amino acid to form granules. The intragranular polymer may be one or more of the following: polyvinyl acetate, a galactomannan polysaccharide such as hydroxypropyl guar, guar gum, locust bean gum, pectin, gum acacia, gum tragacanth, karaya gum, cellulose ethers such as hydroxyproplymethyl cellulose (HPMC), as well as other gums and cellulose ethers to be chosen by one of skill in the art for properties consistent with the teaching of this invention. In an embodiment, the intragranular polymer is a galactomannan polysaccharide, guar gum (with a viscosity range of 75-6000 cps for a 1% solution at 25° C. in water and a particle size 10-300 µm).

The intragranular polymer in the internal portion is present in amounts between 4% and 45% of the total dosage form weight. The specific type of intragranular polymer and amount of intragranular polymer used is chosen depending on the desired rate of drug release, viscosity of the polymer, the desired drug load, and the drug solubility. The intragranular polymer hydrates less rapidly than the extragranular polymer. The relative difference in hydration rates between the two polymers creates a less viscous intragranular polymer and a more viscous extragranular polymer. Over time, the difference in viscosity contributes to the continuous erosion and disintegration of the solid dosage form.

Amino acids are useful in this embodiment for two primary reasons. First, the amino acids are a factor in determining the viscosity of the polymers. As noted above, over time the difference in viscosity between the extragranular and intragranular polymers contributes to the continuous erosion and disintegration of the core, facilitating about 100% release of the drug. Another important aspect of using an amino acid in the granule is that the hydropathy of the amino acid may be exploited to modulate the solubility and release of a drug.

Thus, the amino acid is selected for hydropathy characteristics depending on the solubility characteristics of the active compound. When the compound is at least sparingly water soluble, that is, for example, sparingly soluble, soluble or has a higher level of solubility, as defined by the United States Pharmacopeia, an amino acid is utilized which has a relatively equal balance between hydrophilic and hydrophobic components, i.e. is neutral or balanced or within close proximity to neutrality, or is relatively more strongly hydrophilic.

For example, dissolution and release of soluble or sparingly soluble ionizable drugs such as verapamil HCl can be controlled by the inclusion of one or more amino acids in the granules. Without subscribing to a particular theory of drug release and dissolution, it is believed that the nature of the granulation process is such that as the formulation components come into close molecular contact, granulation reduces the available surface area of the particles, thus reducing the initial rate of hydration. In the granulated formulations, there is sufficient time for the amino acid carboxyl (COOH—) groups and amino groups ($NH_2/NH_{3+}$) to interact with hydroxyl groups on the polymer, thus mediating the swelling, viscosity, and gel properties of the polymer and thereby exerting control on the swelling mediated drug diffusion. Simultaneously, the amino acid carboxyl groups may also interact with suitable polar substituents on the drug molecule such as secondary or tertiary amines. Furthermore, the hydrophilic and ionic nature of amino acids results in their extensive hydration in aqueous solution. Consequently, the amino acid promotes erosion, but also competes with both the polymer and the drug for water uptake necessary for hydration and dissolution.

However, when the active compound is less than sparingly soluble, including active compounds which are slightly soluble to insoluble, a combination of at least two amino acids is utilized, one of which is strongly hydrophobic, the other of which is relatively more hydrophilic than the hydrophobic component, that is, about neutral or balanced to strongly hydrophilic.

The amino acid component of the granules may comprise any pharmaceutically acceptable α-amino or β-amino acids, salts of α- or β-amino acids, or any combination thereof. Examples of suitable α-amino acids are glycine, alanine, valine, leucine, iso-leucine, phenylalanine, proline, aspartic acid, glutamic acid, lysine, arginine, histidine, serine, threonine, cysteine, asparagine, and glutamine. An example of a β-amino acid is β-alanine.

The type of amino acids used in this embodiment of the internal portion can be described as hydrophilic, hydrophobic, salts of hydrophilic or hydrophobic amino acids, or any combination thereof. Suitable hydrophobic amino acids for use include, but are not limited to, iso-leucine, phenylalanine, leucine, and valine. Further, hydrophilic amino acids, such as glycine, aspartate and glutamate can be used in the granule. Ultimately, any amino acid, and any amino acid in combination with another amino acid, can be employed in the present invention to enhance the solubility of a drug. For a detailed list of amino acids that can be used in the present invention and the hydropathy of each, see Albert L. Lehninger et al., Principles of Biochemistry 113 (2nd ed. Worth Publishers 1993).

The type and amount of amino acid may be chosen depending on the desired drug load, desired rate of drug release, and the solubility of the drug. The amino acid in the dosage form is typically between 4% and 45% of the total dosage form weight. In an embodiment, the amount of amino acid is between 11% and 29% by weight of the total dosage form.

The granules may optionally be blended with a coating material, for example magnesium stearate or other hydrophobic derivatives of stearic acid. The amount of coating material used can vary from 1% to 3% of the total weight of the dosage form. Normally, magnesium stearate is used to facilitate processing, for example as a flow aid, but in the present invention magnesium stearate has the additional benefit of retarding dissolution, due to the hydrophobic nature of the coating material. Therefore, magnesium stearate can be used to further adjust the solubility of the dosage form and further retard drug release from the granules.

To enhance the mechanical properties and/or to influence the drug release rate further, the granules may also contain small amounts of inert pharmaceutical fillers and binders/granulating agents as is conventional to the art. Examples of inert pharmaceutical fillers include: lactose, sucrose, maltose, maltodextrins, dextrins, starch, microcrystalline cellulose, fructose, sorbitol, di- and tri-calcium phosphate. Examples of granulating agents/binders include starch, methylcellulose, hydroxy propyl- or hydroxypropylmethyl cellulose, sodium carboxymethyl cellulose, or poly-vinyl pyrrolidone, gum accacia tragacanth and sucrose. Other suitable fillers may also be employed as understood by one of skill in the art. Depending on the physical and/or chemical properties of the drug, a wet granulation procedure (using either an aqueous or organic granulating fluid) or a dry granulation procedure (e.g. slugging or roller compaction) can be employed.

After the granulation of the pharmaceutically active compound, intragranular polymer, amino acids, and optionally fillers and hydrophobic coating materials, the granule is then blended with and dispersed within an extragranular polymer.

The extragranular polymer may be one or more of the following: polyethylene oxide, a galactomannan polysaccharide such as hydroxypropyl guar, guar gum, locust bean gum, pectin, gum accacia, gum tragacanth, karaya gum, cellulose ethers such as hydroxypropylmethyl cellulose (HPMC), as well as other gums and cellulose ethers to be chosen by one of skill in the art for properties consistent with the teaching of this invention. The extragranular polymer may be a galactomannan polysaccharide such as guar gum (with a viscosity range of 75-6000 cps for a 1% solution at 25° C. in water and a particle size 10-300 μm). As noted above, the extragranular polymer should hydrate rapidly and achieve a high level of viscosity in a shorter period of time relative to the intragranular polymer.

The difference in hydration rates between the extragranular polymer and intragranular polymer is achieved by three principle means, (1) by choosing polymers based on differences in particle size, (2) by choosing polymers based on differences in molecular weight and chemical composition and (3) by choosing polymers based on a combination of (1) and (2). Although this disclosure focuses primarily on polymers chosen for differences in particle size, it is possible to achieve the results of this invention by using an intragranular polymer with a different molecular weight and/or chemical composition than the extragranular polymer. For example, polyethylene oxide may be used as the intragranular polymer and guar gum as the extragranular polymer.

Particle size is another characteristic of commercial guar gum because coarser particles ensure rapid dispersion, while finer particles are ideal for fast hydration. Therefore, in order to achieve the desired result of the present invention. In an embodiment, the finer particles are used for the extragranular polymer and less fine particles are used for the intragranular polymer particles. The brochure by HERCULES Incorporated, entitled "Supercol® Guar Gum, 1997" contains the typical properties of guar gum of different grades and particles sizes. Other rapidly hydrating extragranular polymers which may be used include: polyethylene oxide (PEO), cellulose ethers and polysaccharides such as hydroxypropyl guar, pectin, gum accacia and tragacanth, karaya gum, mixtures of the aforementioned polymers and any other polymers to be chosen by one of skill in the art for properties consistent with the teaching of this invention. The amounts and the types of extragranular polymer are chosen depending on the desired drug load, rate of drug release and drug solubility. A range of about 4-47% (by total tablet weight) of extragranular polymer has been found to be feasible. In an embodiment, a range of extragranular polymer is from about 15% to about 47% (by total tablet weight).

A therapeutic amount of an API, for example up to about 75% of the total dosage form weight, can be included in the internal portion. With this drug load, the internal portion approximates a linear release profile, with a minimal, or elimination of, burst effect. However, if desired by a skilled artisan, the extragranular polymer may contain additional amounts of the pharmaceutically active compound to achieve more rapid drug release or an induced burst effect, as well as contain amino acids to mediate dissolution of the pharmaceutically active compound, as described above.

The tableted oral extended release dosage form optionally may be coated with polymers, plasticizers, opacifiers, and colourants as is conventional in the art.

In an embodiment, the internal portion of a solid dosage form of the present disclosure is (1) a plurality of granules comprising (a) at least one serotonin antagonist; (b) at least one amino acid; and (c) an intragranular polymer; the intragranular polymer comprising 4% to 45% of the total dosage form by weight and, (2) a hydrophilic extragranular polymer in which the granules are dispersed, the extragranular polymer comprising 4% to 47% of the total dosage form by weight and being more rapidly hydrating than the intragranular polymer, wherein the amino acid is selected for hydropathy characteristics depending on solubility characteristics of the at least one serotonin antagonist and comprises 11% to 29% of the total dosage form by weight. In an embodiment, when the at least one serotonin antagonist is at least sparingly soluble in water, the amino acid has a relatively equal balance between hydrophobic and hydrophilic components or is relatively more hydrophilic In an embodiment, when the at least one serotonin antagonist is less than sparingly soluble in water, the amino acid is a combination of at least two amino acids, one of which is moderately or strongly hydrophobic, the other of which is relatively more hydrophilic. In an embodiment, the intragranular polymer comprises at least one of the following: polyvinyl acetate, a galactomannan polysaccharide selected from the group consisting of hydroxypropyl guar, guar gum, locust bean gum, pectin, gum accacia, tragacanth, karaya gum, or cellulose ethers. In an embodiment, the amino acid is selected from the group consisting of: a) α-amino acids b) β-amino acids c) a combination of α- and β-amino acids. In an embodiment, the α-amino acid is at least one member selected from the group consisting of glycine, alanine, valine, leucine, iso-leucine, phenylalanine, proline, aspartic acid, glutamic acid, lysine, arginine, histidine, serine, threonine, cysteine, asparagine and glutamine. In an embodiment, the combination of α and β amino acids comprises β-alanine and at least one α-amino acid selected from the group consisting of glycine, alanine, valine, leucine, iso-leucine, phenylalanine, proline, aspartic acid, glutamic acid, lysine, arginine, histidine, serine, threonine, cysteine, asparagine, and glutamine. In an embodiment, the amino acid is selected from the group consisting of: a) a balanced amino acid having a relatively equal balance between hydrophobic and hydrophilic components or a relatively more hydrophilic amino acid, or b) a combination of (i) a balanced amino acid or a relatively more hydrophilic amino acid and (ii) a hydrophobic amino acid. In an embodiment, the balanced amino acid comprises glycine. In an embodiment, the internal portion comprises glycine and a hydrophobic amino acid selected from iso-leucine, valine, and phenylalanine. In an embodiment, the plurality of granules are blended with a hydrophobic coating material. In an embodiment, the hydrophobic coating material is magnesium stearate. In an embodiment, the hydrophobic coating material is 1% to 3% of the total dosage form weight.

An internal portion as described above can be prepared by a process as disclosed in U.S. Pat. No. 6,517,868, which is incorporated herein by reference for the teachings disclosed therein.

First and Second Coatings

The first coating and the second coating of an extended release bimodal solid dosage form of the present disclosure are non-functional coatings that act as processing aids. The first coating and the second coating do not substantially affect the release of the API from the dosage form. In an embodiment, the first and the second coating comprise a hydrophilic material. In an embodiment, the hydrophilic material is hypromellose. In an embodiment, the hypromellose is Methocel E5. In an embodiment, the first and the second coating further comprise the coating additive plasACRYL™, an aqueous emulsion of glyceryl monostearate and triethyl citrate (developed by Emerson Resources, Inc. of Norristown, Pa., USA). In an embodiment, the plasACRYL™ used in the first and second coatings is T20 grade. In an embodiment, the PlasACRYL™ T20 is a 20% aqueous suspension, containing an anti-tacking agent, a plasticizer and a stabilizer. Hypromellose is a pH independent non-ionic polymer formed by partial substitution with O-methylated and O-(2-hydroxypropylated) groups. The grades of hypromellose can vary upon extent to substitution which affects the viscosity. HPMC K4M Premium exhibits a viscosity of 3550 mPas, while HPMC E5 premium LV is a low viscosity grade polymer having a viscosity of 5 mPas. Hypromellose is soluble in cold water and forms a colloidal viscous liquid.

Drug Layer Overcoat

The drug layer overcoat of an extended release solid dosage form of the present disclosure is an immediate release ("IR") drug layer. In an embodiment, the drug layer overcoat is sufficiently designed to yield a burst of about 25% API, which, when the solid dosage form is ingested orally, would result in about 25% API being released in the stomach. In an embodiment, the drug layer overcoat, or immediate release drug layer, comprises ondansetron hydrochloride, hypromellose and plasACRYL™. In an embodiment, the hypromellose used in the IR layer is Methocel E5.

Additional Layers—Enteric Coating

In an embodiment, an extended release solid dosage form of the present disclosure further includes an enteric coating. In an embodiment, an enteric coating layer is positioned between the first coating and the drug layer overcoat. In an embodiment, the enteric coating layer is EUDRAGIT® L30D-55. In an embodiment, the enteric coating layer is EUDRAGIT® FS 30 D. In an embodiment, the enteric coating layer is SURETERIC®.

Solid Oral Dosage Forms of the Present Disclosure

In an embodiment, a solid oral dosage form of the present disclosure includes a total of 24 mg of ondansetron (or an equivalent amount of ondansetron HCL). In an embodiment, 18 mg of ondansetron are present in the core of the dosage form and 6 mg of ondansetron are present in the drug overcoat.

In an embodiment, a solid oral dosage form of the present disclosure includes a total of 12 mg of ondansetron (or an equivalent amount of ondansetron HCL). In an embodiment, 9 mg of ondansetron are present in the core of the dosage form and 3 mg of ondansetron are present in the drug overcoat.

In an embodiment, a solid oral dosage form of the present disclosure includes a total of 28 mg of ondansetron (or an equivalent amount of ondansetron HCL). In an embodiment, 20 mg of ondansetron are present in the core of the dosage form and 8 mg of ondansetron are present in the drug overcoat.

In an embodiment, a solid oral dosage form of the present disclosure includes a total of 36 mg of ondansetron (or an equivalent amount of ondansetron HCL). In an embodiment, 28 mg of ondansetron are present in the core of the dosage form and 8 mg of ondansetron are present in the drug overcoat.

Dosing Regimen

In an embodiment, a solid oral dosage form of the present disclosure including a total of 24 mg of ondansetron (as an equivalent amount of ondansetron HCl) is administered to an adult or a child (≥age 12) experiencing acute gastroenteritis to provide rapid relief of symptoms and maintaining relief without need for redosing over the course of the illness, which is usually approximately one day. Release of ondansetron from the solid oral dosage form provides exposure to ondansetron for a minimum period of 16 hours so as to result in a reduction in frequency of either vomiting, nausea, or diarrhea in the patient.

In an embodiment, a solid oral dosage form of the present disclosure including a total of 12 mg of ondansetron (as an equivalent amount of ondansetron HCl) is administered to a child (<age 12) experiencing acute gastroenteritis to provide rapid relief of symptoms and maintaining relief without need for redosing over the course of the illness, which is usually approximately one day. Release of ondansetron from the solid oral dosage form provides exposure to ondansetron for a minimum period of 16 hours so as to result in a reduction in frequency of either vomiting, nausea, or diarrhea in the patient.

In an embodiment, a solid oral dosage form of the present disclosure including a total of 24 mg of ondansetron (as an equivalent amount of ondansetron HCl) is administered to an adult or a child (≥age 12) experiencing prolonged gastroenteritis to provide rapid relief of symptoms and maintaining relief. Redosing over the course of the illness, once daily, may be necessary. Release of ondansetron from the solid oral dosage form provides exposure to ondansetron for a minimum period of 16 hours so as to result in a reduction in frequency of either vomiting, nausea, or diarrhea in the patient.

In an embodiment, a solid oral dosage form of the present disclosure including a total of 12 mg of ondansetron (as an equivalent amount of ondansetron HCl HCL) is administered to a child (<age 12) experiencing prolonged gastroenteritis to provide rapid relief of symptoms and maintaining relief. Redosing over the course of the illness may be necessary. Release of ondansetron from the solid oral dosage form provides exposure to ondansetron for a minimum period of 16 hours so as to result in a reduction in frequency of either vomiting, nausea, or diarrhea in the patient.

In an embodiment, a solid oral dosage form of the present disclosure including a total of 28 mg of ondansetron (as an equivalent amount of ondansetron HCl) is administered to an adult or a child (≥age 12) experiencing prolonged gastroenteritis to provide rapid relief of symptoms and maintaining relief. Redosing over the course of the illness may be necessary. Release of ondansetron from the solid oral dosage form provides exposure to ondansetron for a minimum period of 16 hours so as to result in a reduction in frequency of either vomiting, nausea, or diarrhea in the patient.

In an embodiment, a solid oral dosage form of the present disclosure including a total of 36 mg of ondansetron (as an equivalent amount of ondansetron HCl) is administered to an adult or a child (≥age 12) experiencing prolonged gastroenteritis to provide rapid relief of symptoms and maintaining relief. Redosing over the course of the illness may be necessary. Release of ondansetron from the solid oral dosage form provides exposure to ondansetron for a minimum period of 16 hours so as to result in a reduction in frequency of either vomiting, nausea, or diarrhea in the patient.

In an embodiment, a solid oral dosage form of the present disclosure including a total of 12 mg of ondansetron (as an equivalent amount of ondansetron HCl). The dosage form is cut in half, and is administered to a child age 4-12, experiencing prolonged gastroenteritis to provide rapid relief of symptoms and maintaining relief. Redosing over the course of the illness, for example every 8 hours, may be necessary. Release of ondansetron from the solid oral dosage form provides exposure to ondansetron for a minimum period of 16 hours so as to result in a reduction in frequency of either vomiting, nausea, or diarrhea in the patient.

In an embodiment, a solid oral dosage form of the present disclosure including a total of 24 mg of ondansetron (as an equivalent amount of ondansetron HCl HCL) is administered to a pregnant female patient experiencing hyperemesis gravidarum to provide rapid relief of symptoms and maintaining relief. Redosing over the course of the illness may be necessary.

Release of ondansetron from the solid oral dosage form provides exposure to ondansetron for a minimum period of 16 hours so as to result in a reduction in frequency of either vomiting, nausea, or diarrhea in the patient.

In an embodiment, a solid oral dosage form of the present disclosure including a total of 28 mg of ondansetron (as an equivalent amount of ondansetron HCl HCL) is administered to a pregnant female patient experiencing hyperemesis gravidarum to provide rapid relief of symptoms and maintaining relief. Redosing over the course of the illness may be necessary. Release of ondansetron from the solid oral dosage form provides exposure to ondansetron for a minimum period of 16 hours so as to result in a reduction in frequency of either vomiting, nausea, or diarrhea in the patient.

In an embodiment, a solid oral dosage form of the present disclosure including a total of 36 mg of ondansetron (as an equivalent amount of ondansetron HCl) is administered to a pregnant female patient experiencing hyperemesis gravidarum to provide rapid relief of symptoms and maintaining relief. Redosing over the course of the illness may be necessary. Release of ondansetron from the solid oral dosage form provides exposure to ondansetron for a minimum period of 16 hours so as to result in a reduction in frequency of either vomiting, nausea, or diarrhea in the patient.

In an embodiment, a solid oral dosage form of the present disclosure including a total of 12 mg of ondansetron (as an equivalent amount of ondansetron HCl) is administered to a patient having diarrhea predominant irritable bowel syndrome (IBS-D) to provide rapid relief of symptoms and maintaining relief. Redosing over the course of the illness may be necessary. Release of ondansetron from the solid oral dosage form provides exposure to ondansetron for a minimum period of 16 hours so as to result in a reduction in frequency of either vomiting, nausea, or diarrhea in the patient.

In an embodiment, a solid oral dosage form of the present disclosure including a total of 24 mg of ondansetron (as an equivalent amount of ondansetron HCl) is administered to a patient having diarrhea predominant irritable bowel syndrome (IBS-D) to provide rapid relief of symptoms and maintaining relief. Redosing over the course of the illness may be necessary. Release of ondansetron from the solid oral dosage form provides exposure to ondansetron for a minimum period of 16 hours so as to result in a reduction in frequency of either vomiting, nausea, or diarrhea in the patient.

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Example 1—Manufacture of 18 mg Ondansetron Internal Cores

TABLE 1

Ondansetron Internal Core, 18 mg; Amino Acid core ("AA core")

| Item | Ingredients | % w/w | mg/tablet | Actual g/batch |
|---|---|---|---|---|
| 1 | Ondansetron HCl | 3.83 | 20.2† | 298.7* |
| 2 | Glycine, USP | 18.96 | 100 | 1327.01 |
| 3 | Hypromelose, USP (Methocel K15M Premium CR) | 18.96 | 100 | 1327.01 |
| 4 | Microcrystalline Cellulose, NF (Avicel® PH-102) | 19.84 | 104.7 | 1358.2* |
| 5 | Hypromelose, USP (Methocel K100 Premium LV) | 37.91 | 200 | 2654.03 |
| 6 | Purified Water, USP | | | 1750.0 |
| 7 | Magnesium Stearate, NF | 0.50 | 2.6 | 35.0 |
| | Totals | 100.00 | 527.5 | 7000.00 |

*adjusted based on API potency: MCC reduced to compensate
†20.2 mg of Ondansetron HCl is equivalent to 18 mg of Ondansetron The amino acid formulation ("AA core") was manufactured using low shear wet granulation. The Avicel® PH-102 microcrystalline cellulose, ondansetron HCl, glycine and HPMC K15M were mixed in a 1 cu ft V-blender for 10 minutes, discharged and delumped using a Comil equipped with a 20 mesh screen. The pre-blend was then granulated in the Hobart D300 by adding water to the blend while mixing. After the water was added the material was mixed for an additional 2 minutes. The material was granulated adequately but not overly wet, therefore no additional water was added. The wet mass was screened through an 8 mesh screen then oven dried. The dried granulation was milled using a Comil with an 18 mesh screen, blended with the extragranular HPMC K100LV and lubricant. Compression of the final blend was conducted on a 36-station Kikusui press using the 0.32"×0.58" modified oval tooling.

TABLE 2

Ondansetron Internal Portion, 18 mg; Electrolyte core ("Electrolyte core")

| Item | Ingredients | % w/w | mg/tablet | g/batch |
|---|---|---|---|---|
| 1 | Ondansetron HCl | 5.39 | 20.20† | 601.10* |
| 2 | Hypromelose, USP (Methocel K4M Premium CR) | 26.70 | 100.00 | 2670.23 |
| 3 | Sodium Citrate Anhydrous, USP (fine granular) | 13.35 | 50.00 | 1335.11 |
| 4 | Microcrystalline Cellulose, NF (Avicel® PH-102) | 54.02 | 202.30 | 5340.2* |
| 5 | Magnesium Stearate, NF (vegetable grade) | 0.53 | 2.00 | 53.40 |
| | Totals | 100.00 | 374.50 | 10000.00 |

*adjusted based on API potency: MCC reduced to compensate
†20.2 mg of Ondansetron HCl is equivalent to 18 mg of Ondansetron The electrolyte formulation ("Electrolyte core") was manufactured by blending and compression. All the materials were screened separately through a 30 mesh hand screen, charged into the V-blender and mixed for 15 minutes then lubricated. Compression was conducted on a 36-station Kikusui press using the 0.28"×0.50" modified oval tooling.

Example 2—First and Second Seal Coatings; Optional Enteric Coating

TABLE 3

Seal Coat Formula (sub coating and top coat)

| Item | Ingredients | % w/w | g/batch* |
|---|---|---|---|
| 1 | Hypromellose (Methocel E5) | 6.00 | 109.2 |
| 2 | PlasACRYL™ T20 | 0.60 | 10.92 |
| 3 | Purified Water | 93.40 | 1699.88 |
| | Total | 100.0 | 1820.00 |

*batch size is for one seal coating, with ~30% overage

TABLE 4

Enteric Coating Formula

| item | Ingredients | % w/w | g/batch* |
|---|---|---|---|
| 1 | EUDRAGIT® L30D-55 (30% dispersion) | 71.22 | 1365.68 |
| 2 | PlasACRYL™ T20 (20% emulsion) | 10.68 | 204.13 |
| 3 | Triethyl citrate | 1.08 | 21.24 |
| 4 | Purified Water | 17.02 | 768.86 |
| | Total | 100.00 | 2359.91 |

*batch size includes 30% overage

The seal coating solution was manufactured by dissolving the Methocel E5 in water, then adding the PlasACRYL™. The enteric coating suspension was manufactured by mixing the water, triethyl citrate and PlasACRYL™. The EUDRAGIT® dispersion was added; the suspension was mixed for 30 minutes then screened through a 60 mesh screen. The active suspension was manufactured by first dissolving the Methocel E5 in water, and separately dispersing the ondansetron in water and homogenizing. The Methocel solution was then added to the drug suspension, and the PlasACRYL™ was added.

Example 3—Drug Layer Overcoat

TABLE 5

Drug layer coating Formulas

| | | | 1 | 2 | 3 |
|---|---|---|---|---|---|
| | Ingredients | % w/w | g/batch* | g/batch* | g/batch* |
| 1 | Ondensatron HCl | 2.40 | 65.82 | 87.76 | 83.37 |
| 2 | Hypromellose (Methocel E5) USP | 3.60 | 98.72 | 131.63 | 0.13 |
| 3 | PlasACRYL™ (20% emulsion) | 0.90 | 24.68 | 32.91 | 31.26 |
| 4 | Purified Water | 93.10 | 2553.13 | 3404.18 | 3233.97 |
| | Total | 100.00 | 2742.35 | 3656.47 | 3473.65 |

*Batch sizes include an 18% overage to account for manufacturing losses

The tablets were coated with the required coatings as listed in Tables 6-8. Weight gain was monitored by measuring the weight of 50 tablets every 10 minutes. Due to equipment availability, the 1$^{st}$ two batches were coated using the R&D tablet coater (O'Hara LabMX). The 3$^{rd}$ batch was manufactured using the cGMP equipment which will be used for the CTM manufactures.

TABLE 6

Coating Parameters; Product 1
AA core

| O'Hara LabMX | Initial seal coat | IR coat | Final topcoat |
|---|---|---|---|
| Starting charge (kg) | 3.956 | 3.953 | 4.058 |
| Inlet temp (° C.) | 61.8-62.4 | 59.9-62.5 | 61.0-63.1 |
| Outlet temp (° C.) | 42.5-44.1 | 43.5-44.1 | 42.5-45.5 |
| Pan speed (rpm) | 12 | 12 | 12 |
| Spray rate (g/min) | 25.3-27.0 | 24.2-26.5 | 22.1-27.5 |
| Atomization pressure (psi) | 25 | 25 | 25 |
| Inlet airflow (cfm) | 200 | 200 | 200 |
| Final weight gain | 2.05% | 20.9 mg/tablet | 2.09% |
| Coating efficiency | | 100% | |

TABLE 7

Coating Parameters; Product 2
Electrolyte core

| O'Hara LabMX | Initial seal coat | IR coat | Final topcoat |
|---|---|---|---|
| Starting charge | 3.745 | 3.814 | 3.990 |
| Inlet temp (° C.) | 60.5-62.2 | 60.0-61.4 | 61.0-62.8 |
| Outlet temp (° C.) | 42.4-43.8 | 42.2-43.7 | 42.2-44.0 |
| Pan speed (rpm) | 12 | 12 | 12 |
| Spray rate (g/min) | 25.1-26.8 | 25.8-27.6 | 24.2-30.5 |
| Atomization pressure (psi) | 25 | 25 | 25 |

TABLE 7-continued

Coating Parameters; Product 2
Electrolyte core

| O'Hara LabMX | Initial seal coat | IR coat | Final topcoat |
|---|---|---|---|
| Inlet airflow (cfm) | 200 | 200 | 200 |
| Final weight gain | 2.12% (79.4 g) | 20.2 mg/tablet | 2.23% |
| Coating efficiency | | 93% | |

TABLE 8

Coating Parameters; Product 3
Electrolyte core, Enteric coat + Drug overcoat

| Driam Driacoater | Initial seal coat | Enteric coat | Drug overcoat | Final topcoat |
|---|---|---|---|---|
| Starting charge | 3.558 | 3.627 | 3.991 | 4.143 |
| Inlet temp (° C.) | 44.0-60.0 | 42-47 | 45-47 | 44-48 |
| Outlet temp (° C.) | 43-48 | 41-46 | 42-44 | 41-45 |
| Pan speed (rpm) | 12 | 12 | 12 | 12 |
| Spray rate (g/min) | 22.7-24.6 | 16.7-19.6 | 23.1-27.3 | 24.7-27.5 |
| Atomization pressure (psi) | 35 | 30-35 | 30 | 30 |
| Inlet airflow (cfm) | 300 | 300 | 300 | 300 |
| Final weight gain | 2.50% | 10.24% | 19.5 mg/tablet | 2.3 3% |
| Coating efficiency | | | 84.5% | |

TABLE 9

Overall Batches

| | Product # 1 | | | Product # 2 | | | Product # 3 | | |
|---|---|---|---|---|---|---|---|---|---|
| Ingredient | % w/w | Mg/tablet | g/batch | % w/w | Mg/tablet | g/batch | % w/w | Mg/tablet | g/batch |
| Ondansetron CDT tablet, 18 mg (amino acid formula) | 92.81 | 527.50 | 3956.25 | | | | | | |
| Ondansetron CDT tablet, 18 mg (electrolyte formula) | | | | 91.53 | 374.50 | 3745.00 | 83.57 | 374.50 | 3557.75 |
| Hypromellose seal coat | 1.86 | 10.55 | 79.13 | 1.83 | 7.49 | 74.90 | 1.67 | 7.49 | 71.16 |
| Enteric coating (Eudragit ®) | | | | | | | 8.52 | 38.20 | 362.90 |
| Ondansetron drug overcoat (39% Ondansetron HCl) | 3.37 | 19.15* | 143.63 | 4.68 | 19.15* | 191.50 | 4.27 | 19.15* | 181.93 |
| Hypromellose seal coat | 1.96 | 11.14 | 83.58 | 1.96 | 8.02 | 80.23 | 1.96 | 8.79 | 83.47 |
| Total | 100.00 | 568.34 | 4262.58 | 100.00 | 409.16 | 4091.63 | 100.00 | 448.13 | 4257.20 |

Example 4—Dissolution Profile

TABLE 10

Dissolution (Ondansetron Bimodal Release Tablets, 24 mg)

| | Amino acid | Electrolyte | Electrolyte with enteric coating |
|---|---|---|---|
| Tablet strength (mg) | 24 | 24 | 24 |
| Apparatus | II (paddle) | II (paddle) | II (paddle) |
| Sinker | Japanese basket | Japanese basket | Japanese basket |
| # units | 6 | 6 | 6 |
| Speed (rpm) | 50 | 50 | 50 |

TABLE 10-continued

| Dissolution (Ondansetron Bimodal Release Tablets, 24 mg) | | | | | | | | |
|---|---|---|---|---|---|---|---|---|
| Dissolution media | Time point (hrs) | Mean % dissolved | % RSD | Mean % dissolved | % RSD | | Mean % dissolved | % RSD |
| water | 0.5 | 25.8 | 9.9 | 25.3 | 6.7 | 0.1N HCl | 25.2 | 4.8 |
| | 2 | 38 | 5.5 | 41.4 | 4 | | 25.8 | 4.9 |
| | 3 | 45.1 | 5.4 | 51.1 | 3.4 | pH 6.8 | 33.8 | 7.8 |
| | 4 | 50.6 | 4.9 | 58.1 | 3.4 | phosphate | 44 | 4.9 |
| | 6 | 60 | 4.1 | 69.7 | 3.8 | buffer | 61.4 | 5.4 |
| | 9 | 71.5 | 3.9 | 82.7 | 4.2 | | 79.7 | 2.7 |
| | 12 | 79.5 | 3.6 | 93.1 | 4.1 | | 89.5 | 2.5 |
| | 15 | 84.6 | 3.4 | 99.2 | 4.1 | | 95.8 | 3.6 |
| | 18 | 88 | 3.4 | 102.5 | 3.8 | | 98.6 | 3.1 |
| | 21 | 90.8 | 3.3 | 103.8 | 3.7 | | 100 | 3.6 |
| | 24 | 93.1 | 3.1 | 104.6 | 3.6 | | 101.6 | 3.4 |

Figure 2:
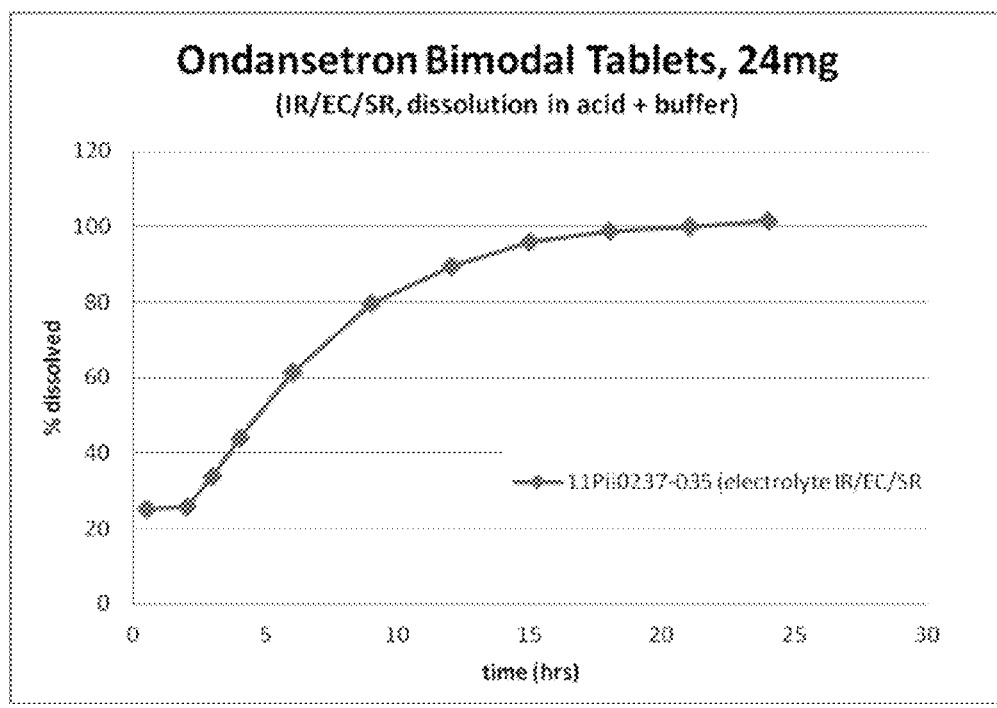
FIG. 2 illustrates the dissolution profile of ondansetron from an embodiment of an extended release solid dosage form of the present disclosure as measured using a USP type 2 (paddle) dissolution system at 50 rpm, at a temperature of 37±0.5° with 0.1N HCL and pH 6.8 phosphate buffer as a dissolution medium.

Table 10 in conjunction with FIG. 1 and FIG. 2 show the dissolution profile for Products 1, 2 and 3. For product 1, there was an initial 25% burst, followed by a sustained release over 24 hours. For product 2, there was an initial 25% burst, followed by a sustained release over 24 hours. For product 3, there was initial 25% burst, followed by a lag in release while in acid.

Example 5—Manufacture of Ondansetron Internal Electrolyte Core

Figure 3:
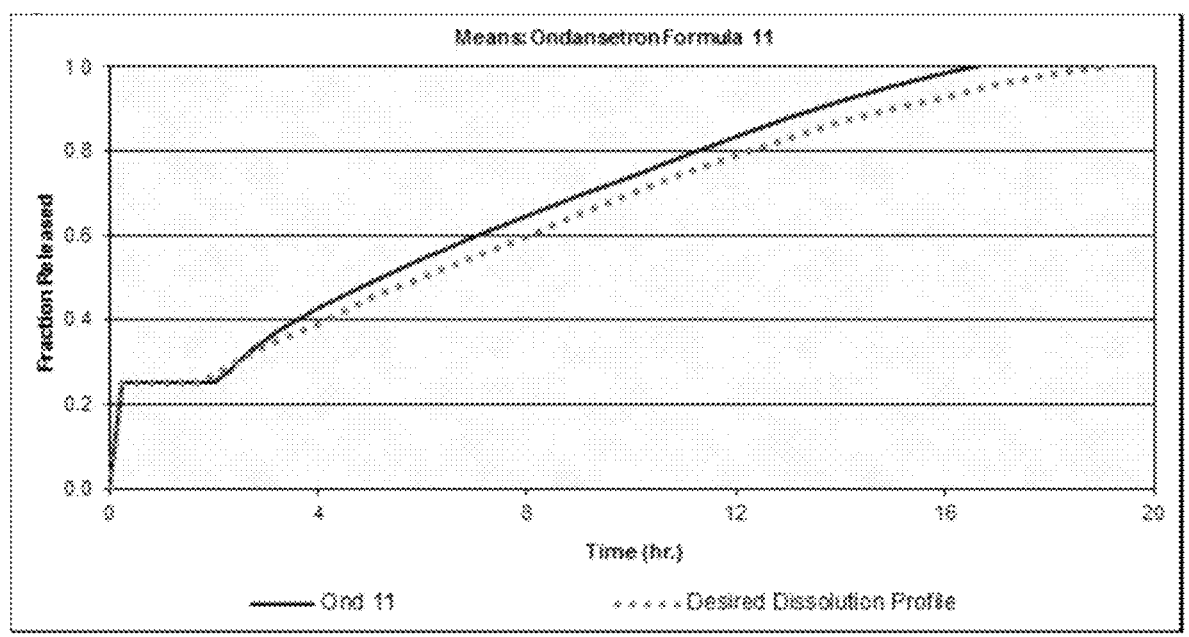
FIG. 3 illustrates the dissolution profile of ondansetron from an embodiment of an extended release solid dosage form of the present disclosure as measured using a USP type 2 (paddle) dissolution system at 50 rpm, at a temperature of 37±0.5° with 0.1N HCL and pH 6.8 phosphate buffer as a dissolution medium.

Ondansetron HCl tablet cores were prepared through dry-blend and direct compression. Details of the formulation ingredients are depicted in Tables 11 and 12. The dissolution profile (assuming enteric coating and 6 mg immediate release drug coating) for this formula is shown in FIG. 3.

TABLE 11

| Ondansetron Electrolyte 11 - tablet core | | |
|---|---|---|
| Ondansetron HCl Electrolyte 11 | % w/w | mg/dosage |
| Ondansetron HCl | 5.30% | 22.5 |
| sodium citrate | 11.78% | 50 |
| HPMC K4M | 23.56% | 100 |
| MCC | 47.11% | 200 |
| mg stearate | 0.47% | 2 |
| Total | | 374.5 |

TABLE 12

| 22.5 mg Ondansetron HCl Formulation 11 | | | | | |
|---|---|---|---|---|---|
| Raw Material | Purpose | Manufacturer | Lot Number | w/w % | mg/dosage |
| Ondansetron HCl | API | DRL | ON01 31 05 | 5.30% | 22.5 |
| HPMC K4M | Polymer | Colorcon | WP193724 | 23.56% | 100.00 |
| Sodium Citrate | Electrolyte | Gadot Biochemical Ind. | 48010004 | 11.78% | 50.00 |
| Avicel MCC PH 102 | Flow Agent | FMC Biopolymer | P208819629 | 47.11% | 200.00 |
| Mg Stearate | Lubricant | Mallinckrodt | E17591 | 0.47% | 2.00 |
| | | Total | | 100% | 374.5 |

Example 6—Dissolution Profile

Figure 4:
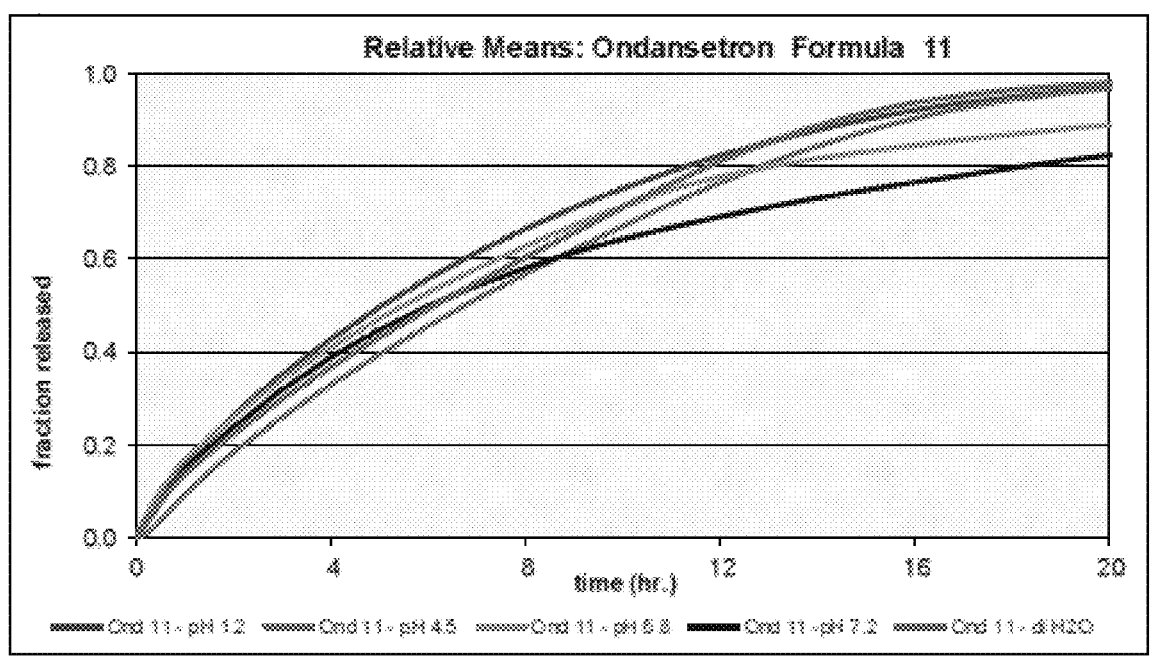
FIG. 4 illustrates the dissolution profiles of ondansetron from an embodiment of an extended release solid dosage form of the present disclosure as measured using a USP type 2 (paddle) dissolution system at 50 rpm, at a temperature of 37±0.5° with physiologically relevant media within a pH range of 1.2 to 7.2, approximating levels found through the GI tract.

In vitro dissolution was performed with physiologically relevant media within a pH range of 1.2 to 7.2, approximating levels found through the GI tract. Due to differences in solubility at various pH of the ondansetron HCl API, absorbance max was used to calculate dissolution release rather than the calibration curve created with the API in water. Dissolution testing results for media: pH1 0.2, 4.5, 6.8, 7.2 and diH$_2$O can be seen in FIG. 4.

Example 7—In Vivo Testing of Solid Dosage Forms

A single center, randomized, laboratory-blinded, 4-period, 4-sequence, crossover design study was carried out in healthy male and female subjects. The following investigational products were to be administered under fasting conditions:

Test-1: 1 × Ondansetron 24 mg bimodal tablet (amino acid core) Batch no.: 19401.001A
Test-2: 1 × Ondansetron 24 mg bimodal tablet (electrolyte core) Batch no.: 19404.001A
Test-3: 1 × Ondansetron 24 mg bimodal tablet (enteric coated electrolyte core) Batch no.: 19403.001A
Reference: 3 × Zofran ® 8 mg tablets (1 × 8 mg tablet administered three-times daily, at 8-hour intervals: in the morning following a 10-hour overnight fast, in the afternoon and in the evening)

The products were to be administered to 28 healthy male and female subjects according to Table 13.

|  | Period 1 | Period 2 | Period 3 | Period 4 |
|---|---|---|---|---|
| Sequence 1 (n = 7) | Test-1 | Reference | Test-2 | Test-3 |
| Sequence 2 (n = 7) | Test-2 | Test-1 | Test-3 | Reference |
| Sequence 3 (n = 7) | Test-3 | Test-2 | Reference | Test-1 |
| Sequence 4 (n = 7) | Reference | Test-3 | Test-1 | Test-2 |

Selection of Doses in the Study

The dose was chosen to achieve similar exposure as with the marketed immediate-release formulation (Zofran® 8 mg) when administered three-time daily.

Selection and Timing of Dose for Each Subject

Subjects fasted overnight for at least 10 hours prior to morning drug administration.

Tests 1-3
A single dose of the assigned Test formulation was administered orally with approximately 240 mL of water at ambient temperature, starting at 07:30, to one subject per minute.

Reference
The assigned Reference formulation was administered orally (three-times daily, at 8-hour intervals) with approximately 240 mL of water at ambient temperature, starting at 07:30, to one subject per minute. Subsequent drug administrations took place in the afternoon and in the evening at 15:30 and 23:30, respectively.

Fasting continued for at least 4 hours following morning drug administration, after which a standardized lunch was served. The lunch was to be completed no later than 5 hours following morning drug administration. All meals were served at appropriate times thereafter, but not before 9 hours after morning drug administration. The supper was not to be served before 11 hours after the morning drug administration and was to be completed no later than 13 hours following morning drug administration. Furthermore, the light snack was to be completed no later than 13 hours after the morning drug administration. Water was allowed ad libitum until 1 hour pre-dose and beginning 1 hour after each drug administration.

Efficacy and Safety Measurements Assessed and Flow Chart
Pharmacokinetic Assessments Blood samples for pharmacokinetic measurements were collected prior to and up to 32 hours (serial sampling) after each morning drug administration. The direct measurements of this study were the plasma concentrations of ondansetron. These concentrations were obtained by analysis of the plasma derived from the blood samples drawn during this study. The total volume of blood collected per subject (639 mL for males and 653 mL for females) is considered to have a negligible or no impact on the pharmacokinetic profiles of the drugs and the assessment of bioequivalence. Furthermore, it is considered to have a negligible impact on subjects' safety.

Drug Concentration Measurements

Tests 1-3 (21 Blood Samples):
The first blood sample of each period, i.e. the blank plasma sample, was collected prior to drug administration while the others were collected 0.25, 0.5, 1, 1.5, 2, 2.5, 3, 3.5, 4, 5, 6, 7, 8, 9, 10, 12, 16, 20, 24 and 32 hours after drug administration in one tube of 6 mL ($K_2$ EDTA Vacutainers)

Reference (33 Blood Samples):
The first blood sample of each period, i.e. the blank plasma sample, was collected prior to the morning drug administration while the others were collected 0.25, 0.5, 1, 1.5, 2, 2.5, 3, 4, 6, 8, 8.25, 8.5, 9, 9.5, 10, 10.5, 11, 12, 14, 16, 16.25, 16.5, 17, 17.5, 18, 18.5, 19, 20, 22, 24, 28 and 32 hours following the morning drug administration in one tube of 6 mL ($K_2$ EDTA Vacutainers). Samples at 8-hour and 16-hour were collected within 5 minutes before the drug administration (the afternoon and evening administrations).

Ondansetron—Test-1 vs Reference

Figure 5:
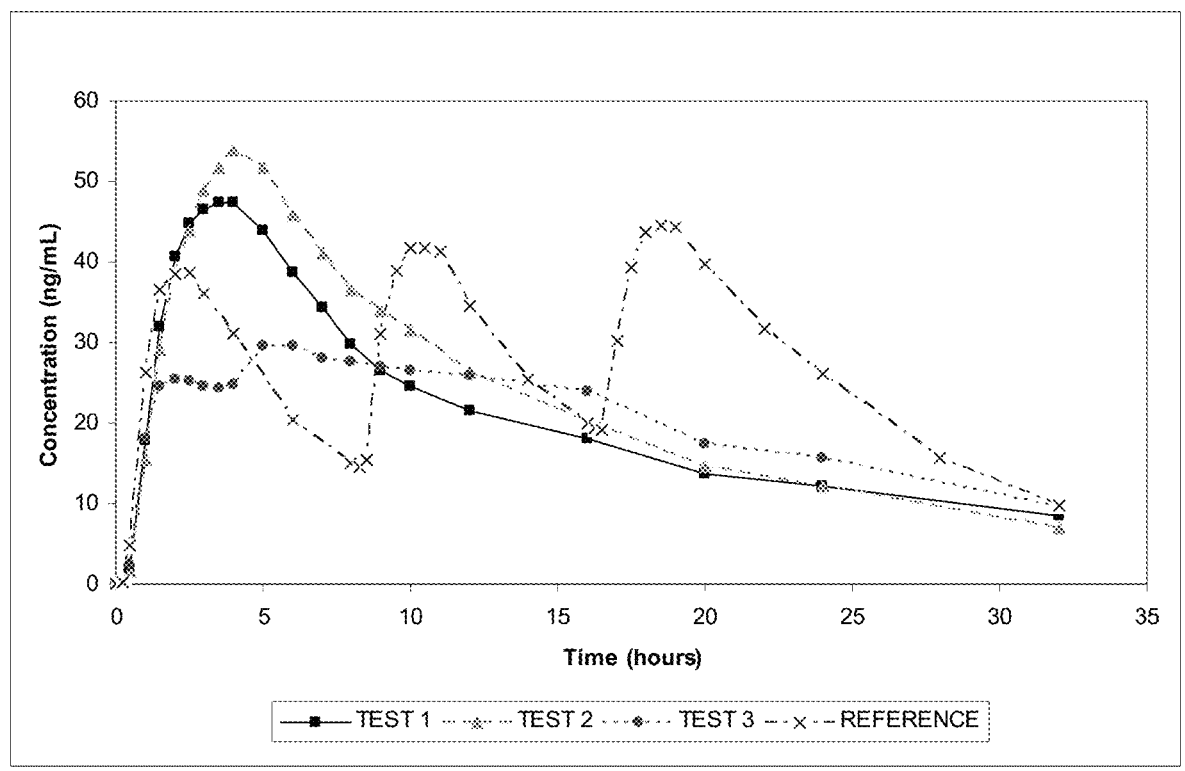
FIG. 5 illustrates the mean measured plasma concentration versus time profile of ondansetron, derived from the administration of various embodiments of extended release solid dosage forms of the present disclosure and a reference product.
Figure 6:
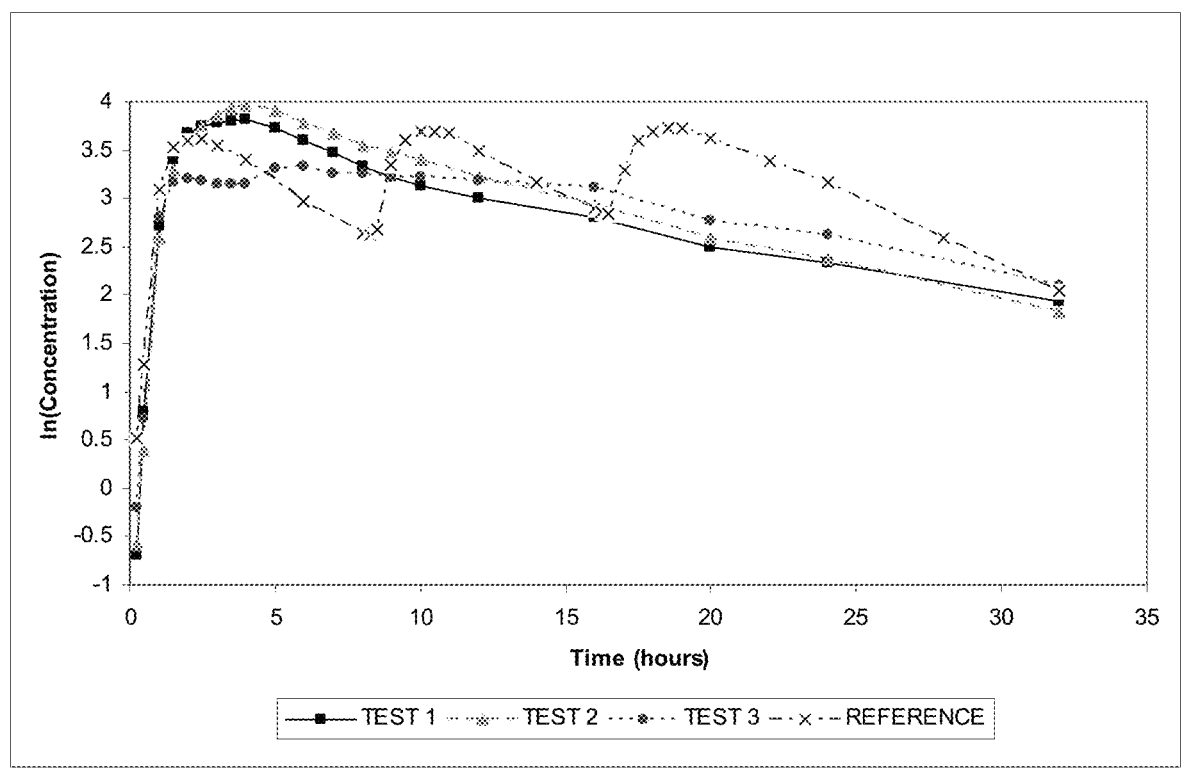
FIG. 6 illustrates the 1n-transformed mean concentration versus time profile of ondansetron, derived from the administration of various embodiments of extended release solid dosage forms of the present disclosure and a reference product.

Twenty-six (26) subjects were included in the comparison between Test-1 and Reference. A summary of the pharmacokinetic parameters and the standards for comparative bioavailability are presented in Tables 14 and 15. The mean measured plasma concentration versus time profile, derived from the administration of the Test-1 and Reference products, is depicted in FIG. 5, whereas the ln-transformed mean concentration versus time profile is depicted in FIG. 6.

TABLE 14

Summary of Main Study Results - Ondansetron - Test-1 vs Reference

|  | TEST-1 | | REFERENCE | |
|---|---|---|---|---|
| PARAMETER | MEAN | C.V. (%) | MEAN | C.V. (%) |
| $C_{max}$ (ng/mL) | 50.669 | 30.3 | 50.731 | 30.5 |
| ln ($C_{max}$) | 3.8742 | 8.8 | 3.8835 | 7.7 |
| $T_{max}$ (hours)§ | 3.50 | 23.6 | 17.50 | 45.7 |
| $AUC_T$ (ng · h/mL) | 659.098 | 34.5 | 854.517 | 37.4 |
| ln ($AUC_T$) | 6.4337 | 5.4 | 6.6897 | 5.3 |
| $AUC_\infty$ (ng · h/mL) | 795.397 | 43.3 | 946.030 | 43.5 |
| ln ($AUC_\infty$) | 6.5921 | 6.5 | 6.7741 | 5.8 |
| $AUC_{T/\infty}$ (%) | 84.61 | 12.2 | 92.07 | 5.8 |
| $K_{el}$ (hours$^{-1}$) | 0.0671 | 29.8 | 0.1391 | 26.7 |
| $T_{1/2el}$ (hours) | 11.72 | 46.3 | 5.40 | 31.5 |
| $AUC_{0-24}$ (ng · h/mL) | 577.151 | 32.6 | 720.455 | 33.6 |
| $C_{24}$ (ng/mL) | 12.134 | 58.3 | 26.115 | 50.6 |

§For $T_{max}$, the median is presented

TABLE 15

Comparison of Results with Standards for Bioequivalence - Ondansetron - Test-1 vs Reference

|  | INTRA-SUBJECT | GEOMETRIC LSMEANS * | | RATIO | 90% CONFIDENCE LIMITS (%) | |
|---|---|---|---|---|---|---|
| PARAMETER | C.V. (%) | TEST-1 | REFERENCE | (%) | LOWER | UPPER |
| $C_{max}$ | 14.0 | 48.222 | 48.685 | 99.05 | 92.89 | 105.62 |
| $AUC_T$ | 11.3 | 625.797 | 807.106 | 77.54 | 73.60 | 81.68 |
| $AUC_\infty$ | 14.3 | 738.123 | 879.247 | 83.95 | 78.46 | 89.82 |

* units are ng/mL for $C_{max}$ and ng · h/mL for $AUC_T$ and $AUC_\infty$

The number of subjects included in the statistical analysis of these parameters was n=24 for the Test-1 and n=26 for the Reference. The mean $C_{max}$ were respectively, 50.669 ng/mL and 50.731 ng/mL for the Test-1 and Reference formulations. The Test-1 to Reference $C_{max}$ ratio of geometric LSmeans was 99.05% (90% CI: 92.89 to 105.62%). This result thus demonstrates that the ratio and corresponding 90% confidence interval of the relative $C_{max}$ geometric LSmeans of the Test-1 to Reference formulation are within the pre-specified 80.00 to 125.00% range. The median $T_{max}$ was 3.50 and 17.50 hours for the Test-1 and Reference formulations, respectively. The mean $AUC_T$ were respectively, 659.098 ng·h/mL and 854.517 ng·h/mL for the Test-1 and Reference formulations. The Test-1 to Reference $AUC_T$ ratio of geometric LSmeans was 77.54% (90% CI: 73.60 to 81.68%). This result thus demonstrates that the ratio and corresponding 90% confidence interval of the relative $AUC_T$ geometric LSmeans of the Test-1 to Reference formulation are outside the pre-specified 80.00 to 125.00% range. The mean $K_{el}$ was 0.0671 hours$^{-1}$ for the Test-1 formulation and 0.1391 hours$^{-1}$ for the Reference formulation. The mean $T_{1/2el}$ value was 11.72 and 5.40 hours, for the Test-1 and Reference formulations, respectively. The mean $AUC_\infty$ were respectively, 795.397 ng·h/mL and 946.030 ng·h/mL for the Test-1 and Reference formulations. The Test-1 to Reference $AUC_\infty$ ratio of geometric LSmeans was 83.95% (90% CI: 78.46 to 89.82%). This result thus demonstrates that the 90% confidence interval of the relative $AUC_\infty$ geometric LSmeans of the Test-1 to Reference formulation is outside the pre-specified 80.00 to 125.00% range. The mean $AUC_T$ over $AUC_\infty$ individual ratio ($AUC_{T/\infty}$) were respectively, 84.61% and 92.07% for the Test-1 and Reference formulations.

Ondansetron—Test-2 vs Reference

Twenty-six (26) subjects were included in the comparison between Test-2 and Reference. A summary of the pharmacokinetic parameters and the standards for comparative bioavailability are presented in Tables 16 and 17. The mean measured plasma concentration versus time profile, derived from the administration of the Test-2 and Reference products, is depicted in FIG. 5, whereas the ln-transformed mean concentration versus time profile is depicted in FIG. 6.

TABLE 16

Summary of Main Study Results - Ondansetron - Test-2 vs Reference

|  | TEST-2 |  | REFERENCE |  |
| --- | --- | --- | --- | --- |
| PARAMETER | MEAN | C.V. (%) | MEAN | C.V. (%) |
| $C_{max}$ (ng/mL) | 55.718 | 24.0 | 50.731 | 30.5 |
| ln ($C_{max}$) | 3.9889 | 6.7 | 3.8835 | 7.7 |
| $T_{max}$ (hours)$^\S$ | 4.00 | 13.6 | 17.50 | 45.7 |
| $AUC_T$ (ng · h/mL) | 730.199 | 31.7 | 854.517 | 37.4 |
| ln ($AUC_T$) | 6.5477 | 4.7 | 6.6897 | 5.3 |
| $AUC_\infty$ (ng · h/mL) | 847.660 | 37.7 | 946.030 | 43.5 |
| ln ($AUC_\infty$) | 6.6836 | 5.2 | 6.7741 | 5.8 |
| $AUC_{T/\infty}$ (%) | 87.44 | 5.9 | 92.07 | 5.8 |
| $K_{el}$ (hours$^{-1}$) | 0.0676 | 23.0 | 0.1391 | 26.7 |
| $T_{1/2el}$ (hours) | 10.84 | 25.8 | 5.40 | 31.5 |
| $AUC_{0-24}$ (ng · h/mL) | 653.663 | 29.5 | 720.455 | 33.6 |
| $C_{24}$ (ng/mL) | 12.088 | 52.4 | 26.115 | 50.6 |

$^\S$For $T_{max}$, the median is presented

TABLE 17

Comparison of Results with Standards for Bioequivalence - Ondansetron - Test-2 vs Reference

|  | INTRA-SUBJECT | GEOMETRIC LSMEANS * |  | RATIO | 90% CONFIDENCE LIMITS (%) |  |
| --- | --- | --- | --- | --- | --- | --- |
| PARAMETER | C.V. (%) | TEST-2 | REFERENCE | (%) | LOWER | UPPER |
| $C_{max}$ | 14.0 | 54.008 | 48.685 | 110.93 | 104.03 | 118.30 |
| $AUC_T$ | 11.3 | 700.467 | 807.106 | 86.79 | 82.38 | 91.43 |
| $AUC_\infty$ | 14.3 | 803.436 | 879.247 | 91.38 | 85.57 | 97.58 |

* units are ng/mL for $C_{max}$ and ng · h/mL for $AUC_T$ and $AUC_\infty$

The mean $C_{max}$ were respectively, 55.718 ng/mL and 50.731 ng/mL for the Test-2 and Reference formulations. The Test-2 to Reference $C_{max}$ ratio of geometric LSmeans was 110.93% (90% CI: 104.03 to 118.30%). This result thus demonstrates that the ratio and corresponding 90% confidence interval of the relative $C_{max}$ geometric LSmeans of the Test-2 to Reference formulation are within the pre-specified 80.00 to 125.00% range. The median $T_{max}$ was 4.00 and 17.50 hours for the Test-2 and Reference formulations, respectively. The mean $AUC_T$ were respectively, 730.199 ng·h/mL and 854.517 ng·h/mL for the Test-2 and Reference formulations. The Test-2 to Reference $AUC_T$ ratio of geometric LSmeans was 86.79% (90% CI: 82.38 to 91.43%). This result thus demonstrates that the ratio and corresponding 90% confidence interval of the relative $AUC_T$ geometric LSmeans of the Test-2 to Reference formulation are within the pre-specified 80.00 to 125.00% range. The mean $K_{el}$ was 0.0676 hours$^{-1}$ for the Test-2 formulation and 0.1391 hours$^{-1}$ for the Reference formulation. The mean $T_{1/2el}$ value was 10.84 and 5.40 hours, for the Test-2 and Reference formulations, respectively. The mean $AUC_\infty$ were respectively, 847.660 ng·h/mL and 946.030 ng·h/mL for the Test-2 and Reference formulations. The Test-2 to Reference $AUC_\infty$ ratio of geometric LSmeans was 91.38% (90% CI: 85.57 to 97.58%). This result thus demonstrates that the ratio and corresponding 90% confidence interval of the relative $AUC_\infty$ geometric LSmeans of the Test-2 to Reference formulation are within the pre-specified 80.00 to 125.00% range. The mean $AUC_T$ over $AUC_\infty$ individual ratio ($AUC_{T/\infty}$) were respectively, 87.44% and 92.07% for the Test and Reference formulations.

Ondansetron—Test-3 vs Reference

Twenty-five (25) observations were included for the Test-3 and 26 observations were included for the Reference. A summary of the pharmacokinetic parameters and the standards for comparative bioavailability are presented in Tables 18 and 19. The mean measured plasma concentration versus time profile, derived from the administration of the Test-3 and Reference products, is depicted in FIG. 5, whereas the ln-transformed mean concentration versus time profile is depicted in FIG. 6.

TABLE 18

Summary of Main Study Results - Ondansetron - Test-3 vs Reference

| PARAMETER | TEST-3 MEAN | C.V. (%) | REFERENCE MEAN | C.V. (%) |
|---|---|---|---|---|
| $C_{max}$ (ng/mL) | 32.958 | 28.6 | 50.731 | 30.5 |
| ln ($C_{max}$) | 3.4514 | 9.1 | 3.8835 | 7.7 |
| $T_{max}$ (hours)§ | 5.00 | 52.2 | 17.50 | 45.7 |
| $AUC_T$ (ng · h/mL) | 646.611 | 34.6 | 854.517 | 37.4 |
| ln ($AUC_T$) | 6.4122 | 5.6 | 6.6897 | 5.3 |
| $AUC_\infty$ (ng · h/mL) | 830.321 | 47.2 | 946.030 | 43.5 |
| ln ($AUC_\infty$) | 6.6320 | 6.3 | 6.7741 | 5.8 |
| $AUC_{T/\infty}$ (%) | 80.15 | 13.7 | 92.07 | 5.8 |
| $K_{el}$ (hours$^{-1}$) | 0.0640 | 38.3 | 0.1391 | 26.7 |
| $T_{1/2el}$ (hours) | 12.73 | 44.2 | 5.40 | 31.5 |
| $AUC_{0-24}$ (ng · h/mL) | 546.657 | 32.9 | 720.455 | 33.6 |
| $C_{24}$ (ng/mL) | 15.553 | 50.8 | 26.115 | 50.6 |

§For $T_{max}$, the median is presented

TABLE 19

Comparison of Results with Standards for Bioequivalence - Ondansetron - Test-3 vs Reference

| PARAMETER | INTRA-SUBJECT C.V. (%) | GEOMETRIC LSMEANS * TEST-3 | GEOMETRIC LSMEANS * REFERENCE | RATIO (%) | 90% CONFIDENCE LIMITS (%) LOWER | 90% CONFIDENCE LIMITS (%) UPPER |
|---|---|---|---|---|---|---|
| $C_{max}$ | 14.0 | 31.973 | 48.685 | 65.67 | 61.54 | 70.09 |
| $AUC_T$ | 11.3 | 617.172 | 807.106 | 76.47 | 72.54 | 80.61 |
| $AUC_\infty$ | 14.3 | 777.120 | 879.247 | 88.38 | 82.53 | 94.65 |

* units are ng/mL for $C_{max}$ and ng · h/mL for $AUC_T$ and $AUC_\infty$

The number of subjects included in the statistical analysis of these parameters was n=23 for the Test-3 and n=26 for the Reference. The mean $C_{max}$ were respectively, 32.958 ng/mL and 50.731 ng/mL for the Test-3 and Reference formulations. The Test-3 to Reference $C_{max}$ ratio of geometric LSmeans was 65.67% (90% CI: 61.54 to 70.09%). This result thus demonstrates that the ratio and corresponding 90% confidence interval of the relative $C_{max}$ geometric LSmeans of the Test-3 to Reference formulation are outside the pre-specified 80.00 to 125.00% range. The median $T_{max}$ was 5.00 and 17.50 hours for the Test-3 and Reference formulations, respectively. The mean $AUC_T$ were respectively, 646.611 ng·h/mL and 854.517 ng·h/mL for the Test-3 and Reference formulations. The Test-3 to Reference $AUC_T$ ratio of geometric LSmeans was 76.47% (90% CI: 72.54 to 80.61%). This result thus demonstrates that the ratio and corresponding 90% confidence interval of the relative $AUC_T$ geometric LSmeans of the Test-3 to Reference formulation are outside the pre-specified 80.00 to 125.00% range. The mean $K_{el}$ was 0.0640 hours$^{-1}$ for the Test-3 formulation and 0.1391 hours$^{-1}$ for the Reference formulation. The mean $T_{1/2el}$ value was 12.73 and 5.40 hours, for the Test-3 and Reference formulations, respectively. The mean $AUC_\infty$ were respectively, 830.321 ng·h/mL and 946.030 ng·h/mL for the Test-3 and Reference formulations. The Test-3 to Reference $AUC_\infty$ ratio of geometric LSmeans was 88.38% (90% CI: 82.53 to 94.65%). This result thus demonstrates that the ratio and corresponding 90% confidence interval of the relative $AUC_\infty$ geometric LSmeans of the Test-3 to Reference formulation are within the pre-specified 80.00 to 125.00% range. The mean $AUC_T$ over $AUC_\infty$ individual ratio ($AUC_{T/\infty}$) were respectively, 80.15% and 92.07% for the Test-3 and Reference formulations.

Example 8—Formulation Development of 36 to 48 Hour Extended Release Oral Solid Dosage Form of Ondansetron It may be desirable to develop a 36 to 48 hour extended release oral solid dosage form of ondansetron comprising 36 mg to 48 mg of ondansetron hydrochloride.

Table 20 presents the dry blend direct compression composition of extended release core tablet formulations 20 and 28 mg of ondanstron free base. Materials used for ondanstron hydrochloride sustained release core tablet development were similar to those listed in Example 1, Table 2 of the 24 mg bimodal tablet formulation (18 mg of ondansetron free base in core tablet) except for the Hypromelose K4M premium DC grade utilized instead of Hypromelose K4M premium.

TABLE 20

Composition of Dry Blend Direct Compression Extended Release Ondansetron Formulation approach

| Ingredient Name | Ondansetron 18 mg free base core Reference Formulation | Dry Blend Formulation Prototypes Lab scale L004-04~ | | | |
|---|---|---|---|---|---|
| | | 001 (20 mg free base) % (w/w) | 003 | 005 (28 mg free base) | 007 |
| Ondansetron HCl | 5.39* | 6.64 | 9.30 | 9.30 | 9.30 |
| Hypromelose K4M premium DC | 26.7 | 26.70 | 41.30 | 34.30 | 30.00 |
| Sodium dihydrogen citrate anhydrous | 13.35 | 13.35 | 13.55 | 13.35 | 13.35 |

TABLE 20-continued

Composition of Dry Blend Direct Compression Extended Release Ondansetron Formulation approach

| Ingredient Name | Ondansetron 18 mg free base core Reference Formulation | Dry Blend Formulation Prototypes Lab scale L004-04~ | | | |
|---|---|---|---|---|---|
| | | 001 (20 mg free base) | 003 | 005 (28 mg free base) | 007 |
| | % (w/w) | | | | |
| Microcrystalline Cellulose type 102 (TABULOSE ®-102) | 54.02* | 52.78 | 35.52 | 42.52 | 46.82 |
| Magnesium stearate (Ligamed MF-2-V) | 0.53 | 0.53 | 0.53 | 0.53 | 0.53 |
| Total | 99.99 | 100.0 | 100.0 | 100 | 100.0 |

*Before potency adjustment

Table 21 presents the dry blend direct compression composition of core tablet 8 mg of Ondansetron free base formulation assessed to be chronodosed coated.

TABLE 21

Composition of Dry Blend Direct Compression Core Tablet Formulation Ondansetron to be Chronodosed coated approach

| Ingredient Name | Dry Blend Formulation Prototypes Lab scale (8 mg free base) L004-04~ | | | |
|---|---|---|---|---|
| | 002 | 004 | 006 | 008 |
| | % (w/w) | | | |
| Ondansetron HCl | 12.44 | 12.44 | 12.44 | 12.44 |
| Microcrystalline Cellulose type 102 (TABULOSE ®-102) | 87.03 | 39.03 | 39.03 | 39.03 |
| Lactose monohydrate 80 (TABULOSE ®-80) | — | 48.00 | 44.00 | 40.00 |
| Sodium starch glucolate (Explosol) | — | — | 4.00 | 8.00 |
| Magnesium stearate (Ligamed MF-2-V) | 0.53 | 0.53 | 0.53 | 1.53 |
| Total | 100.0 | 100.0 | 100 | 100 |

Example 9—Dry Blending Approach Process Description

A dry blend was processed using a PK Blend Master laboratory blender (Patterson-Kelly, East Stroudsburg, Pa., USA) equipped with 1.5 L V-blender capacity for the laboratory scale formulation L004-04001 to -04008 (Tables 22A and 22B and Tables 23A and 23B respectively). All the materials were screened separately through a 30 mesh hand screen, charged into the V-blender and mixed for 15 minutes at 25 rpm without the lubricant which was then added and mixed for 3 additional minutes. The same blending method was applied to the lots -04002, -04004, -04006 and -04004 intended to be chronodosed coated.

TABLE 22A

Extended Release Ondansetron Core Formulation Composition Approach L004-04001 and L003

| Ingredient Name | Dry Blend Formulation Prototypes Lab scale L004-04~ | | | | | |
|---|---|---|---|---|---|---|
| | 001 (20 mg free base) | | | 003 (28 mg free base) | | |
| | % (w/w) | Batch size (g) | 001 (Low Hardness) / 001A (High Hardness) mg/unit | % (w/w) | Batch size (g) | mg/unit |
| Ondansetron HCl | 6.64 | 6.64 | 24.9 | 9.30 | 9.30 | 34.8 |
| Hypromelose K4M premium DC | 26.70 | 26.70 | 100.0 | 41.30 | 41.30 | 154.7 |
| Sodium dihydrogen citrate anhydrous | 13.35 | 13.35 | 50.0 | 13.55 | 13.55 | 50.0 |
| Microcrystalline Cellulose type 102 (TABULOSE ®-102) | 52.78 | 52.78 | 197.6 | 35.52 | 35.52 | 133.0 |
| Magnesium stearate (Ligamed MF-2-V) | 0.53 | 0.53 | 2.0 | 0.53 | 0.53 | 2.0 |
| Total | 100.0 | 100 | 374.5 | 100.0 | 100.0 | 374.5 |

TABLE 22B

Extended Release Ondansetron Core Formulation Composition Approach L005 and L007

Dry Blend Formulation Prototypes Lab scale L004-04~

| Ingredient Name | 005 (28 mg free base) | | | 007 | | |
|---|---|---|---|---|---|---|
| | % (w/w) | Batch size (g) | mg/unit | % (w/w) | Batch size (g) | mg/unit |
| Ondansetron HCl | 9.30 | 9.30 | 34.8 | 9.30 | 9.30 | 34.8 |
| Hypromelose K4M premium DC | 34.30 | 34.30 | 128.4 | 30.0 | 30.0 | 112.3 |
| Sodium dihydrogen citrate anhydrous | 13.35 | 13.35 | 50.0 | 13.35 | 13.35 | 50.0 |
| Microcrystalline Cellulose type 102 (TABULOSE ®-102) | 42.52 | 42.52 | 159.2 | 46.82 | 46.82 | 175.3 |
| Magnesium stearate (Ligamed MF-2-V) | 0.53 | 0.53 | 2.0 | 0.53 | 0.53 | 2.0 |
| Total | 100.0 | 100.0 | 374.5 | 100.0 | 100.0 | 374.5 |

TABLE 23A

Core Formulation Composition of Ondansetron to be Chronodosed coated approach L004-04002 and L004

Dry Blend Formulation Prototypes Lab scale (8 mg free base), L004-04~

| Ingredient Name | 002 | | Low Hardness 002 | High Hardness 002C | 004 | | |
|---|---|---|---|---|---|---|---|
| | % (w/w) | Batch size (g) | (mg/unit) | (mg/unit) | % (w/w) | Batch size (g) | (mg/unit) |
| Ondansetron HCl | 12.44 | 12.44 | 9.95 | 9.95 | 12.44 | 12.44 | 9.95 |
| Microcrystalline Cellulose type 102 (Tabulose-102) | 87.03 | 87.03 | 69.6 | 69.6 | 39.03 | 39.03 | 31.2 |
| Lactose monohydrate 80 (TABLETOSSE ® 80) | — | — | — | — | 48.00 | 48.00 | 38.4 |
| Sodium starch glycolate (Explosol) | — | — | — | — | — | — | — |
| Magnesium stearate (Ligamed MF-2-V) | 0.53 | 0.53 | 0.4 | 0.4 | 0.53 | 0.53 | 0.4 |
| Total | 100.0 | 100.0 | 80.0 | 80.0 | 100.0 | 100.0 | 80.0 |

TABLE 23B

Core Formulation Composition of Ondansetron to be Chronodosed coated approach L006 and L008

Dry Blend Formulation Prototypes Lab scale (8 mg free base), L004-04~

| Ingredient Name | 006 | | | 008 | | |
|---|---|---|---|---|---|---|
| | % (w/w) | Batch size (g) | (mg/unit) | % (w/w) | Batch size (g) | (mg/unit) |
| Ondansetron HCl | 12.44 | 12.44 | 9.95 | 12.44 | 12.44 | 9.95 |
| Microcrystalline Cellulose type 102 (Tabulose-102) | 39.03 | 39.03 | 31.2 | 39.03 | 39.03 | 31.2 |
| Lactose monohydrate 80 (TABLETOSSE ® 80) | 44.00 | 44.00 | 35.2 | 40.00 | 40.00 | 32.0 |
| Sodium starch glycolate (Explosol) | 4.00 | 4.00 | 3.2 | 8.00 | 8.00 | 6.4 |
| Magnesium stearate (Ligamed MF-2-V) | 0.53 | 0.53 | 0.4 | 0.53 | 0.53 | 0.4 |
| Total | 100.0 | 100.0 | 80.0 | 100.0 | 100.0 | 80.0 |

Figure 7:
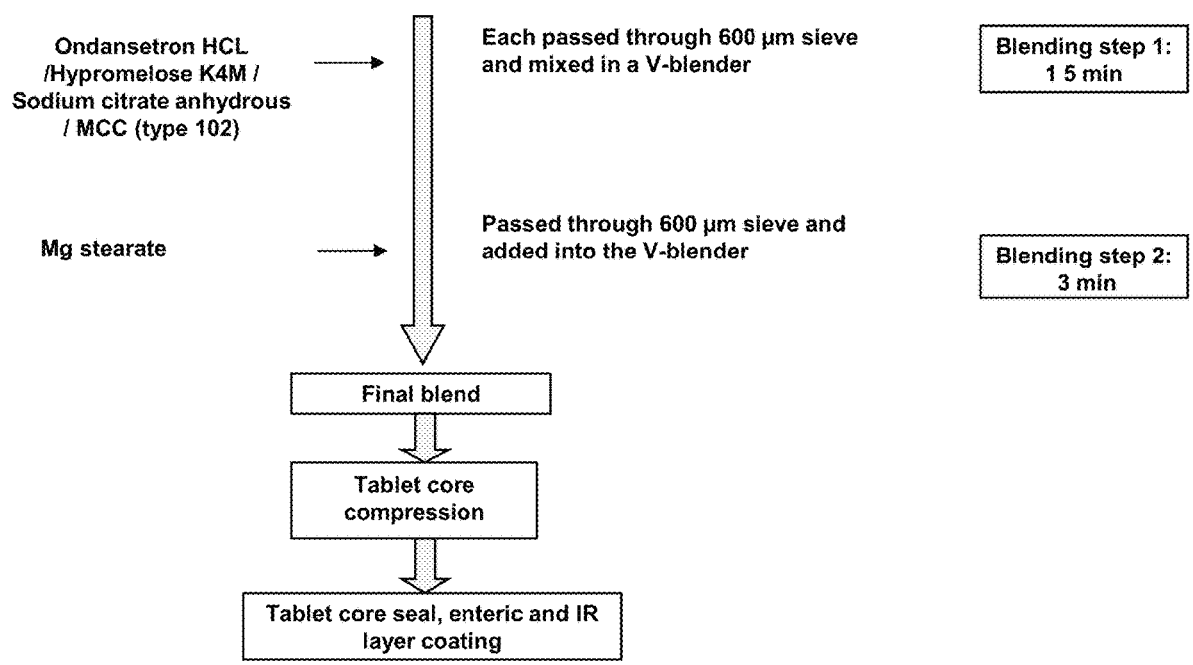
FIG. 7 shows a process flow diagram for formulating extended release ondansetron hydrochloride lot numbers L004-04001, -04003, -04005 and -04007 of an embodiment of the present disclosure.
Figure 8:
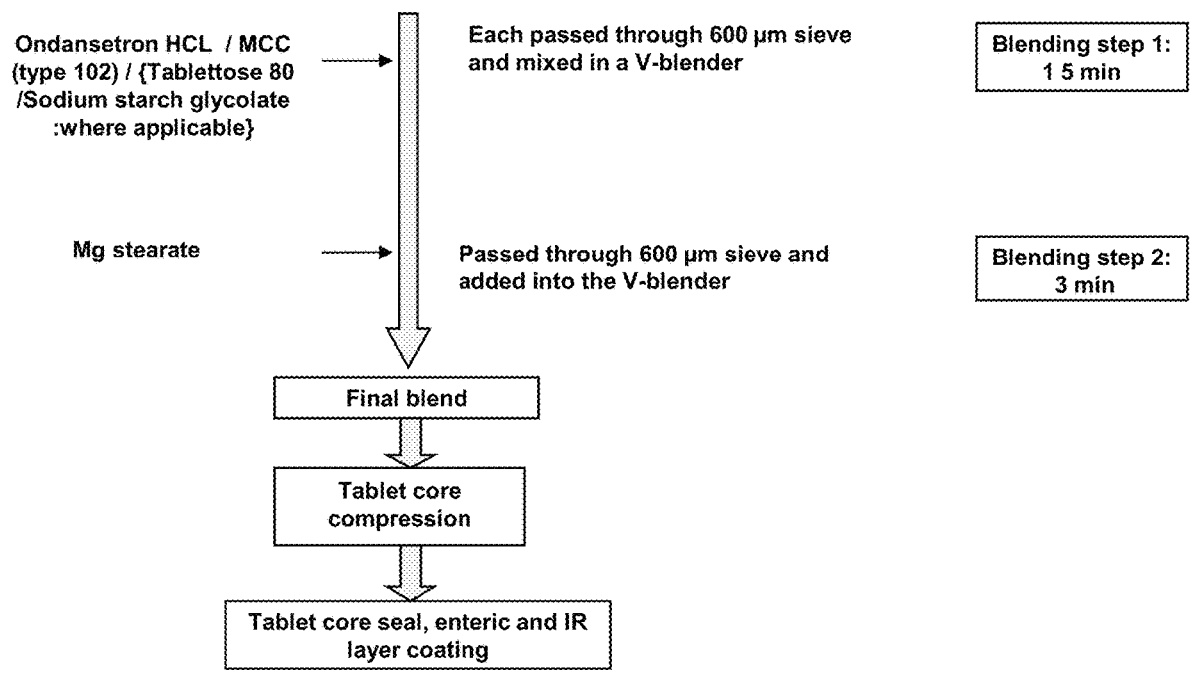
FIG. 8 shows a process flow diagram for formulating extended release chronodosed ondansetron hydrochloride lot numbers L004-04002, -04004, -04006 and -04008 of an embodiment of the present disclosure.

The extended release bimodal tablet and chronodosed formulations processes flow are presented in FIG. 7 and FIG. 8 respectively.

Example 10—Core Tablet Compression Approach Process Description

The compression trials of lots L004-0401, -04001A, -04005 and -04007 extended release formulation were performed using a hydraulic laboratory hand press with 10.0 mm diameter standard concave round tooling while the lot -04003 the compression was conducted using a 6 stations rotary tablet press machine type PR6 (SVIAC, Antony, France) equipped with a gravity powder feeder with 8.0× 16.0×2.0 deep oval concave 'D' type tooling. The core tablets -04007B were also compressed using 6 stations rotary tablet press machine type PR6 with 7.0×14.0 mm 'D' type tooling model capsule with the number "20" embedded in upper punch. The core tablets L004-04002, -04002C, -04004, -04006 and -04008 intended to be chronodosed coated were also compressed using also the SVIAC with 6.0 mm round standard concave 'D' type tooling.

Example 11—Coating for Tablets

Seal, enteric and immediate release layer coating for bimodal drug product from formulations -04001, -04003 and -04007, as well as for chronodosed film coating for drug products from formulation -04002, -04004, -04006 and -04008 were performed using an Aeromatic-Fielder fluid bed laboratory unit (model Strea-1, Columbia, Md., USA) equipped with a Wurster column. The coating suspensions were sprayed using a Cole-Parmer peristaltic pump (model 77521-40, Vernon Hills, Ill., USA) with Masterflex tubing #16.

Aqueous coating composition for the seal and enteric coat, as well as for the immediate release layer applied on sustained release enteric coated tablets can be found in Tables 24, 25 and 26 respectively. The core tablets 28 mg from the first compression trial of extended release formulation L004-04005 were not coated. They were intended to evaluate and compare the dissolution profile in pH 6.8 medium against those of -04003.

TABLE 24

Composition of All Seal Coats Aqueous Suspensions

| | | | | Total quantity prepared (g) Lot L004-04 | | | |
|---|---|---|---|---|---|---|---|
| Component | Supplier | Appearance | % w/w | 001 | 001A | 003 | 007A and 007B |
| Purified water* | Corealis Pharma | Clear liquid | 93.4 | | | 93.4 | |
| Hypromelose (METHOCEL ™ E5) | JRS Pharma | White powder | 6.0 | | | 6.0 | |
| plasACRYL ™ T20 (20%) | Evonik | White emulsion | 0.6 | | | 0.6 | |
| TOTAL | | | 100.0 | | | 100 | |

*Removed during coating and drying process

TABLE 25

Composition of All Enteric Coats Aqueous Suspensions

| | | | | Total quantity prepared (g) Lot L004-04 | | | |
|---|---|---|---|---|---|---|---|
| Component | Supplier | Appearance | % w/w | 001 | 001A | 003 | 007A and 007B |
| Purified water* | Corealis Pharma | Clear liquid | 17.02 | | | 17.02 | |
| EUDRAGIT ® L30 D55 (30%) | Evonik | White suspension | 71.22 | | | 71.22 | |
| plasACRYL ™ T20 (20%) | Evonik | White emulsion | 10.68 | | | 10.68 | |
| Triethyl Citrate | Vertellus | Clear liquid | 1.08 | | | 1.08 | |
| TOTAL | | | 100 | | | 100.0 | |

*Removed during coating and drying process

TABLE 26

Composition of All Immediate Release Layers Aqueous Suspensions

| | | | | Total quantity prepared (g) Lot L004-04 | | | |
|---|---|---|---|---|---|---|---|
| Component | Supplier | Appearance | % w/w | 001 | 001A | 003 | 007A and 007B |
| Purified water* | Corealis Pharma | Clear liquid | 93.1 | | | 186.2 | |
| Ondansetron HCl/API | HiKAL | Off white powder | 2.4 | | | 4.8 | |
| Hypromelose (METHOCEL ™ E5) | JRS Pharma | White powder | 3.6 | | | 7.2 | |

TABLE 26-continued

Composition of All Immediate Release Layers Aqueous Suspensions

| | | | | Total quantity prepared (g) Lot L004-04 | | | |
|---|---|---|---|---|---|---|---|
| Component | Supplier | Appearance | % w/w | 001 | 001A | 003 | 007A and 007B |
| plasACRYL ™ T20 (20%) | Evonik | White emulsion | 0.9 | | | | 1.8 |
| TOTAL | | | 100.0 | | | | 200.0 |

*Removed during coating and drying process

Table 27 displays different composition of diverse chronodosed aqueous coat suspension trials applied on the 8 mg core tablet. The coat suspension trials #1 and #2 were formulated without talk. Trials #3, #4, #7 and #9 included 5.88% of talk while for the trials #5 and #6, the talc ratio was reduced down to 1%.

TABLE 27

Various Compositions of Chronodose Aqueous Suspension Trials #1 to #8

| | (Eudragit RS/RL ratio) | | | | | | | |
|---|---|---|---|---|---|---|---|---|
| Component | (3-7): Trial #1 | (7-3): Trial #2 | (9-1): Trial #3 | (8-2): Trial #4 | (8-2): Trial #5 | (6-4): Trial #6 | (7-3): Trial #7 | (6-4): Trial #8 |
| | | | | % w/w | | | | |
| Purified water* | 19.4 | 19.4 | 52.55 | 52.55 | 41.12 | 41.12 | 52.55 | 52.55 |
| EUDRAGIT ® RS 30D (30%) | 24.0 | 56.0 | 35.29 | 31.38 | 44.42 | 33.32 | 27.44 | 23.53 |
| EUDRAGIT ® RL 30D (30%) | 56.0 | 24.0 | 3.93 | 7.84 | 11.11 | 22.21 | 11.78 | 15.69 |
| plasACRYL ™ T20 (20%) | 0.6 | 0.6 | — | — | — | — | — | — |
| Triethyl citrate | — | — | 2.35 | 2.35 | 2.35 | 2.35 | 2.35 | 2.35 |
| Talc | — | — | 5.88 | 5.88 | 1.00 | 1.00 | 5.88 | 5.88 |
| TOTAL | 100.0 | 100.0 | 100.0 | 100.0 | 100.0 | 100.0 | 100.0 | 100.0 |
| Total of Solids (%) | 24.12 | | | | 20.0 | | | |

Example 12—Tablets Seal Coating

Figure 9:
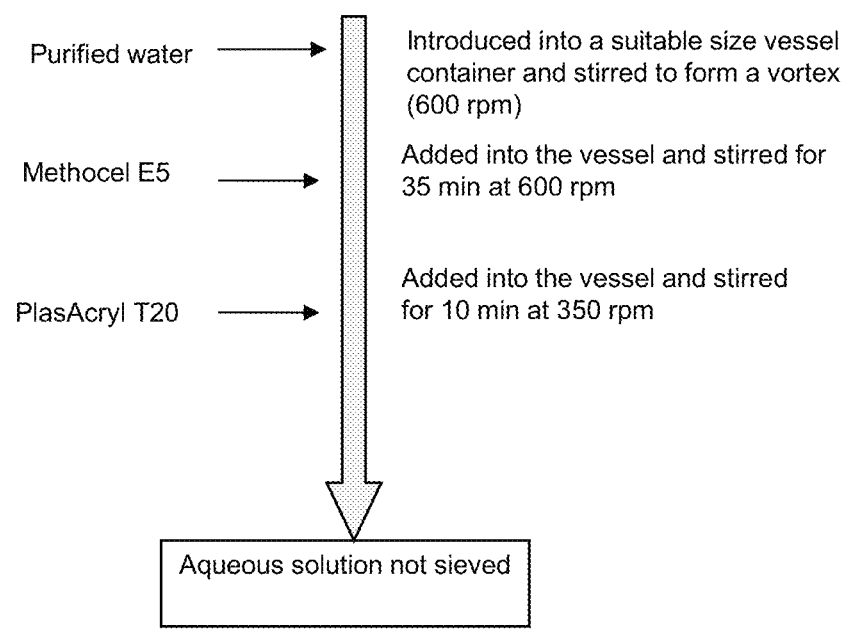
FIG. 9 shows a process flow diagram for seal coat solution preparation of an extended release dosage form of an embodiment of the present disclosure.

The seal aqueous coating solution of 6.12% w/w was manufactured by dissolving the METHOCEL™ E5 in water, then adding the plasACRYL™ using a marine propeller (≈50.0 mm of diameter) as shown in FIG. 9. Table 28 presents the seal coating process parameters. During the final drying stage, the inlet air temperature was set at 46° C.

TABLE 28

Aeromatic-Fielder fluid bed Seal Coating Process Parameters

| Lot L004-04~ | Targeted Weight Gain (% w/w) | Tablets pre warm Time (Min) | Coating Time (min) | Inlet Air T (° C.) | Outlet Air T (45 ± 5)° C.) | Spray Rate (g/min) | Atomizing Air Pressure (bar) | Air Flow (m³/h) | Tablets Drying Time (Min) |
|---|---|---|---|---|---|---|---|---|---|
| 001 | 2.5% | 2 | 17 | 59-61 | 46-50 | 2.5 | 1.2 | 115-130 | 3 |
| 001A | | | 18 | 58-61 | 50 | 2.4 | | 120-130 | |
| 003 | | | 13 | 58-61 | 48-50 | 3.4 | | 110-130 | |
| 007A | | | 16 | 58-63 | 48-51 | 2.8 | | 125-130 | |
| 007B | | | 21 | 58-60 | 49-50 | 2.2 | | 130 | |
| 009A | | | 23 | 56-58 | 48-50 | 2.3 | | 120-125 | |
| 009B | | | 22 | 58 | 48-51 | 2.4 | | 120 | |

Example 13—Tablets Enteric Coating

Figure 10:
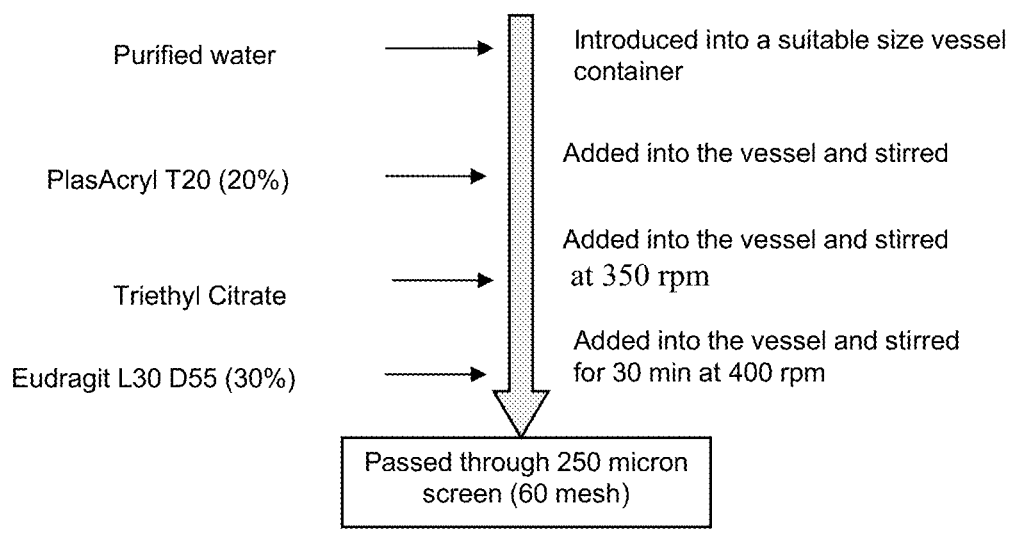
FIG. 10 shows a process flow diagram for enteric coat suspension preparation of an extended release dosage form of an embodiment of the present disclosure.

A 24.58% w/w aqueous enteric coating system was used and prepared by mixing the water, triethyl citrate and plasACRYL™ using also a marine propeller (≈50.0 mm of diameter) as shown in FIG. 10. The EUDRAGIT® dispersion was added; the suspension was mixed for 30 minutes at 400 rpm then screened through a 60 mesh screen. The enteric coating parameters are reported in Table 29. During the final drying stage, the inlet air temperature was set at 46° C.

TABLE 29

Aeromatic-Fielder fluid bed Enteric Coating Process Parameters

| Lot L004-04~ | Targeted Weight Gain (% w/w) | Tablets pre warm Time (Min) | Coating Time (min) | Inlet Air T (° C.) | Outlet Air T (41 ± 5)° C.) | Spray Rate (g/min) | Atomizing Air Pressure (bar) | Air Flow (m³/h) | Tablets Drying Time (Min) |
|---|---|---|---|---|---|---|---|---|---|
| 001 | 10% | 2 | 18 | 49-54 | 43-45 | 2.1 | 1.2 | 110-130 | 3 |
| 001A | | | 13 | 51-53 | 43-44 | 2.9 | | 125-130 | |
| 003 | | | 13 | 52-53 | 43-45 | 2.7 | | 110-120 | |
| 007A | | | 15 | 52-55 | 44-46 | 2.5 | | 120-130 | |
| 007B | | | 18 | 51-53 | 43-46 | 2.2 | | 110 | |
| 009A | | | 18 | 53-54 | 43-46 | 2.0 | | 110 | |
| 009B | | | 17 | 53 | 43-45 | 2.2 | | 110 | |

Example 14—Tablets Immediate Release Coating

Figure 11:
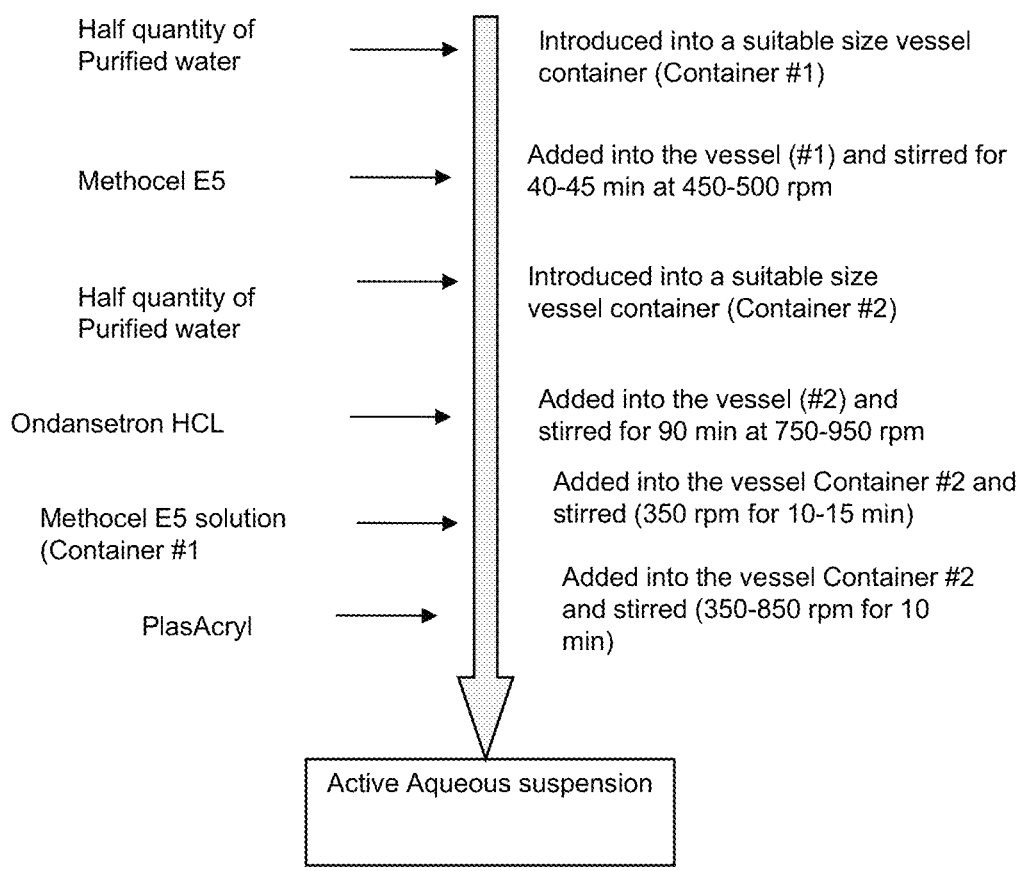
FIG. 11 shows a process flow diagram for immediate release layer suspension preparation of an extended release dosage form of an embodiment of the present disclosure.

A 6.18% w/w aqueous active suspension was prepared by first dissolving the METHOCEL™ E5 in water half of water to be used, and separately dispersing the ondansetron in water into the remaining water and stirring at high speed (750-950 rpm) using the 50.0 mm diameter marine propeller for 90 minutes. The METHOCEL™ solution was then added to the drug suspension, and finally the plasACRYL™ was added as presented in FIG. 11. The enteric coating parameters are reported in Table 30. During the final drying stage, the inlet air temperature was set at 46° C. for L001 and maintained at 56-58° C. for L001A and L003 as well as subsequent bimodal tablets formulations.

TABLE 30

Aeromatic-Fielder fluid bed Immediate Release Layer Coating Process Parameters

| Lot L004-04~ | Targeted Weight Gain (% w/w) | Tablets pre warm Time (Min) | Coating Time (min) | Inlet Air T (° C.) | Outlet Air T (43 ± 5)° C.) | Spray Rate (g/min) | Atomizing Air Pressure (bar) | Air Flow (m³/h) | Tablets Drying Time (Min) |
|---|---|---|---|---|---|---|---|---|---|
| 001 | 6.02 | 2 | 23 | 57 | 44-47 | 4.1 | 1.2 | 125-130 | 3 |
| 001A | 6.01 | | 24 | 54-56 | 45-48 | 3.9 | | 130 | 5 |
| 003 | 6.01 | | 26 | 53-58 | 44-46 | 3.6 | | 120-130 | |
| 007A | 6.02 | | 28 | 55-58 | 45-47 | 3.6 | | 120-130 | |
| 007B | 6.13 | | 36 | 54-56 | 44-46 | 2.8 | 1.2-1.3 | 110-130 | |
| 009A | 6.06 | | 37 | 58-61 | 47-48 | 2.7 | 1.3-1.4 | 120-130 | |
| 009B | 5.75 | | 33 | 58-60 | 47-48 | 3.0 | 1.4 | 80-130 | |

Example 15—Tablets Chronodosed Coating

Different chronodosed aqueous suspension compositions were tried at various tablet weight gain to evaluate how long they could delay time of drug product liberation.

Figure 12:
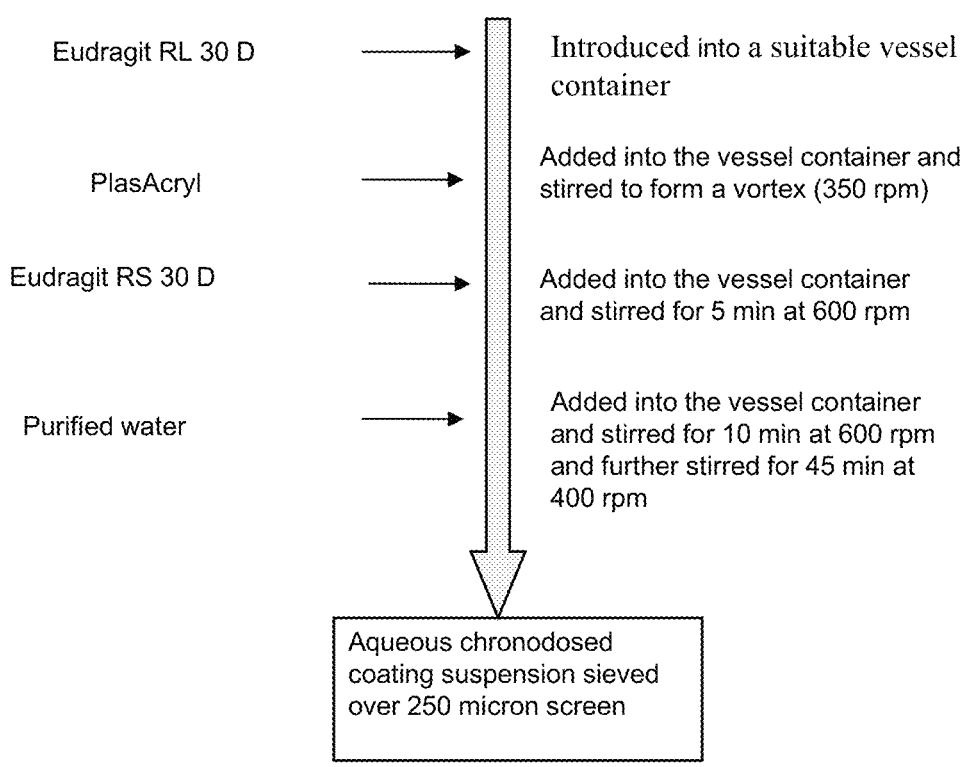
FIG. 12 shows a process flow diagram for chronodosed suspension preparation for lot numbers L004-04002A to -04002E of an embodiment of the present disclosure.

For coating chronodosed aqueous suspension compositions (24.12% w/w) used for trials #1 and #2 (FIG. 12), the EUDRAGIT® RL 30D followed by plasACRYL™ were introduced into suitable container and then mixed to form a vortex using the 50.0 mm diameter marine propeller. The EUDRAGIT® RS 30 and purified water were thereafter added sequentially and mixed before sieving over a 250 micron screen (60 mesh).

Figure 13:
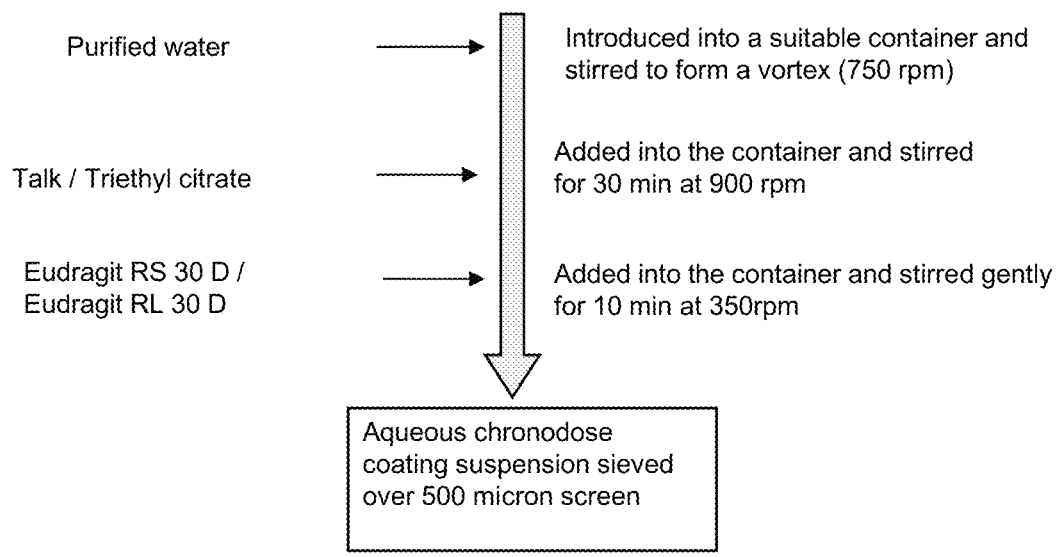
FIG. 13 shows a process flow diagram for chronodosed suspension preparation for lot numbers L004-04002F to -04002J, -04004A to -04004D, -04006A to -04006F and for -04008A and -04008B of an embodiment of the present disclosure.

For coating chronodosed aqueous suspension compositions (20.0% w/w) used for trials #3 to #8 (FIG. 13), the purified water was introduced into a suitable container and stirred using the 50.0 mm diameter marine propeller to form a vortex. The talk and triethyl citrate were then added successively and stirred. Finally, the EUDRAGIT® RS 30D and RL 30D were added and mixed before sieving over a 500 micron screen (35-mesh sieve).

From the chronodosed drug product L004-04002D to -04008B, a curing process step by spraying a few amount of purified water equivalent to around a quarter of total chronodosed aqueous suspension applied or to half (when very few quantity of chronodosed aqueous was applied) at 50° C. outlet temperature was added immediately before final drying phase as recommended by Eudragit Evonik supplier. However, for 04006E and 04008A, the curing step was not performed to evaluate the impact of curing on coated tablets.

Example 16—Chronodosed Tablets Extra Curing

The chronodosed tablets lots L004-04002D and -04002F (8 mg Ondansetron free base) were further cured without spraying water for 2 hours at 50° C. inlet air temperature to give respectively L004-04002D-2HC (2 Hours Cured) and -04002F-2HC in order to evaluate the extended cured impact on dissolution of chronodose tablets.

The dry blend DC of extended release core tablet formulation L004-04001, -04003, -04005 and -04007 were prepared with 6.64% and 9.30% of API load respectively while the chronodose core formulation -04002, -04004, -04006 and -04008 was manufactured with 12.44% of API load. All the formulations generated a high yield of 99.6% or more from laboratory batches size of 0.1 kg.

| | | Summary Chart of Lots | | | |
|---|---|---|---|---|---|
| Lot # L004- | Amount of Ondansetron HCL in core (mg) | It the core coated with a seal coat? HPMC E5/PlasAcryl T20 | Is an enteric coat present? Eudragit L30/PlasAcryl T20 | Amount of Ondansetron HCL in IR layer (mg) & seal coat HPMC E5/Plasacryl T20 | Is the core coated with Eudragit RS/RL 30 D-Plasacryl T20? (chronodosed coating) |
| 04001 | 20 | Yes | Yes | 8 | No |
| 04001A | 20 | Yes | Yes | 8 | No |
| 04003 | 28 | Yes | Yes | 8 | No |
| 04005 | 28 | No | No | 0 - No IR layer | No |
| 04007 | 28 | Yes | Yes | 8 | No |
| 04007A | 28 | Yes | Yes | 8 | No |
| 04007B | 28 | Yes | Yes | 8 | No |
| 04009A | 28 | Yes | Yes | 8 | No |
| 04009B | 28 | Yes | Yes | 8 | No |
| 04002A | 8 | | | 0 - No IR layer | Yes |
| 04002B | 8 | | | 0 - No IR layer | Yes |
| 04002C | 8 | | | 0 - No IR layer | Yes |
| 04002D | 8 | | | 0 - No IR layer | Yes |
| 04002E | 8 | | | 0 - No IR layer | Yes |
| 04002F | 8 | | | 0 - No IR layer | Yes |
| 04002G | 8 | | | 0 - No IR layer | Yes |
| 04002H | 8 | | | 0 - No IR layer | Yes |
| 04002I | 8 | | | 0 - No IR layer | Yes |
| 04002J | 8 | | | 0 - No IR layer | Yes |
| 04004A | 8 | | | 0 - No IR layer | Yes |
| 04004B | 8 | | | 0 - No IR layer | Yes |
| 04004C | 8 | | | 0 - No IR layer | Yes |
| 04004D | 8 | | | 0 - No IR layer | Yes |
| 04006A | 8 | | | 0 - No IR layer | Yes |
| 04006B | 8 | | | 0 - No IR layer | Yes |
| 04006C | 8 | | | 0 - No IR layer | Yes |
| 04006D | 8 | | | 0 - No IR layer | Yes |
| 04006E | 8 | | | 0 - No IR layer | Yes |
| 04006F | 8 | | | 0 - No IR layer | Yes |
| 04008A | 8 | | | 0 - No IR layer | Yes |
| 04008B | 8 | | | 0 - No IR layer | Yes |

Example 17—In-Vitro Dissolution Profiles

Figure 14:
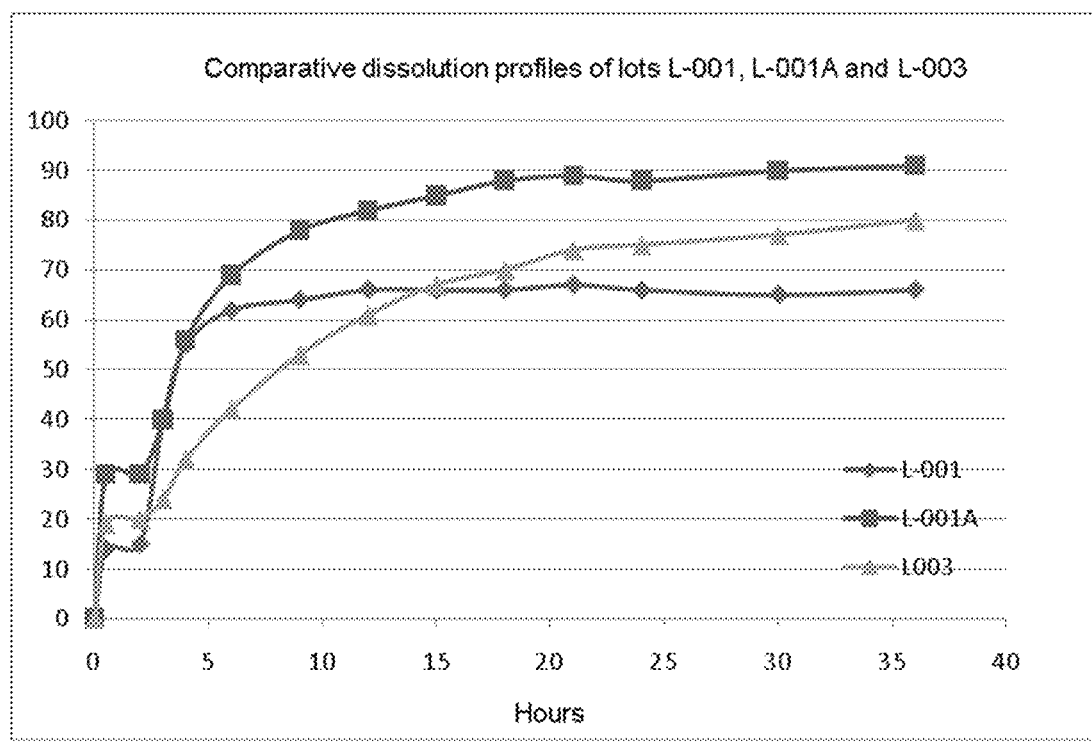
FIG. 14 illustrates the dissolution profiles for ondansetron bimodal tablets, 28 mg -04001 and -04001A, and ondansetron bimodal tablets 36 mg -04003.

FIG. 14 presents comparison dissolution profiles of Ondansetron bimodal round convex 28 mg tablets lots -04001 and -04001A compressed at low and high hardness respectively, and the oval convex tablets 36 mg lot -04003. The bimodal 36 mg tablet -04003 with 41.30% of Hypromellose K4M (sustained release agent) gave 80% dissolution at the 36$^{th}$ hour.

Figure 15:
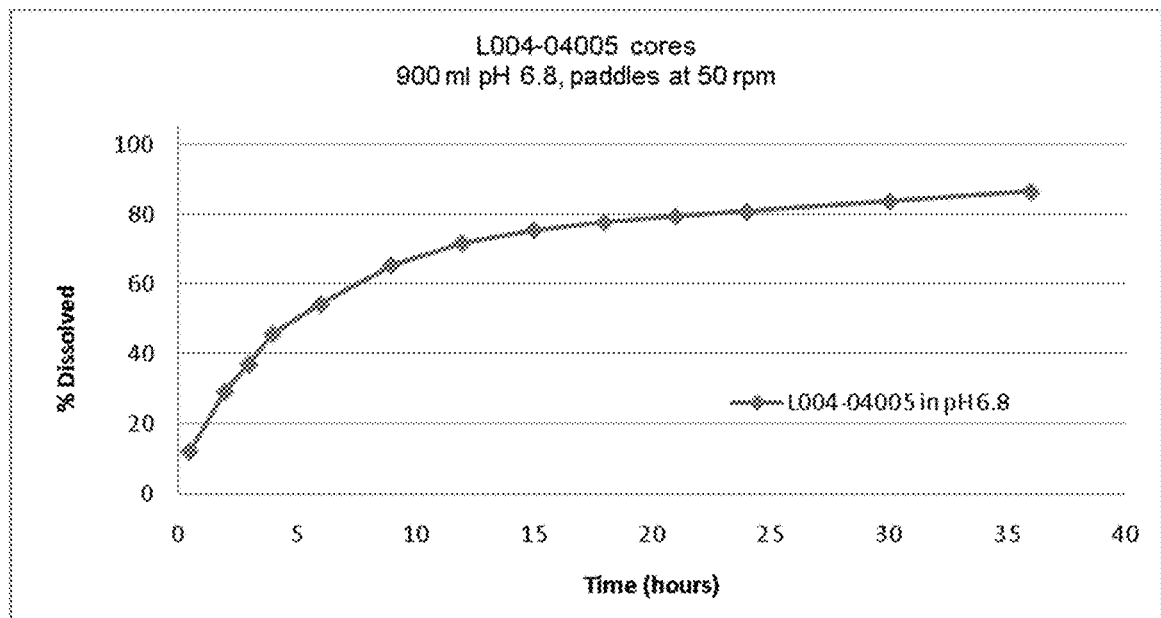
FIG. 15 illustrates the dissolution profile for ondansetron core tablets 28 mg -04005.
Figure 16:
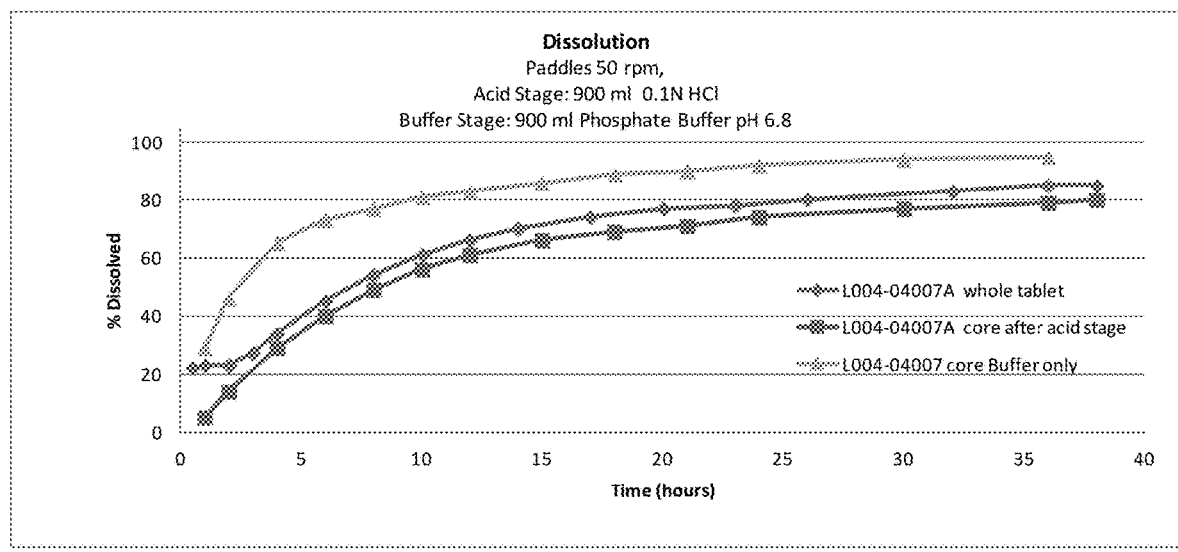
FIG. 16 illustrates the dissolution profiles for ondansetron core tablet -04007 28 mg and ondansetron bimodal tablets 36 mg -04007A.

The core 28 mg tablet -04005 with reduced sustained release agent down to 34.30% gave 87% dissolution at the 36$^{th}$ hour (FIG. 15). Lots -04007A and -04007B (FIGS. 16 and 17) were formulated with 30.0% of Hypromellose (sustained release agent). FIG. 16 presents comparison dissolution profiles of Ondansetron core tablets -04007 28 mg and bimodal -04007A. It appeared that the coating had a real impact on dissolution profiles and reduction of enteric coating weight gain should be tested.

Figure 17:
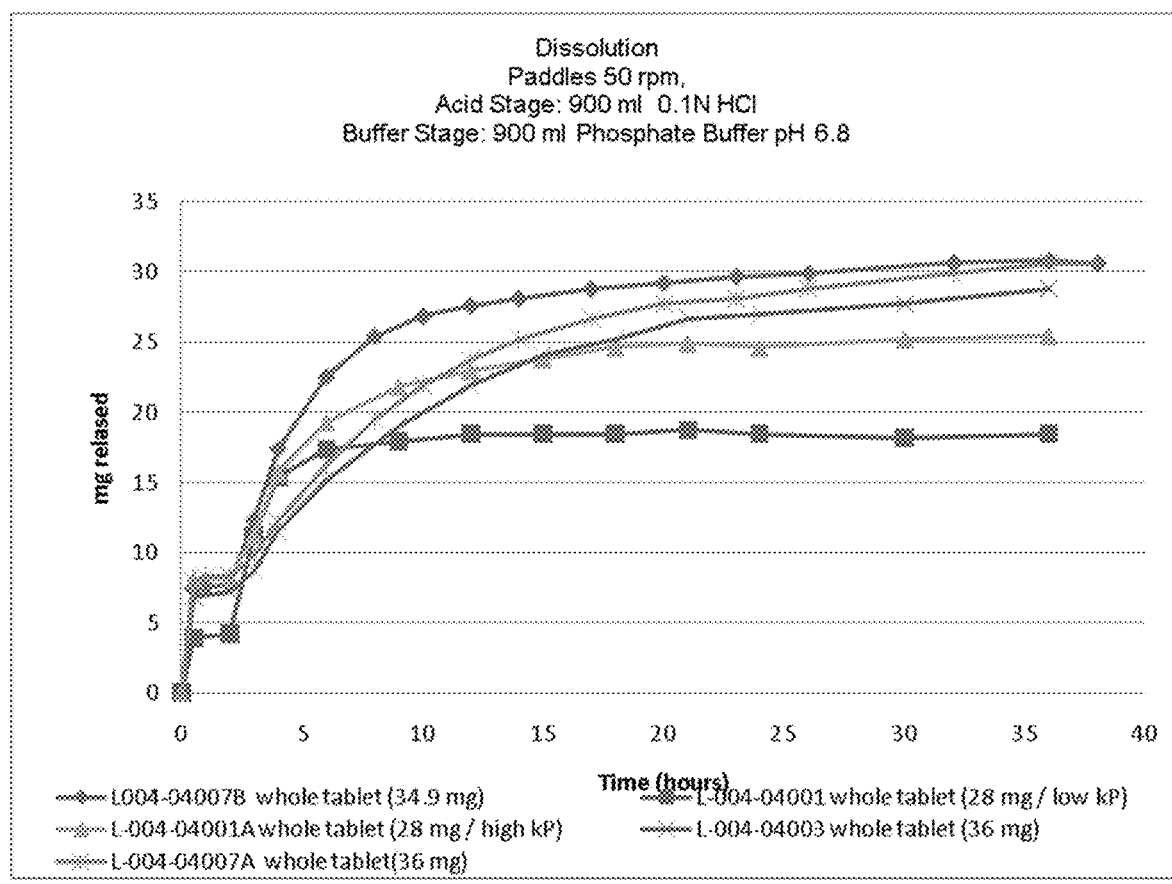
FIG. 17 illustrates the dissolution profiles (in mg) for ondansetron bimodal tablets, 28 mg -04001 and -04001A, and ondansetron bimodal tablets 36 mg -04003, -04007A and -04007B.

FIG. 17 presents comparison dissolution profiles in mg of Ondansetron bimodal from formulations -04001, -04003, and -04007. Drug products -04001, -04001A and -04007A were compressed with 10.0 mm round convex standard toolings while the lot -04003 was compressed with Oval, concave, (8.0×16.0×2.0 mm) and the lot -04007B with Oblong, Capsule, (7.0×14.0 mm upper Emb. "20").

At the 36 hours of dissolution time, lots -04007A (24.4 kP hardness value) and -04007B (20.2 kP hardness value) showed the highest API mg dissolved slightly over 30 mg out of 36 mg expected. However, lot -04007B showed faster dissolution profile compared to that of -04007A.

Figure 18:
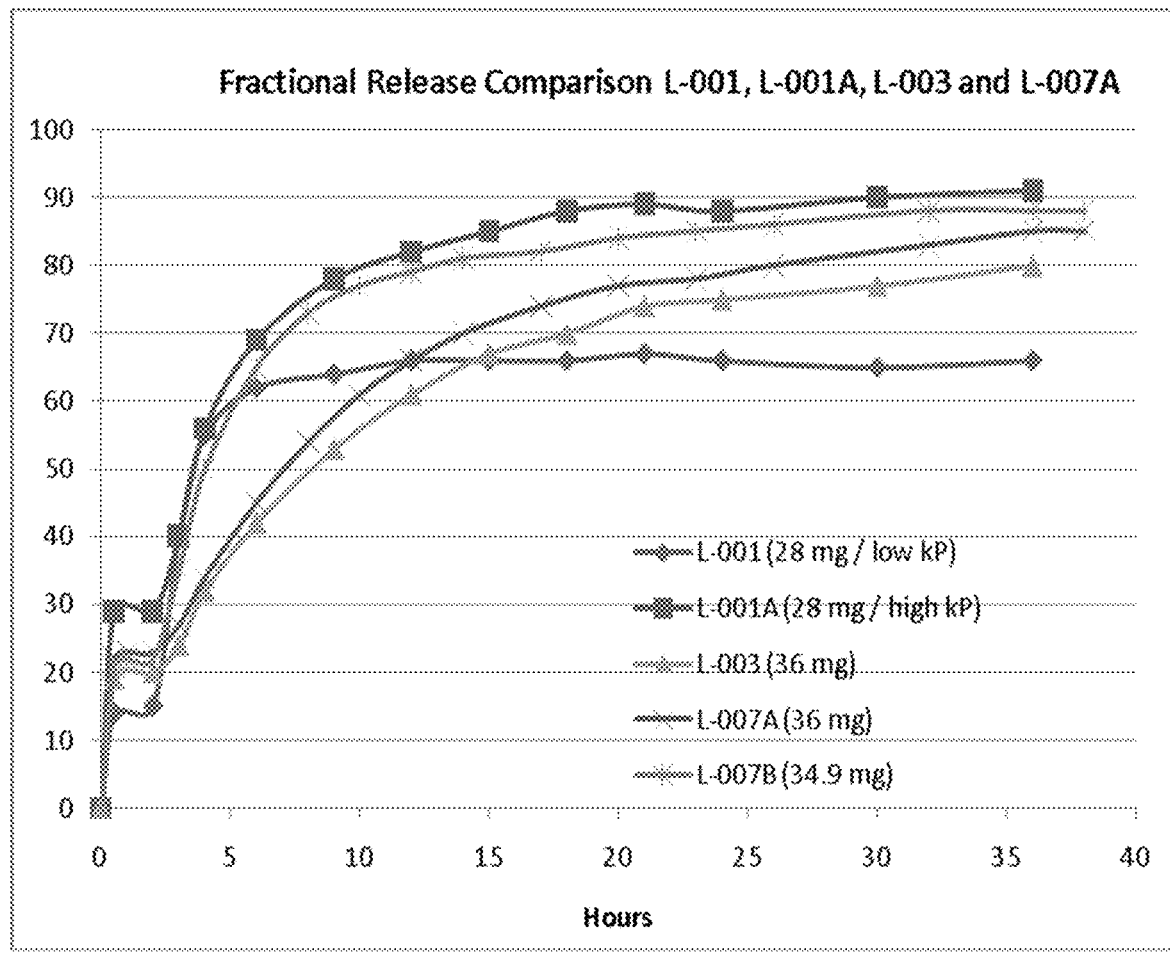
FIG. 18 illustrates the dissolution profiles (in %) for ondansetron bimodal tablets, 28 mg -04001 and -04001A, and ondansetron bimodal tablets 36 mg -04003, -04007A and -04007B.

FIG. 18 presents comparison dissolution profiles in percentage of Ondansetron bimodal from formulations showed above in FIG. 17 with corrected values of the expected results taking into consideration the actual average core tablet weight of 360.0 mg.

Lot -04009A (with 12.6 kP hardness value) and 04009B (16.7 kP hardness value) were compressed using oval concave new toolings (7.6×14.0 mm) with an average core tablet weight of 376.40 mg and to 386.87 mg respectively. For a hardness difference of only around 4 kP, the compression force increased five times from 400 Kgf to 2200 Kgf for lots 04009A and 04009B, respectively, suggesting a plastic deformation of the tablet core at higher hardness that could explain the faster release. FIG. 16 presents the dissolution profiles in mg/time of the bimodal drug products 04003, 04007A, 04007B, 04009A and 04009B. More than 32 mg out of 36 mg expected were recovered from bimodal tablet 04009B, slightly better than the lot 04007B but a little bit faster. FIG. 17 shows same results in percentage dissolved.

| | Sample | | | | | |
|---|---|---|---|---|---|---|
| | L004-04009A | | | L004-04009B | | |
| | Dose | | | | | |
| | Coating 8 mg Core 28 mg | | | Coating 8 mg Core 28 mg | | |
| Dissolution Paddles 50 rpm Acid Stage: 900 ml 0.1N | Time (hrs) | % LC coating and % LC for core | % LC for whole tablet | Time (hrs) | % LC coating and % LC for core | % LC for whole tablet |

-continued

| | Sample | | | | |
|---|---|---|---|---|---|
| | L004-04009A | | | L004-04009B | |
| | Dose | | | | |
| | Coating 8 mg Core 28 mg | | | Coating 8 mg Core 28 mg | |
| HCl for | Acid Stage | | | Acid Stage | |
| 2 hours | 0.5 | 93 | 21 | 0.5 | 110 | 24 |
| Buffer Stage: | 1 | 94 | 21 | 1 | 112 | 25 |
| 900 ml | 2 | 95 | 21 | 2 | 113 | 25 |
| Phosphate | Buffer Stage | | | Buffer Stage | |
| Buffer | 3 | 16 | 34 | 3 | 18 | 39 |
| pH 6.8 to 36 | 4 | 30 | 45 | 4 | 36 | 53 |
| hours (n = 3) | 6 | 48 | 58 | 6 | 54 | 67 |
| | 8 | 59 | 67 | 8 | 65 | 76 |
| | 10 | 65 | 72 | 10 | 72 | 81 |
| | 12 | 69 | 74 | 12 | 75 | 83 |
| | 14 | 71 | 76 | 14 | 77 | 85 |
| | 17 | 74 | 79 | 17 | 78 | 86 |
| | 20 | 74 | 79 | 20 | 79 | 87 |
| | 23 | 75 | 79 | 23 | 80 | 87 |
| | 26 | 76 | 80 | 26 | 81 | 88 |
| | 32 | 78 | 82 | 32 | 83 | 90 |
| | 36 | 78 | 82 | 36 | 83 | 90 |
| | 38 | 78 | 82 | 38 | 83 | 90 |

Figure 19:
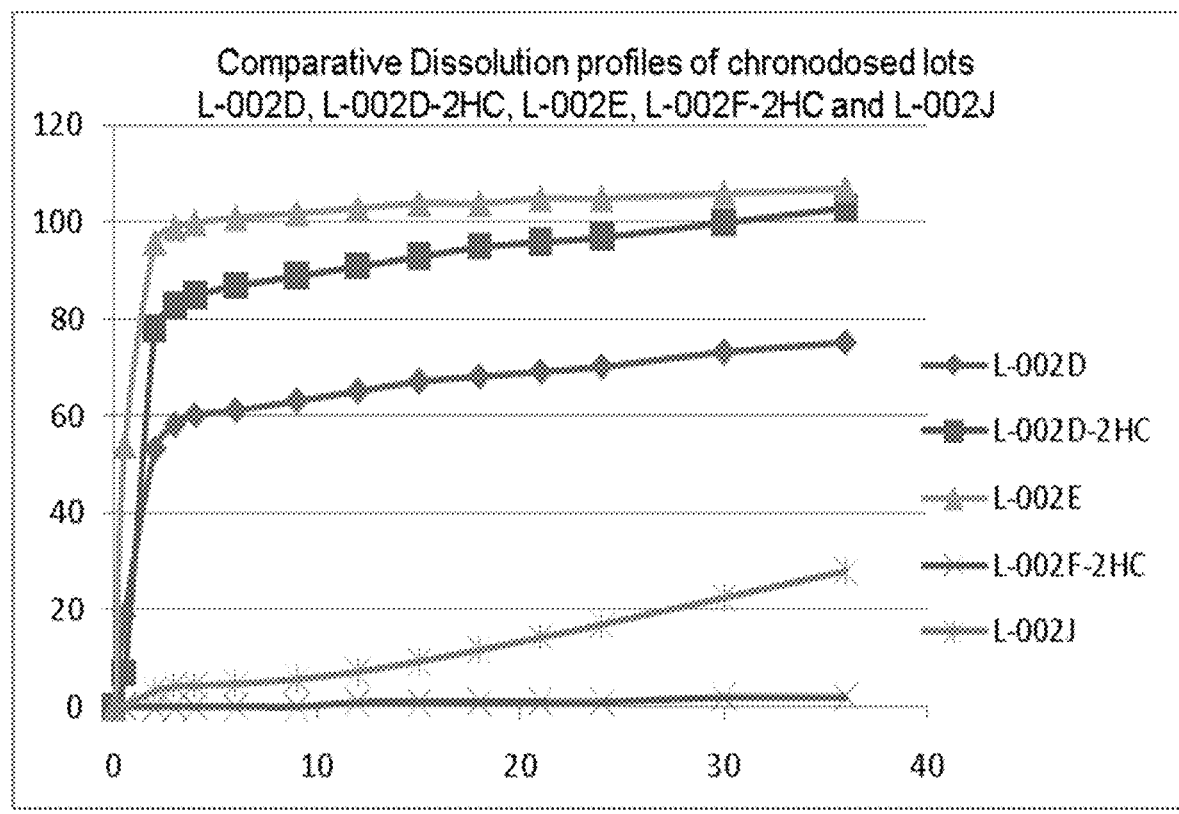
FIG. 19 illustrates the dissolution profiles for chrono-dosed ondansetron tablets, 8 mg -04002D, -04002D-042HC, -04002E, -04002F-042HC and -04002J.

FIG. 19 presents comparison dissolution profiles of chronodosed round convex tablets, 8 mg -04002D and -04002D-2HC using coating composition trial #1 (EUDRAGIT® RS/RL ratio: 3-7); -04002E using coating composition trial #2 (EUDRAGIT® RS/RL ratio: 7-3), -04002F using coating composition trial #3 (EUDRAGIT® RS/RL ratio: 9-1) and L-002J using coating composition trial #4 (EUDRAGIT® RS/RL ratio: 8-2). The formulation -04002 was formulated with only MCC-102 as filler and showed a core disintegration time over 15 minutes.

The chronodosed coat compositions trials #1 and #2 without talk failed to hold back the dissolution during the 2 hours of acid stage. Contrary to what was expected, an extra curing of two hours for -04002D-04002HC did not improve the acid stage resistance. However, the 2 hour-cured -04002F-04002HC using coating composition trial #3 containing 5.9% of talk (EUDRAGIT® RS/RL ratio: 9-1) was still intact after 36 hours releasing around 1% only. The lot -04002J chronodose coated with 4.9% weight gain using coating composition trial #4 (EUDRAGIT® RS/RL ratio: 8-2 with 5.9% showed very slight release of API over 36 hours.

Figure 20:
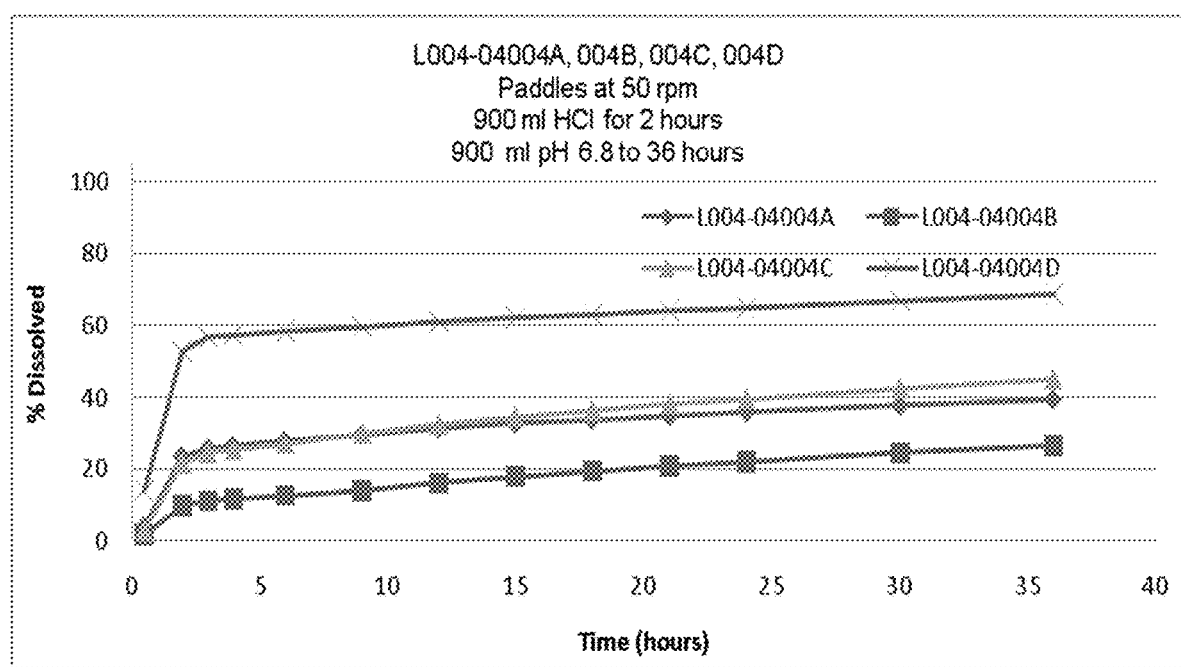
FIG. 20 illustrates the dissolution profiles for chrono-dosed ondansetron tablets, 8 mg -04004A to -04004D.

FIG. 20 displays comparison dissolution profiles of chronodosed round convex tablets, 8 mg from formulation -04004 prepared with MCC-102 and Tablettose 80 with a core disintegration time less than 8 minutes. The lots -04004A and -04004B were chronodose coated using coating composition trial #5 (EUDRAGIT® RS/RL ratio: 8-2 and 1% of talk) for a weight gain of 4.9 and 11.0% respectively while the lots -04004C and -04004D were coated using coating composition trial #6 (EUDRAGIT® RS/RL ratio: 6-4 with 1% of talk) with a weight gain of 4.9 and 10.1%. All the four lots showed a fast dissolution profiles during the first 3 hours but failed to release more than 75% over 36 hours. For an unknown reason, the lot -04004D with double weight gain compared to the lot -04004C showed faster dissolution profile.

Figure 21:
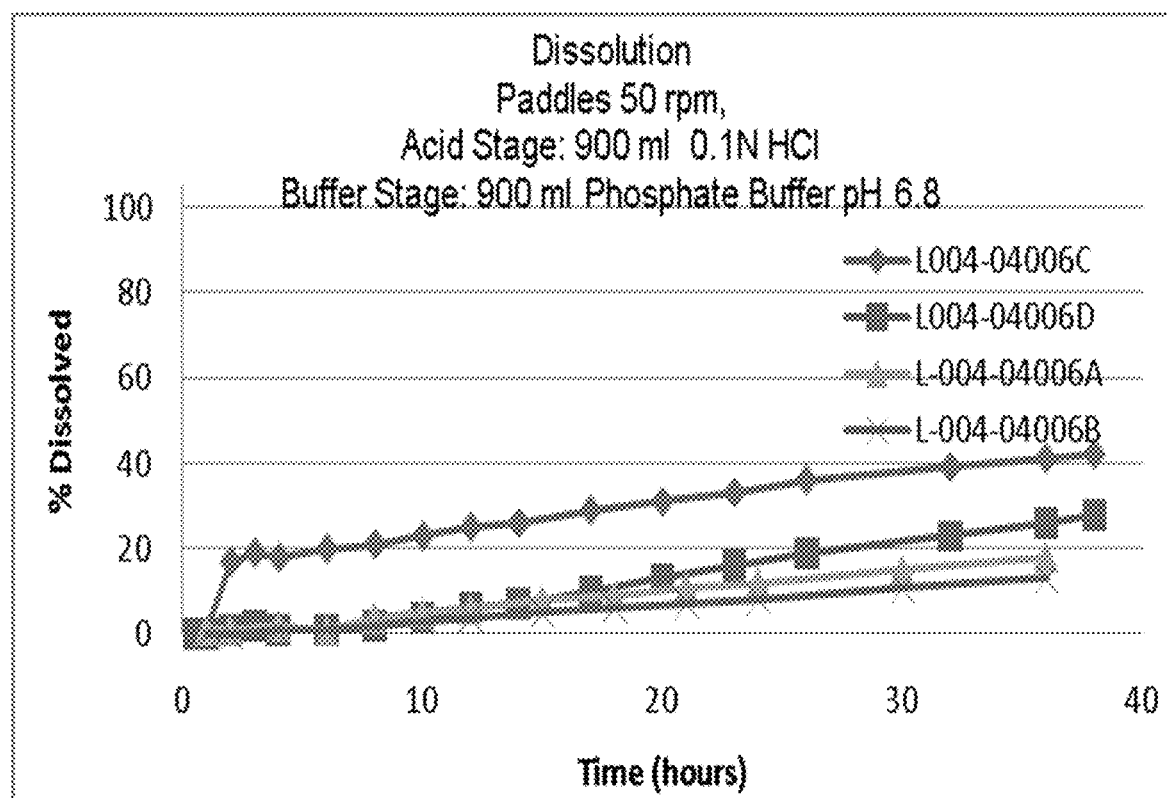
FIG. 21 illustrates the dissolution profiles for chrono-dosed ondansetron tablets, 8 mg -04006A to -04006D.

FIG. 21 displays comparison dissolution profiles of chronodosed round convex tablets, 8 mg from formulation -04006 prepared with MCC-102, TABLETOSSE® 80 and 4% of sodium starch glycolate as disintegrant and whose core disintegration time was less than 2 minutes. The lots -04006A and -04006B were chronodose coated using coating composition trial #4 as per -04002J, (EUDRAGIT® RS/RL ratio: 8-2 and 5.9% of talk) for a weight gain of 4.8 and 9.8% respectively while the lots -04006C and -04006D were coated using coating composition trial #7 (EUDRAGIT® RS/RL ratio: 7-3 with 5.9% of talk) with a weight gain of 4.9 and 9.8%. The maximum API released over 36 hours was 40% for -04006C.

Figure 22:
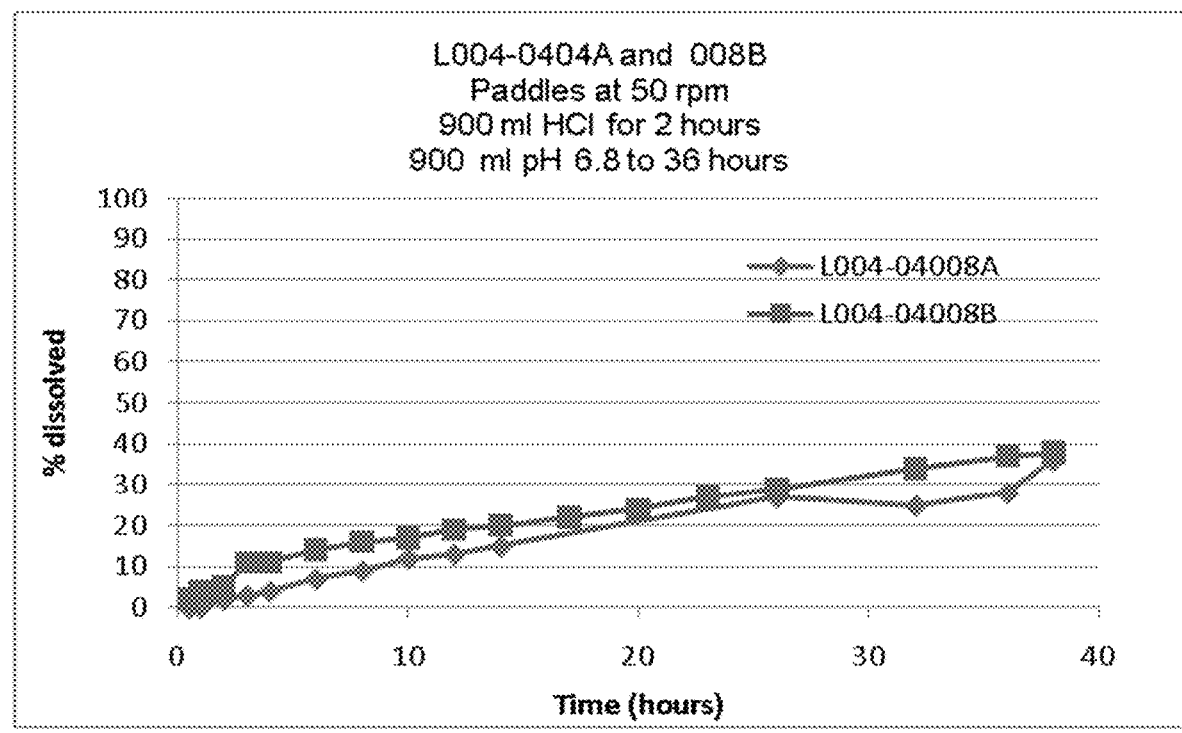
FIG. 22 illustrates the dissolution profiles for chrono-dosed ondansetron tablets, 8 mg -04008A to -04008B.
Figure 23:
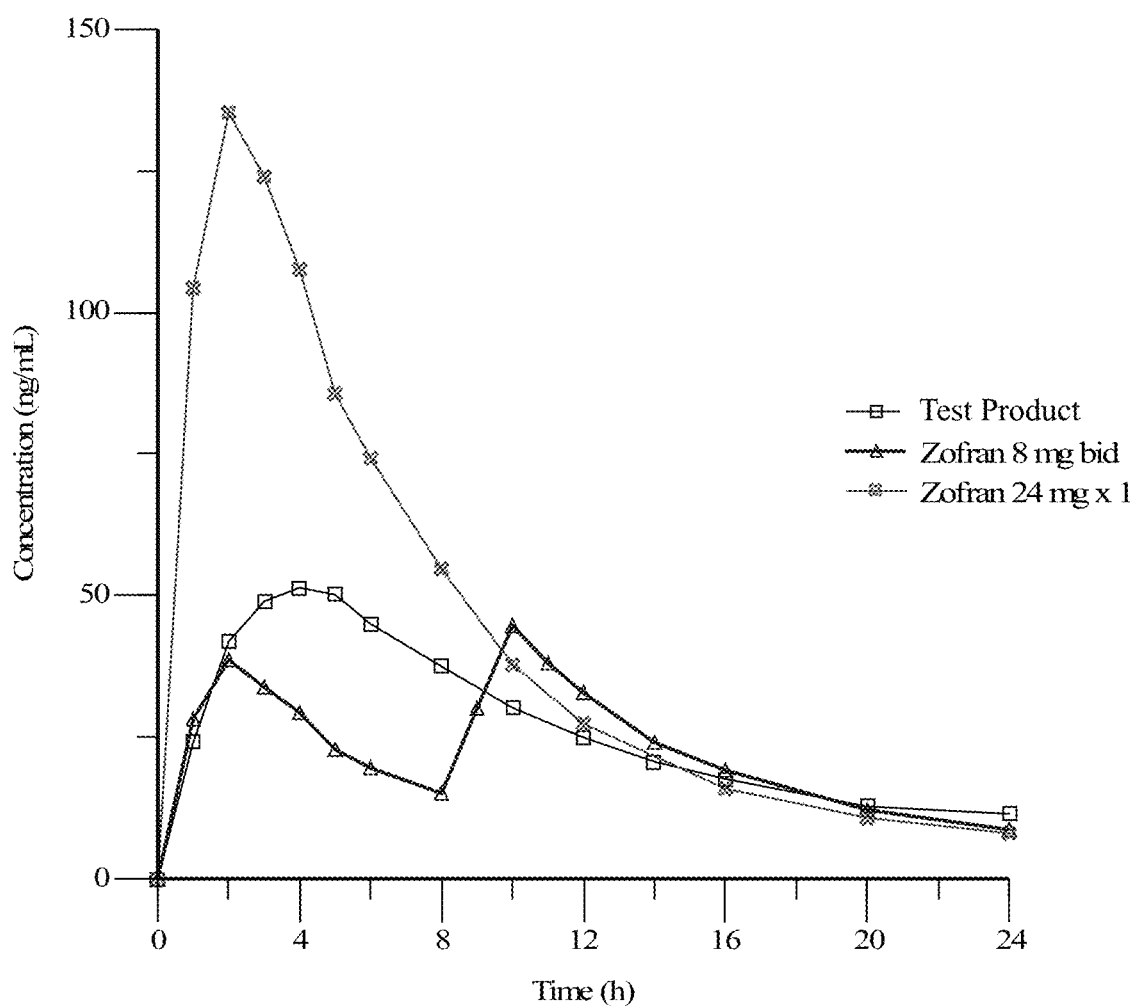
FIG. 23 illustrates the linear mean measured plasma concentration versus time profile of Test Product at day 1, derived from the administration of an embodiment of an extended release solid dosage form of the present disclosure and a reference product.
Figure 24:
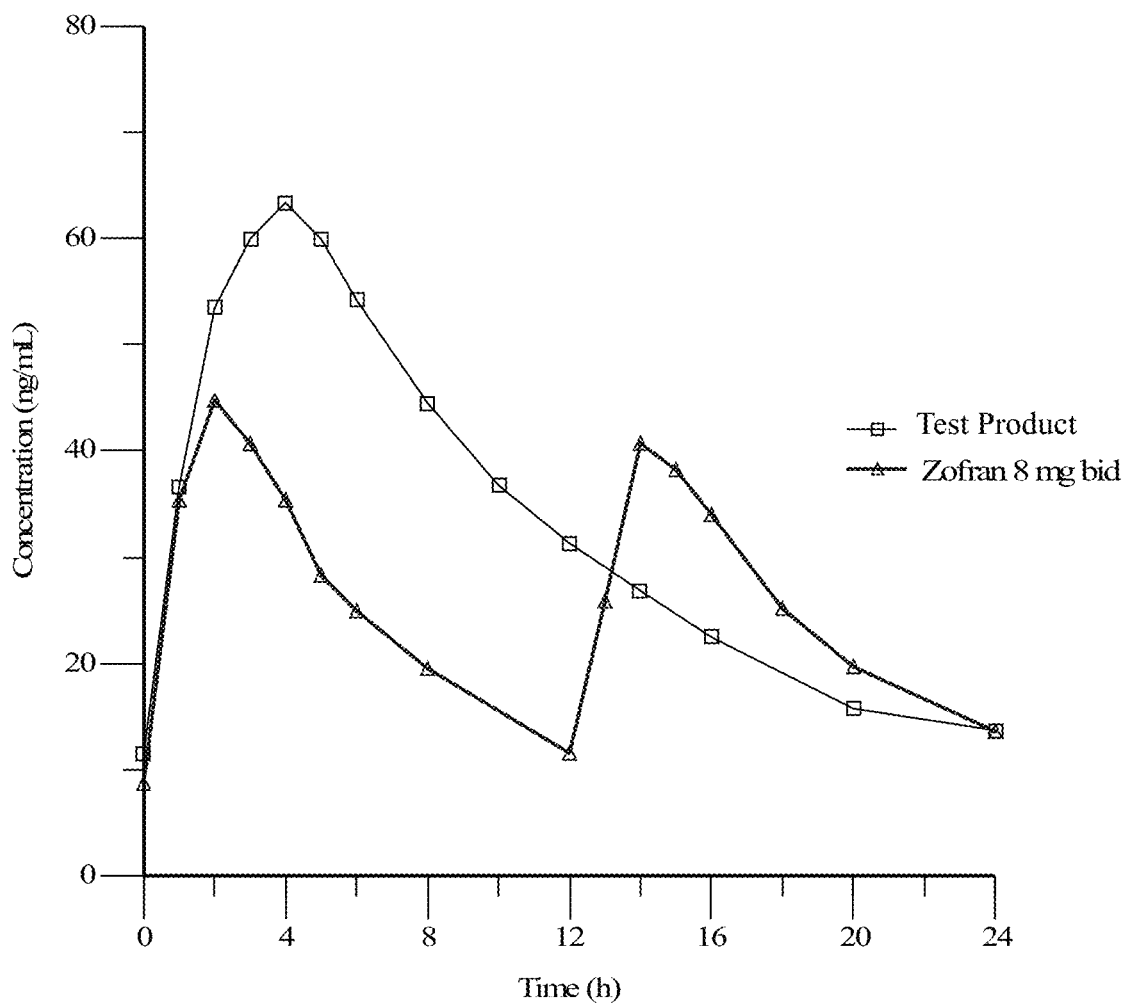
FIG. 24 illustrates the linear mean measured plasma concentration versus time profile of Test Product at day 2, derived from the administration of an embodiment of an extended release solid dosage form of the present disclosure and a reference product.
Figure 25:
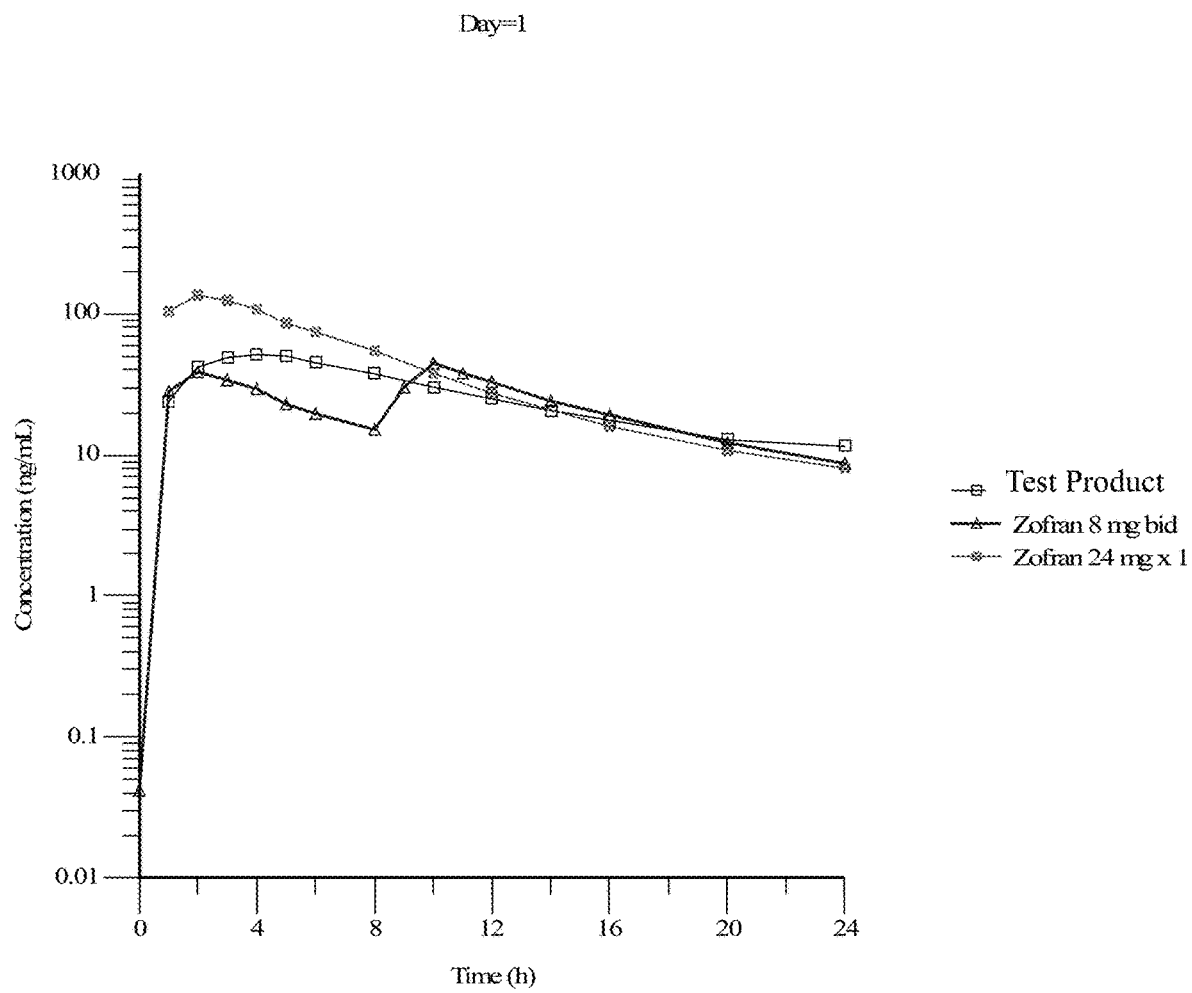
FIG. 25 illustrates the ln-transformed mean concentration versus time profile of Test Product at day 1, derived from the administration of an embodiment of an extended release solid dosage form of the present disclosure and a reference product.
Figure 26:
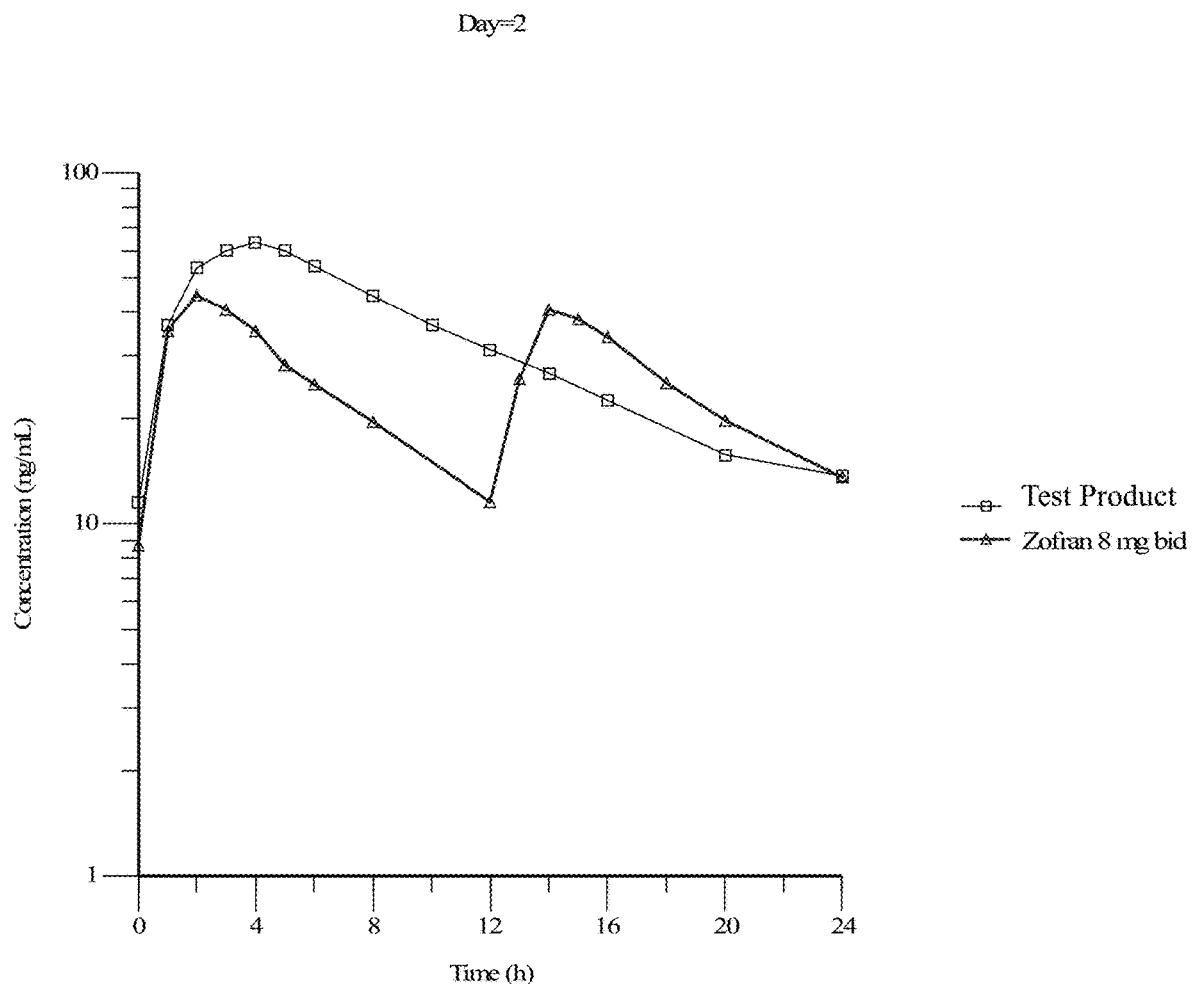
FIG. 26 illustrates the ln-transformed mean concentration versus time profile of Test Product at day 2, derived from the administration of an embodiment of an extended release solid dosage form of the present disclosure and a reference product.
Figure 27:
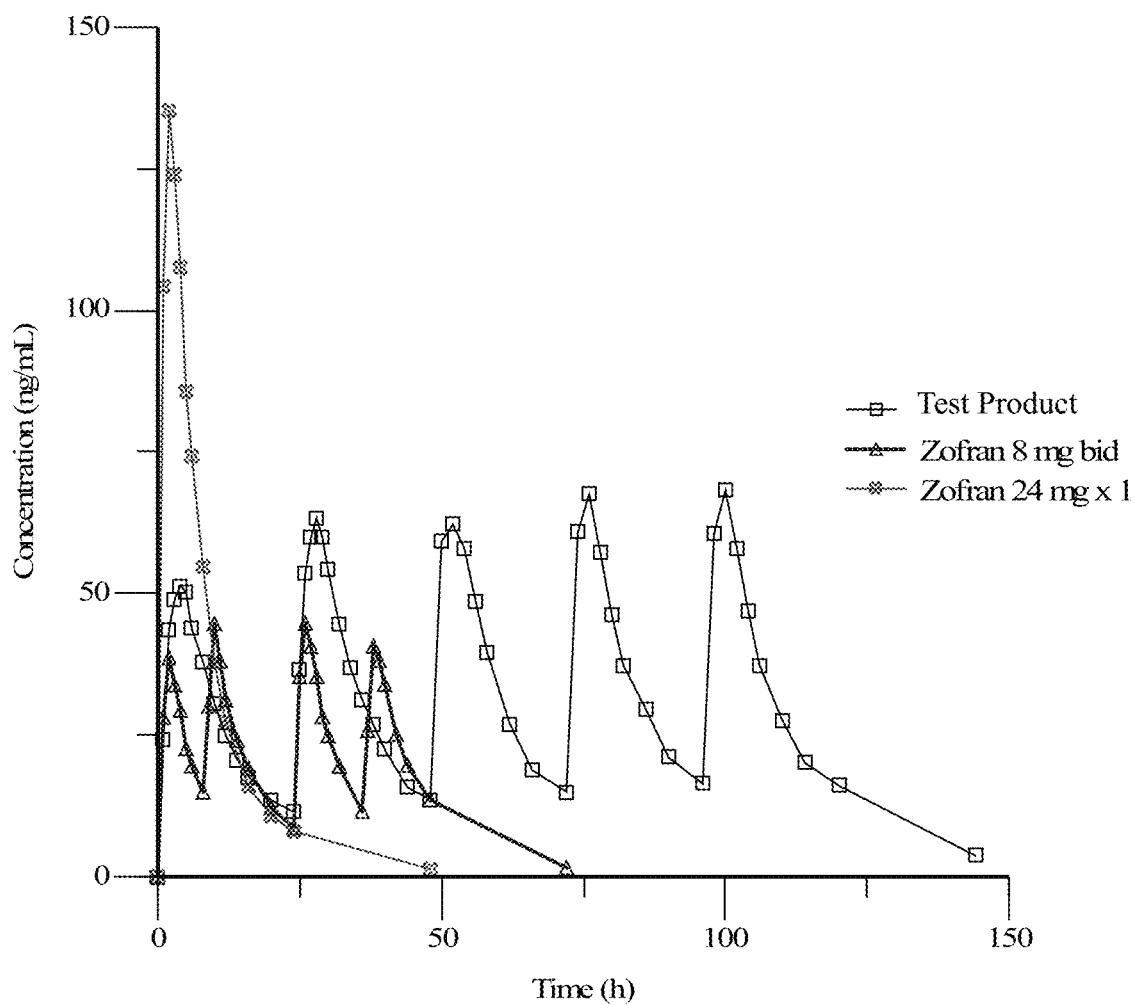
FIG. 27 illustrates the linear overall profile of the mean measured plasma concentration versus time profile of Test Product and reference product, derived from the administration of an embodiment of an extended release solid dosage form of the present disclosure and the reference product.
Figure 28:
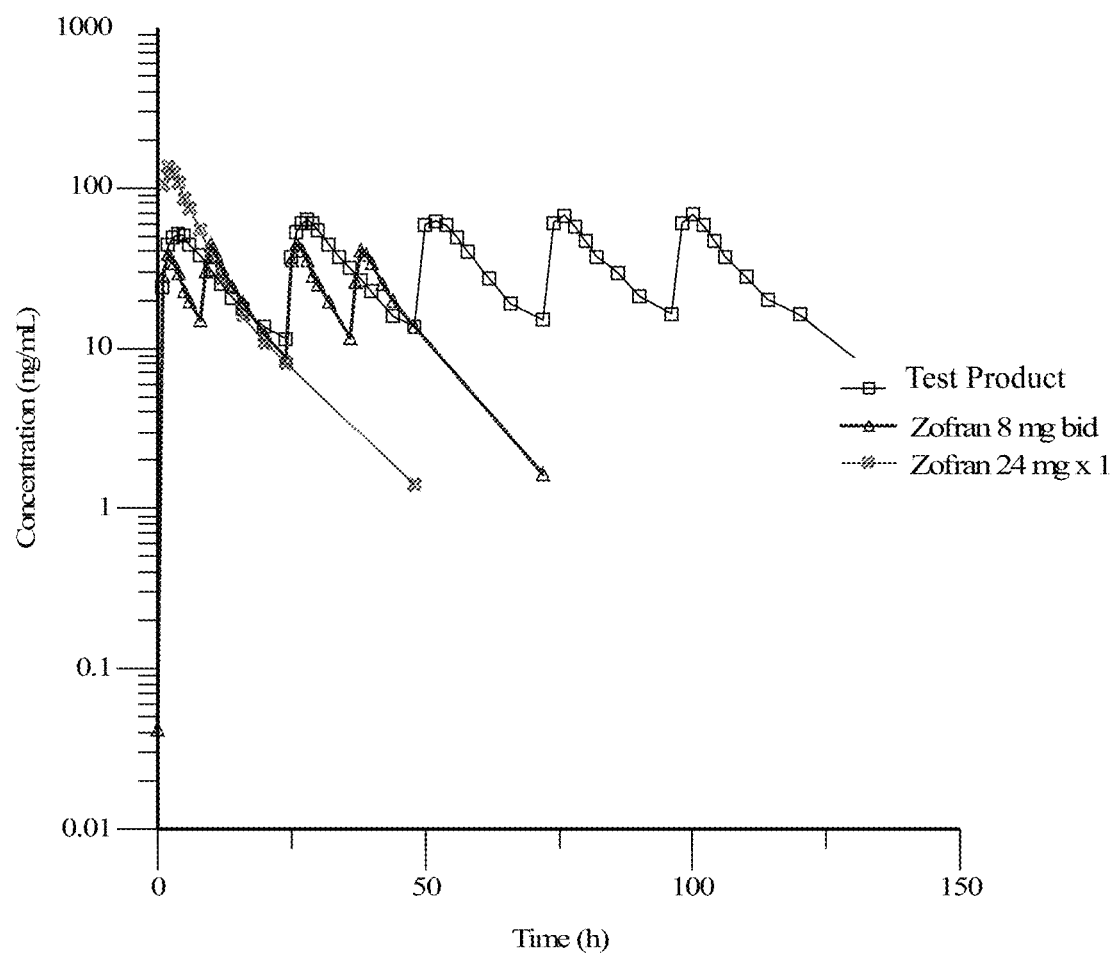
FIG. 28 illustrates the ln-transformed overall profile of the mean measured plasma concentration versus time profile of Test Product and reference product, derived from the administration of an embodiment of an extended release solid dosage form of the present disclosure and the reference product.

FIG. 22 displays comparison dissolution profiles of chronodosed round convex tablets, 8 mg from formulation -04008 prepared same excipient as per L-006 but with increased sodium starch glycolate up to 8% and for which the core disintegration time was less than 1 minutes.

The lots -04008A and -04008B were chronodose coated using coating composition trial #8 (EUDRAGIT® RS/RL ratio: 6-4 and 5.9% of talk) for a weight gain of 10.1%. The only difference between both lots in formulation process was that the lot L-008A was not cured after chronodose film coating. The dissolution profiles of both lots were almost similar. When compared to the of L-006D (with similar weight gain but coated using coating composition trial #7 (EUDRAGIT® RS/RL ratio: 7-3 and 5.9% of talk), dissolution profile improved but still not reached over 40% over 36 hours.

Example 18—3-Arm Crossover Comparative Bioavailability Study of Solid Dosage Forms 3-arm crossover comparative bioavailability study of five day dosing of solid dosage forms of the present invention once daily versus two day dosing of twice daily ondansetron 8 mg immediate-release tablets versus a single dose of ondansetron 24 mg immediate-release tablets in Healthy Male and Female Volunteers/Fasting State.

Objectives:
The primary objective of this study was to compare the relative bioavailability and peak and trough concentrations between two FDA approved regimens of commercially available ondansetron 8 mg immediate-release tablet (twice daily Zofran® 8 mg regimen administered for two days and a single dose of Zofran® 24 mg regimen administered as three Zofran® 8 mg tablets taken together) and the Test Product of ondansetron 24 mg extended-release tablet of the present invention (administered once daily).

Secondary objectives of the study were:
1. To assess the accumulation of ondansetron in the plasma after dosing with the Test Product for five consecutive daily doses, under fasting conditions
2. To assess the safety and tolerability of the extended-release formulation on healthy volunteers.

Methodology:
Single center, randomized, open-label, 3-period, 3-sequence, crossover design.

Number of Subjects (Planned and Analyzed):
Planned for inclusion: 18
Included: 18
Drop-outs: 0
Analyzed: 18
Considered in the pharmacokinetic and statistical analysis: 18
Considered in the safety analysis: 18

Diagnosis and Main Criteria of Inclusion:
Male and female volunteers, non- or ex-smokers, of at least 18 years of age with a body mass index greater than or equal to 18.50 and below 30.00 kg/m² were included in the study. Subjects were in good health as determined by a medical history, complete physical examination (including vital signs), 12-lead Electrocardiogram (ECG) and the usual clinical laboratory tests (general biochemistry, hematology, urinalysis) including negative Human Immunodeficiency Virus (HIV), Hepatitis B and Hepatitis C tests as well as negative urine drug screening of alcohol, cotinine and drugs of abuse and negative beta Human Chorionic Gonadotropin (HCG) qualitative serum pregnancy test (for female subjects).

Test Product, Dose and Mode of Administration:
Name: Ondansetron
Dosage form/Route of administration: A bimodal tablet of the present invention (Electrolyte CDT Core)/Oral ("Test Product")
Regimen for Treatment-1: Single 24 mg dose (1×24 mg) once daily for 5 consecutive days
Reference Product, Dose and Mode of Administration:
Name: Zofran®
Dosage form/Route of administration: Tablet/Oral
Regimen for Treatment-2: Single 8 mg dose (1×8 mg) twice daily at an 8-hour interval on Day 1 and at a 12-hour interval on Day 2
Regimen for Treatment-3: Single 24 mg dose (3×8 mg)
Treatments:
Treatment-1: Test administered once daily for 5 consecutive days
Treatment-2: Reference administered twice daily, at 8-hour intervals on Day 1 and at 12-hour intervals on Day 2
Treatment-3: A single 24 mg dose administered as three Reference tablets taken together
Treatment Periods:
Period 1: 2013/08/08 to 2013/08/12 (Treatment-1)
Period 1: 2013/08/08 to 2013/08/09 (Treatment-2)
Period 1: 2013/08/08 (Treatment-3)
Period 2: 2013/08/17 to 2013/08/21 (Treatment-1)
Period 2: 2013/08/17 to 2013/08/18 (Treatment-2)
Period 2: 2013/08/17 (Treatment-3)
Period 3: 2013/08/26 to 2013/08/30 (Treatment-1)
Period 3: 2013/08/26 to 2013/08/27 (Treatment-2)
Period 3: 2013/08/26 (Treatment-3)
Duration of Treatment:
Treatment-1: A single 24 mg dose of ondansetron (1×24 mg bimodal tablet (Electrolyte CDT Core)) ("Test Product") was orally administered once daily in the morning following a 10-hour overnight fast for 5 consecutive days.
Treatment-2: A single 8 mg dose of Zofran® (1×8 mg tablet) was orally administered twice daily, for two consecutive days, at 8-hour intervals on Day 1 and at 12-hour intervals on Day 2 (first dose in the morning of each day following a 10-hour overnight fast, and a second dose in the afternoon (Day 1) or evening (Day 2)) (for a total of 4 drug administrations).
Treatment-3: A single 24 mg dose of Zofran® (3×8 mg tablets) was orally administered following a 10-hour overnight fast.
The wash-out period between the first drug administrations of each study period was to be of 9 calendar days.
Blood Sampling Points:
During the study, a total of 98 blood samples were collected as follows:
Treatment-1: On Days 1 and 2 of dosing, 13 blood samples were collected per day. The first blood sample was collected prior to drug administration (within 5 minutes) while the others were collected 1, 2, 3, 4, 5, 6, 8, 10, 12, 14, 16 and 20 hours post drug administration.
On Days 3 and 4 of dosing, 8 blood samples were collected per day, the first blood sample was collected prior to drug administration (within 5 minutes) while the others were collected 2, 4, 6, 8, 10, 14 and 18 hours post drug administration.
On Day 5 of dosing, 10 blood samples were collected, the first blood sample was collected prior to drug administration (within 5 minutes) while the others were collected 2, 4, 6, 8, 10, 14, 18, 24 and 48 hours post drug administration.
For a total of 52 samples per subject with this treatment.
Treatment-2: On Day 1 of dosing, 15 blood samples were collected. The first blood sample was collected prior to the morning drug administration (within 5 minutes) while the others were collected 1, 2, 3, 4, 5, 6, 8, 9, 10, 11, 12, 14, 16, and 20 hours following the morning drug administration. The 8-hour blood sample was collected within 5 minutes before the afternoon administration.
On Day 2 of dosing, 17 blood samples were collected. The first blood sample was collected prior to the morning drug administration (within 5 minutes) while the others were collected 1, 2, 3, 4, 5, 6, 8, 12, 13, 14, 15, 16, 18, 20, 24 and 48 hours following the morning drug administration. The 12-hour blood sample was collected within 5 minutes before the evening administration.
For a total of 32 samples per subject with this treatment.
Treatment-3: On Day 1 of dosing, 14 blood samples were collected. The first blood sample was collected prior to the drug administration (within 5 minutes) while the others were collected 1, 2, 3, 4, 5, 6, 8, 10, 12, 16, 20, 24 and 48 hours following drug administration.
Criteria for Evaluation
Analytical Method:
Analyte: Ondansetron in human plasma
Method: HPLC with MS/MS detection
Assay range: 0.500 ng/mL to 300.000 ng/mL
Safety:
Safety was evaluated through assessment of adverse events, standard laboratory evaluations, vital signs, ECG and physical examination.
Mathematical Model and Statistical Methods of Pharmacokinetic Parameters
Main absorption and disposition parameters using a non-compartmental approach with a log-linear terminal phase assumption. Trapezoidal rule to estimate area under the curve, terminal phase estimation based on maximizing the coefficient of determination. The pharmacokinetic parameters of interest for this study were to be $C_{max}$ for each day of dosing, $AUC_{0-24}$ for each day of dosing, $C_{min}$ for each day of dosing and $C_{max}$ for each dosing day. Other parameters including $T_{max}$ for each dosing day, $AUC_T$, $AUC_\infty$, $K_{el}$ and $T_{1/2el}$ were to be calculated.
Statistical analysis of all pharmacokinetic parameters based on a parametric random ANOVA model. Two-sided 90% confidence interval of the ratio of geometric LSmeans obtained from the ln-transformed pharmacokinetic parameters.
During treatment with the Test product, $C_{max}$ and $AUC_{0-24}$ on Days 2 through 5 were to be compared with $C_{max}$ and $AUC_{0-24}$ on Day 1 to assess accumulation with repeated dosing.
Accumulation of the Test formulation was to be evaluated using ln-transformed $C_{max}$ and $AUC_{0-24}$. An Analysis of Variance (ANOVA) model was to be fitted with the day as a fixed effect and the subject as a random effect.
ANOVA Model for Treatments Comparisons:
  fixed factors: sequence, period, treatment
  random factor: subject (nested within sequence)
ANOVA for Accumulation:
  fixed factors: day
  random factor: subject Standards for Comparative Bioavailability:
Concentrations of ondansetron over time after dosing with the Test formulation were to be compared with those after dosing with the reference regimens. If the concentration of ondansetron after dosing with the test formulation was found to be similar to or higher than that after dosing with one or both of the reference regimens at most time points over the first 24-hour period studied, one can conclude that the Test product was to be at least as effective treatment with the existing regimens for vomiting and nausea.

Safety:
Descriptive statistics.

SUMMARY OF RESULTS

Safety Results:
Nine (9) of the 18 subjects (50.0%) included in this study experienced a total of 28 adverse events. All of the 28 adverse events reported during the study were mild in severity. The below table presents the number of adverse events by treatment classified by severity and causality:

TABLE 28

Number of Patients with Adverse Events

| Treatments | Severity | | | Causality | |
|---|---|---|---|---|---|
| | Mild | Moderate | Severe | Reasonable Possibility | No Reasonable Possibility |
| RHB-102 | 6 | 0 | 0 | 4 | 4 |
| Zofran 8 mg bid | 5 | 0 | 0 | 3 | 3 |
| Zofran 24 mg × 1 | 6 | 0 | 0 | 3 | 3 |
| Total number of patients with adverse events | 9 | 0 | 0 | 7 | 6 |

Six (6) subjects (33.3%) reported 12 adverse events (2 different System Organ Classes and 7 different Preferred Terms) after the administration of Treatment-1, 5 subjects (27.8%) reported 7 adverse events (3 different System Organ Classes and 5 different Preferred Terms) after the administration of Treatment-2 and 6 subjects (33.3%) reported 9 adverse events (4 different System Organ Classes and 7 different Preferred Terms) after the administration of Treatment-3. The number of subjects who experienced at least one adverse event during the study was similar for all 3 treatments.

Adverse events experienced by two or more subjects with any treatment condition were (Treatment-1, Treatment-2, Treatment-3) abnormal faeces (2, 0, 0), constipation (2, 0, 1), vessel puncture site haematoma (2, 3, 2), vessel puncture site pain (0, 1, 1), headache (0, 1, 1) and somnolence (0, 1, 1). Furthermore, related adverse events experienced by two or more subjects with any treatment condition were (Treatment-1, Treatment-2, Treatment-3) constipation (2, 0, 1), headache (0, 1, 1) and somnolence (0, 1, 1).

No serious adverse events or deaths were reported during this study. Moreover, no clinically significant laboratory evaluations, vital signs, ECGs or physical examinations were observed during this study.

No adverse events required the use of medications following the first dosing.

No subject was withdrawn from the study for safety reasons.

Pharmacokinetic Results:

Treatment Comparisons:

The main pharmacokinetic parameters ($C_{min}$, $C_{max}$, $C_{24}$ and $AUC_{0-24}$) of each treatment were measured for each dosing day. Comparisons between the first 2 days of administration of Test Product with the 2 days of administration of Zofran 8 mg bid were performed as well as a comparison between the first day of administration of Test Product with the administration of Zofran 24 mg. A summary of the results of these comparisons is presented in FIGS. 23-28 and Tables 29-32.

TABLE 29

Pharmacokinetic Parameters After Administration of Test Product

| | Test Product | | | |
|---|---|---|---|---|
| | DAY 1 | | DAY 2 | |
| PARAMETER | MEAN | C.V. (%) | MEAN | C.V. (%) |
| $C_{max}$ (ng/mL) | 54.0 | 35.3 | 63.7 | 42.4 |
| ln ($C_{max}$) | 3.94 | 8.4 | 4.08 | 9.6 |
| $C_{min}$ (ng/mL) | 10.2 | 66.5 | 13.6 | 60.1 |
| ln ($C_{min}$) | 2.14 | 28.1 | 2.45 | 23.9 |
| $C_{24}$ (ng/mL) | 11.5 | 64.0 | 13.7 | 59.0 |
| ln ($C_{24}$) | 2.27 | 26.4 | 2.46 | 23.2 |
| $AUC_{0-24}$ (ng * h/mL) | 637.6 | 38.6 | 796.8 | 46.6 |
| ln ($AUC_{0-24}$) | 6.389 | 5.9 | 6.589 | 6.5 |

TABLE 30

Pharmacokinetic Parameters After Administration of Zofran 8 mg bid

| | Zofran 8 mg bid | | | |
|---|---|---|---|---|
| | DAY 1 | | DAY 2 | |
| PARAMETER | MEAN | C.V. (%) | MEAN | C.V. (%) |
| $C_{max}$ (ng/mL) | 46.0 | 38.7 | 46.6 | 45.6 |
| ln ($C_{max}$) | 3.77 | 9.0 | 3.76 | 11.1 |
| $C_{min}$ (ng/mL) | 8.72 | 73.2 | 11.6 | 69.3 |
| ln ($C_{min}$) | 1.95 | 34.5 | 2.26 | 27.1 |
| $C_{24}$ (ng/mL) | 8.72 | 73.2 | 13.6 | 68.5 |
| ln ($C_{24}$) | 1.95 | 34.5 | 2.42 | 26.0 |
| $AUC_{0-24}$ (ng * h/mL) | 539.5 | 43.2 | 606.9 | 49.4 |
| ln ($AUC_{0-24}$) | 6.211 | 6.5 | 6.306 | 7.2 |

TABLE 31

Pharmacokinetic Parameters After Administration of Zofran 24 mg × 1

| | Zofran 24 mg × 1 | |
|---|---|---|
| | DAY 1 | |
| PARAMETER | MEAN | C.V. (%) |
| $C_{max}$ (ng/mL) | 140 | 31.5 |
| ln ($C_{max}$) | 4.90 | 6.0 |
| $C_{min}$ (ng/mL) | 8.07 | 68.9 |
| ln ($C_{min}$) | 1.90 | 33.0 |
| $C_{24}$ (ng/mL) | 8.07 | 68.9 |
| ln ($C_{24}$) | 1.90 | 33.0 |
| $AUC_{0-24}$ (ng * h/mL) | 1058 | 34.4 |
| ln ($AUC_{0-24}$) | 6.913 | 4.6 |

TABLE 32

Treatment Comparisons (Continued)

| Comparison | DAY | INTRA-SUBJECT C.V. (%) | GEOMETRIC LSMEANS* RHB-102 | GEOMETRIC LSMEANS* TREATMENT** | RATIO (%) | 90% CONFIDENCE LIMITS (%) LOWER | 90% CONFIDENCE LIMITS (%) UPPER |
|---|---|---|---|---|---|---|---|
| $C_{max}$ | | | | | | | |
| Test Product vs Zofran 8 mg bid | 1 | 13.6 | 51.2 | 43.3 | 118 | 109 | 128 |
| Test Product vs Zofran 24 mg × 1 | 1 | 13.6 | 51.2 | 135 | 38.1 | 35.3 | 41.1 |
| Test Product vs Zofran 8 mg bid | 2 | 11.1 | 59.0 | 42.7 | 138 | 130 | 147 |
| $C_{min}$ | | | | | | | |
| Test Product vs Zofran 8 mg bid | 1 | 28.1 | 8.50 | 7.04 | 121 | 103 | 141 |
| Test Product vs Zofran 24 mg × 1 | 1 | 28.1 | 8.50 | 6.69 | 127 | 109 | 148 |
| Test Product vs Zofran 8 mg bid | 2 | 22.7 | 11.5 | 9.61 | 120 | 105 | 137 |
| $C_{24}$ | | | | | | | |
| Test Product vs Zofran 8 mg bid | 1 | 26.6 | 9.69 | 7.04 | 138 | 119 | 160 |
| Test Product vs Zofran 24 mg × 1 | 1 | 26.6 | 9.69 | 6.69 | 145 | 125 | 168 |
| Test Product vs Zofran 8 mg bid | 2 | 23.8 | 11.7 | 11.3 | 104 | 90.9 | 120 |
| $AUC_{0-24}$ | | | | | | | |
| Test Product vs Zofran 8 mg bid | 1 | 12.2 | 595.4 | 498.4 | 119.5 | 111.6 | 127.9 |
| Test Product vs Zofran 24 mg × 1 | 1 | 12.2 | 595.4 | 1005 | 59.22 | 55.30 | 63.42 |
| Test Product vs Zofran 8 mg bid | 2 | 12.4 | 726.9 | 547.9 | 132.7 | 123.5 | 142.6 |

*Units are ng/mL for $C_{max}$, $C_{min}$ and $C_{24}$ and ng*h/mL for $AUC_{0-24}$
**Refers to Zofran 8 mg bid or Zofran 24 mg × 1 according to the comparison Concentration Comparisons:

Concentrations of ondansetron at selected time points after dosing with Test Product were compared with those after dosing with Zofran 8 mg bid and Zofran 24 mg×1. Measured concentrations achieved with Test Product at 10, 12 14 and 16 hours post-dose for Day 1 and at 20 hours post-dose for Day 2 were compared to the respective measured concentrations of ondansetron achieved with the administration of the other treatments. A summary of the results of these comparisons is presented in the following tables.

TABLE 33

Concentration After Administration of Test Product

| PARAMETER | DAY | Test Product MEAN | Test Product C.V. (%) |
|---|---|---|---|
| $C_{10}$ (ng/mL) | 1 | 30.2 | 40.3 |
| ln ($C_{10}$) | 1 | 3.33 | 13.0 |
| $C_{12}$ (ng/mL) | 1 | 25.0 | 42.8 |
| ln ($C_{12}$) | 1 | 3.14 | 13.4 |
| $C_{14}$ (ng/mL) | 1 | 20.7 | 48.1 |
| ln ($C_{14}$) | 1 | 2.93 | 15.4 |
| $C_{16}$ (ng/mL) | 1 | 17.7 | 51.9 |
| ln ($C_{16}$) | 1 | 2.76 | 17.8 |
| $C_{20}$ (ng/mL) | 1 | 12.8 | 57.9 |
| ln ($C_{20}$) | 1 | 2.41 | 22.3 |

TABLE 34

Concentration After Administration of Zofran 8 mg bid

| PARAMETER | DAY | Zofran 8 mg bid MEAN | Zofran 8 mg bid C.V. (%) |
|---|---|---|---|
| $C_{10}$ (ng/mL) | 1 | 44.7 | 37.4 |
| ln ($C_{10}$) | 1 | 3.74 | 8.9 |
| $C_{12}$ (ng/mL) | 1 | 32.9 | 44.1 |
| ln ($C_{12}$) | 1 | 3.41 | 12.2 |
| $C_{14}$ (ng/mL) | 1 | 24.1 | 48.2 |
| ln ($C_{14}$) | 1 | 3.08 | 15.5 |
| $C_{16}$ (ng/mL) | 1 | 19.2 | 56.7 |
| ln ($C_{16}$) | 1 | 2.82 | 18.8 |
| $C_{20}$ (ng/mL) | 1 | 12.2 | 63.1 |
| ln ($C_{20}$) | 1 | 2.33 | 26.3 |

TABLE 35

Concentration After Administration of Zofran 24 mg × 1

| PARAMETER | DAY | Zofran 24 mg × 1 MEAN | Zofran 24 mg × 1 C.V. (%) |
|---|---|---|---|
| $C_{10}$ (ng/mL) | 1 | 37.9 | 40.1 |
| ln ($C_{10}$) | 1 | 3.56 | 11.4 |
| $C_{12}$ (ng/mL) | 1 | 27.4 | 44.2 |
| ln ($C_{12}$) | 1 | 3.22 | 13.4 |
| $C_{14}$ (ng/mL) | 1 | N/AP | N/AP |
| ln ($C_{14}$) | 1 | N/AP | N/AP |

TABLE 35-continued

Concentration After Administration of Zofran 24 mg × 1

| PARAMETER | DAY | Zofran 24 mg × 1 MEAN | C.V. (%) |
|---|---|---|---|
| $C_{16}$ (ng/mL) | 1 | 16.0 | 54.8 |
| ln ($C_{16}$) | 1 | 2.64 | 19.6 |
| $C_{20}$ (ng/mL) | 1 | 10.8 | 60.6 |
| ln ($C_{20}$) | 1 | 2.23 | 25.5 |

N/AP: Not applicable

TABLE 36

Concentration Comparisons After Administration

| Comparison | Parameter | Day | INTRA-SUBJECT C.V. (%) | GEOMETRIC LSMEANS (ng/mL) RHB-102 | TREATMENT* | RATIO (%) | 90% CONFIDENCE LIMITS (%) LOWER | UPPER |
|---|---|---|---|---|---|---|---|---|
| Test Product vs Zofran 8 mg bid | $C_{10}$ | 1 | 18.9 | 27.8 | 42.3 | 65.8 | 59.2 | 73.1 |
| Test Product vs Zofran 24 mg × 1 | $C_{10}$ | 1 | 18.9 | 27.8 | 35.1 | 79.2 | 71.3 | 88.0 |
| Test Product vs Zofran 8 mg bid | $C_{12}$ | 1 | 16.9 | 23.0 | 30.3 | 76.0 | 69.1 | 83.5 |
| Test Product vs Zofran 24 mg × 1 | $C_{12}$ | 1 | 16.9 | 23.0 | 25.1 | 91.5 | 83.2 | 101 |
| Test Product vs Zofran 8 mg bid | $C_{14}$ | 1 | 21.7 | 18.7 | 21.7 | 86.4 | 76.2 | 98.0 |
| Test Product vs Zofran 8 mg bid | $C_{16}$ | 1 | 18.9 | 15.7 | 16.8 | 93.7 | 84.2 | 104 |
| Test Product vs Zofran 24 mg × 1 | $C_{16}$ | 1 | 18.9 | 15.7 | 14.1 | 112 | 101 | 124 |
| Test Product vs Zofran 8 mg bid | $C_{20}$ | 1 | 22.6 | 11.1 | 10.3 | 108 | 95.5 | 123 |
| Test Product vs Zofran 24 mg × 1 | $C_{20}$ | 1 | 22.6 | 11.1 | 9.28 | 120 | 106 | 136 |

*Refers to Zofran 8 mg bid or Zofran 24 mg × 1 according to the comparison

Accumulation Evaluation:
In order to evaluate the accumulation of ondansetron after multiple administrations of Test Product, $C_{max}$ and $AUC_{0-24}$ were measured for 5 consecutive days of dosing and compared to the single dose administration of Test Product at Day 1. A summary of the results is presented in the following tables.

TABLE 37

Accumulation Evaluation of Test Product - $C_{max}$

| Comparison | INTRA-SUBJECT C.V. (%) | GEOMETRIC LSMEANS (ng/mL) DAY* | DAY 1 | RATIO (%) | 90% CONFIDENCE LIMITS (%) LOWER | UPPER |
|---|---|---|---|---|---|---|
| Day 2 vs Day 1 | 8.8 | 59.0 | 51.2 | 115 | 110 | 121 |
| Day 3 vs Day 1 | 8.8 | 60.6 | 51.2 | 118 | 113 | 124 |
| Day 4 vs Day 1 | 8.8 | 62.7 | 51.2 | 122 | 117 | 129 |
| Day 5 vs Day 1 | 8.8 | 64.1 | 51.2 | 125 | 119 | 131 |

*Refers to Day 2, 3, 4 or 5 according to the comparison

TABLE 38

Accumulation Evaluation of Test Product - $AUC_{0-24}$

| Comparison | INTRA-SUBJECT C.V. (%) | GEOMETRIC LSMEANS (ng*h/mL) DAY* | DAY 1 | RATIO (%) | 90% CONFIDENCE LIMITS (%) LOWER | UPPER |
|---|---|---|---|---|---|---|
| Day 2 vs Day 1 | 9.1 | 726.9 | 595.4 | 122.1 | 116.1 | 128.4 |
| Day 3 vs Day 1 | 9.1 | 743.8 | 595.4 | 125.0 | 118.8 | 131.4 |

TABLE 38-continued

Accumulation Evaluation of Test Product - $AUC_{0-24}$

| Comparison | INTRA-SUBJECT C.V. (%) | GEOMETRIC LSMEANS (ng*h/mL) | | RATIO (%) | 90% CONFIDENCE LIMITS (%) | |
|---|---|---|---|---|---|---|
| | | DAY* | DAY 1 | | LOWER | UPPER |
| Day 4 vs Day 1 | 9.1 | 781.3 | 595.4 | 131.2 | 124.7 | 138.0 |
| Day 5 vs Day 1 | 9.1 | 784.0 | 595.4 | 131.7 | 125.2 | 138.5 |

*Refers to Day 2, 3, 4 or 5 according to the comparison

Pharmacokinetic Discussion:
Treatment Comparisons:
Test Product Vs Zofran 8 mg Bid:
The results presented herein show that the $C_{min}$ and $C_{max}$ over 24 hours as well as $AUC_{0-24}$ were higher during the first two days of administration of Test Product as compared to both days of administration of Zofran 8 mg bid.
The $C_{24}$ was found to be higher with the administration of Test Product for the first day of treatment and was found to be comparable between Test Product and Zofran 8 mg bid for the second day of treatment.
Test Product Vs Zofran 24 mg×1:
The $C_{min}$ and $C_{24}$ were also higher for the first day of administration of Test Product as compared to the administration of Zofran 24 mg×1.
However, the $C_{max}$ and $AUC_{0-24}$ achieved with the administration of Test Product were about 60% (ratio of 38%) and 40% (ratio of 59%) lower than the $C_{max}$ and $AUC_{0-24}$ achieved with the administration of Zofran 24 mg×1.
Concentration Comparisons:
Test Product Vs Zofran 8 mg Bid:
Measured concentrations from 3 through 8 hours after initial dosing were higher after administration of Test Product. At 10 and 12 hours, concentrations were found to be lower with the administration of Test Product for the first day of treatment; subsequent concentrations were similar between the two groups on the first day.
Due to the later administration of the second dose on day 2, the shape of the concentration curve for Zofran 8 mg bid was somewhat different than on the first day, but the overall results were similar.
Test Product Vs Zofran 24 mg×1:
Measured concentrations through 10 hours were found to be lower following the administration of Test Product. The measured concentration at 12 and 16 hours were found to be comparable between the two treatments and higher for Test Product at 20 and 24 hours.
Accumulation Evaluation
The accumulation evaluation performed on $C_{max}$ demonstrated a first 15% increase between Day 1 and Day 2 and also demonstrated a uniform increase of the ratio estimate based on back-transformation of LS Means' difference throughout Day 3 to Day 5 (118-125% of $C_{max}$ observed on Day 1) indicating the accumulation of ondansetron following multiple administrations of Test Product. A similar increase was observed for $AUC_{0-24}$ for Day 3 and 4 (125-131% of $AUC_{0-24}$ observed on Day 1) following a 22% increase between Day 1 and Day 2.
The ratio estimate based on back-transformation of LS Means' difference for the $AUC_{0-24}$ was similar for Day 4 (131%) and Day 5 (132%) indicating that steady state had been reached between day 4 and 5 of repeated daily Test Product administration.

Conclusions:
Comparative Bioavailability:
The results presented herein demonstrate that bioavailability of Test Product is noninferior to that of Zofran 8 mg bid, the approved regimen for prevention of nausea and vomiting due to moderately emetogenic chemotherapy.
Key points in this comparison:
Geometric mean $AUC_{0-24}$ of Test Product was 19% higher than that of Zofran 8 mg bid (90% CI 12-28%) on day 1 of dosing, 33% higher (90% CI 24-43%) on day 2.
Geometric mean $C_{max}$ of Test Product was 18% higher than that of Zofran 8 mg bid (90% CI 9-28%) on day 1 of dosing, 38% higher on day 2 (90% CI 30-47%).
Both $C_{24}$ and $C_{min}$ of Test Product were higher than those of both Zofran 8 mg bid and Zofran 24 mg×1
Ondansetron levels were similar to or higher after Test Product than after Zofran 8 mg at all time points except 10 and 12 hours after initial dosing on day 1 and 14-20 hours on day 2.
At 10 and 12 hours after dosing on day 1, the levels after Test Product were 107% and 72% higher than the trough ondansetron level 8 hours after the initial dose of Zofran 8 mg.
At 14-20 hours after initial dosing on day 2, levels after Test Product were 47-159% higher than the trough ondansetron level 12 hours after the initial dose of Zofran 8 mg.
In addition, from 12 hours on, levels of ondansetron after Test Product were similar to or higher than levels after Zofran 24 mg×1, which is the approved regimen for highly emetogenic chemotherapy.
The plasma level of ondansetron after Test Product is similar to or higher than the plasma level after Zofran 8 mg given twice daily at most time points tested, and the concentrations at other time points are considerably higher than trough levels at 8 or 12 hours (days 1 and 2 respectively) after the initial dose for the reference regimen of Zofran 8 mg twice daily. Therefore, it is reasonable to conclude that the efficacy of Test Product is at least as good as that of the Zofran 8 mg twice daily.
Accumulation Assessment:
The once daily administration of Test Product for 5 consecutive days under fasting conditions confirmed an accumulation of ondansetron in human plasma. Maximum plasma concentrations increased from 15% to 25% from Day 2 to Day 5. Following the first 15% increase, an increase of ≈3% of the maximum concentration was observed for each subsequent dosing day. $AUC_{0-24}$ increased from 22 to 31% from Day 2 to Day 4 and subsequently stabilized to 32% for Day 5 indicating arrival at a steady state situation.
Safety and Tolerability of Test Product:
The results presented herein show that the once daily administration of Test Product for 5 consecutive days was safe and well tolerated by the subjects included in this study. Furthermore, the number of subjects who experienced at least one adverse event was comparable between all treatment groups and all of the 28 adverse events reported during the study were mild in severity, demonstrating that the safety and tolerability of the extended-release formulation, Test Product, was similar to the safety profile of the other treatments.

Despite some drug accumulation with repeated dosing, there was no indication that this resulted in any safety issues. In particular, the incidence of mild QTc prolongation was higher after a single 24 mg dose of immediate release Zofran than it was after 5 daily doses of Test Product.

Example 19—2-Arm Crossover Comparative Bioavailability Study of Solid Dosage Forms 2-arm crossover comparative bioavailability study of a single dose of a solid dosage form of the present invention versus a single ondansetron 16 mg suppository in Healthy Male and Female Volunteers/Fasting State.
Objectives:
The primary objective of this study was to explore the relative bioavailability between the Test formulation on ondansetron 24 mg bimodal release tablet and a once daily ondansetron suppository formulation, approved in many countries in Europe (Zofran® 16 mg suppository). Secondary objectives of the study were:
 1. To Assess the Safety and Tolerability of the Extended-Release Formulation on Healthy Volunteers.
Methodology:
Single center, randomized, single dose, laboratory-blinded, 2-period, 2-sequence, crossover design.
Number of Subjects (Planned and Analyzed):
Planned for inclusion: 20
Included: 20
Drop-outs: 0
Analyzed: 20
Considered in the pharmacokinetic and statistical analysis: 20
Considered in the safety analysis: 20
Test Product, Dose and Mode of Administration, Batch Number:
Name: Ondansetron
Dosage form/Route of administration: A bimodal tablet of the present invention (Electrolyte CDT Core)/Oral ("Test Product")
Regimen for Treatment-1: Single 24 mg dose (1×24 mg) once daily for 1 day
Reference Product, Dose and Mode of Administration:
Name: Zofran® 16 mg suppository ("Reference")
Regimen for Treatment-2: Single 16 mg dose (1×16 mg) once daily for 1 day.
Study Sequences:

|  | Period 1 | Period 2 |
| --- | --- | --- |
| Sequence 1 (n = 10) | Test | Reference |
| Sequence 2 (n = 10) | Reference | Test |

Treatments:
Subjects received each of the following investigational products on one occasion according to the randomization list:
Treatment-1 1× Test (Ondansetron 24 mg Bimodal Tablet [Electrolyte CDT Core]); Test
Treatment-2 1× Zofran® 16 mg suppository, Reference
Selection and Timing of Dose for Each Subject:
Subjects fasted overnight for at least 10 hours prior to drug administration.
Treatment-1:
Thereafter, a single dose of the Test formulation was orally administered with approximately 240 mL of water at ambient temperature.
Treatment-2
Thereafter, a single dose of the Reference formulation was rectally administered. No water was provided with the suppository administration.
Fasting continued for at least 4 hours following drug administration, after which a standardized lunch was served. A supper and a light snack were also served at appropriate times thereafter, but not before 9 hours after dosing. Water was allowed ad libitum until 1 hour pre-dose and beginning 1 hour after drug administration.
Blood Sampling Schedule
Blood samples for pharmacokinetic measurements were collected prior to and up to 48 hours (serial sampling) after each drug administration. The blood sampling schedule was at sampling time (in hours): 0, 1, 2, 3, 4, 5, 6, 8, 10, 12, 14, 16, 20, 24, and 28.
Summary of Results
Analysis of Efficacy
The mean $C_{min}$ were respectively 2.629 ng/mL and 0.793 ng/mL for the Test and Reference formulations. The Test to References $C_{min}$ ratio of geometric LSmeans was 277.21% (90% CI: 162.84% to 471.90%).
The mean $C_{max}$ were respectively 53.055 ng/mL and 24.392 ng/mL for the Test and Reference formulations. The Test to Reference $C_{max}$ ratio of geometric LSmeans was 219.26% (90% CI: 192.74% to 249.43%)
The mean $C_{24}$ were respectively 10.542 ng/mL and 5.570 ng/mL for Test and Reference formulations. The Test to Reference $C_{24}$ ratio of geometric LSmeans was 203.59% (90% CI: 157.81% to 262.65%).
The median $T_{max}$ was 4.00 and 5.00 hours for Test and Reference formulations, respectively.
The mean $AUC_{0-24}$ were respectively 629.082 ng·h/mL and 321.115 ng·h/mL for the Test and Reference formulations. The Test to Reference $AUC_{0-24}$ ratio of geometric LSmeans was 197.68% (90% CI: 173.80% to 224.85%).
The mean $AUC_{0-T}$ were respectively 781.788 ng·h/mL and 382.769 ng·h/mL for the Test and Reference formulations. The Test to Reference $AUC_{0-T}$ ratio of geometric LSmeans was 212.62% (90% CI: 180.62% to 250.30%).
The mean $\lambda_z$ was 0.0665 hours$^{-1}$ for the Test formulation and 0.0914 hours$^{-1}$ for the Reference formulation. The mean $T_{half}$ value was 12.69 and 8.16 hours, for the Test and Reference formulations, respectively.
The mean $AUC_{0-\infty}$ were respectively 848.005 ng·h/mL and 407.528 ng·h/mL for the Test and Reference formulations. The Test to Reference $AUC_{0-\infty}$ ratio of geometric LSmeans was 212.76% (90% CI: 183.77% to 246.33%).
The extent of exposure to ondansetron was around 113% higher when administered as a single 24 mg bimodal tablet [Electrolyte CDT Core]) than when administered as a 16 mg Zofran® suppository. This implies 42% higher bioavailability for a composition of the present invention as compared to the Zofran® suppository. Furthermore, the coefficient of inter-subject variance for the Test formulation was similar to or lower than for the Zofran® suppository for all pharmacokinetic parameters assessed. The pharmacokinetic data showed that the Test formulation provides higher plasma concentration levels than the Zofran® suppository throughout the 24 hours period following dosing, therefore indicating that the efficacy of the Test formulation would be at least as high as that of the Zofran® suppository.

The secondary objective of this study was to assess the safety and tolerability of the bimodal release formulation on healthy volunteers. The incidence and severity of adverse events related to the bimodal release formulation was comparable to that observed following the Zofran® suppository even though there was a higher exposure and peak level of ondansetron following the administration of the bimodal release formulation. Overall, the two different formulations tested were safe and well tolerated by the subjects included in this study.

Example 20—(Prophetic) Randomized, Placebo-Controlled Trial of Solid Dosage Forms of the Present Invention for Vomiting Due to Presumed Acute Gastroenteritis or Gastritis Acute gastroenteritis is inflammation of the stomach, small intestine or large intestine, leading to a combination of abdominal pain, cramping, nausea, vomiting and diarrhea. Acute gastritis is inflammation of the stomach; patients with acute gastritis may have vomiting without diarrhea. For purposes of this protocol, patients must present with at least vomiting, as described below, with or without other symptoms.

Acute gastroenteritis is a major health problem worldwide. While mortality is greatest in developing countries and in both the very young and old, morbidity of acute gastroenteritis is shared by all ages and economic strata. In the US, most cases of acute gastroenteritis are viral, most commonly rotavirus and norovirus. In the US, there are between 15-25 million episodes of viral gastroenteritis annually, leading to 3-5 million office visits and 200,000 hospitalizations. While mortality is low, among the 17,000 people dying from acute gastroenteritis in the US each year, 83% are over age 65. Most cases are self-limited, resolving in one to several days. Mild to moderate cases are generally treated symptomatically. In children, there are guidelines for oral rehydration therapy. More severe and prolonged cases may require diagnostic studies for etiologic organisms. Depending on the severity and etiology, treatment varies from dietary modifications, including oral rehydration therapy, to intravenous fluids and antibiotics. Antiemetics and antidiarrheals are often used.

The Test product for this study is a bimodal release oral formulation of ondansetron. It contains 24 mg of ondansetron, 6 mg immediate release and 18 mg in an extended release matrix. As described above, pharmacokinetic studies in healthy volunteers have demonstrated rapid early release, with appearance of drug in the plasma within half an hour of dosing, similarly to immediate release Zofran, but with sustained drug availability over 24 hours. Thus, the Test product should provide rapid relief from nausea and vomiting in patients not requiring immediate intravenous medication, yet require only once daily dosing for a sustained effect over the several days of illness. The safety profile of the Test product is similar to that of Zofran 8 mg, as demonstrated in volunteer studies described above.

Study drug Ondansetron 24 mg Bimodal Release Tablets
Comparator Placebo
Rationale Ondansetron causes side effects in few patients, but gastroenteritis patients administered intravenous but immediate release oral ondansetron frequently require multiple doses to control their symptoms. Thus, use of a modified release formulation may be of considerable benefit by providing rapid relief of symptoms and maintaining relief without need for redosing over the course of the illness, which is usually approximately one day.

A solid dosage form for this study is a modified release oral tablet formulations of ondansetron. It contains 6 mg ondansetron for immediate release and 18 mg in an extended release core. It provides early ondansetron levels similar to a single 8 mg immediate release tablet and sustained release over a 24-hour period. This should enable once daily dosing, so that a single dose of a solid dosage form of the present invention should be sufficient to control nausea and vomiting from acute gastroenteritis for most patients.

Objectives
Primary: Comparison of the proportion of patients without further vomiting without rescue medication ≥30 minutes after the first dose of study medication through release from the emergency department.
Secondary: Comparison between ondansetron and placebo groups of
  Incidence and frequency of vomiting through 4 days following first-dose of study medication
  Proportion of patients receiving rescue antiemetic therapy
  Proportion of patients receiving intravenous hydration
  Proportion of patients requiring hospitalization
  Proportion of patients returning to emergency department/urgent care department after initial discharge
  Time from first dose of study medication to first episode of vomiting after dosing (after second dose in ED for patients who receive 2 doses)
  Severity of nausea, evaluated by Likert scales
  Incidence and frequency of diarrhea
  Time to resumption of normal activities (work/school/household)
  Adverse event profiles
Population Adults and children ≥age 12 with vomiting from presumed acute gastroenteritis or gastritis of ≤24 hours duration
  Children <age 18 must have parental consent
Inclusion Criteria:
  Patients must have vomited at least twice in the 4-6 hours preceding signing informed consent
  Emesis must have been nonbilious and nonbloody
  All patients (or a parent or guardian for patients <age 18) must sign informed consent.
Exclusion Criteria:
  Severe dehydration
  Signs and symptoms severe enough to require immediate parenteral hydration and/or parenteral antiemetic medication
  Temperature >39.0° C.
  Likely etiologies for acute vomiting and diarrhea other than acute infectious or toxic gastroenteritis or gastritis This includes signs of an acute abdomen, which may require surgical intervention
  Use within 24 hours of study entry of medication for treatment of nausea and/or vomiting
  Congestive heart failure, bradyarrhythmia (including baseline pulse<55/min), known long QT syndrome
  Patient who have known QTc prolongation>480 msec, noted on prior ECG, or who are taking medication known to cause QT prolongation
  Known underlying disease which could affect assessment of hydration or modify outcome of treatment, e.g., renal failure, diabetes mellitus, liver disease, alcoholism Patients with type 2 diet-controlled diabetes mellitus whose baseline blood glucose is <200 may be entered into the study Abdominal surgery within the past 3 months History of bariatric surgery or bowel obstruction at any time Hypersensitivity or other known intolerance to ondansetron or other 5-HT$_3$ antagonists Patient has taken apomorphine within 24 hours of screening Patient has previously participated in this study Patient has participated in another interventional clinical trial, for any indication, in the past 30 days For women of childbearing potential: documented or possible pregnancy Design Methodology Randomized, double-blind, placebo-controlled, parallel group study Patients presenting to the emergency department who fulfill inclusion criteria will be asked to participate. Qualifying patients, once they have signed consent, will be stratified by age (≥vs<age 18) and randomized 60:40 to test formulation or matching placebo.

Patients will receive one oral dose of either study medication as soon as feasible. If a patient vomits within 15-30 minutes of the initial dose of study medication, he/she will receive a second dose. If a patient vomits again, regardless of how long after the second dose of study medication, no further study medication will be administered.

Patients vomiting ≥30 minutes after the first dose of study medication may receive rescue antiemetics, either parenterally or orally. In addition, a) patients with severe nausea ≥30 minutes after dosing with study medication and who in the treating physician's opinion require treatment, may receive rescue medication. b) These patients may receive intravenous hydration in addition to or in place of parenteral antiemetics if they are unable to tolerate oral hydration. However, only severely symptomatic patients clearly unable to tolerate oral hydration may receive intravenous hydration.

Metoclopramide 0.3 mg/kg, maximum dose 10 mg, administered intravenously will be the default rescue medication. Oral metoclopramide or other antiemetics administered either intravenously or orally may be used at the investigator's discretion. However, patients are not to receive ondansetron or other 5-HT$_3$ antagonists by any route for at least 24 hours after administration of study medication. The following 5-HT$_3$ antagonists are available in the US: alosetron (Lotronex), dolasetron (Anzemet), granisetron (Sancuso and others), ondansetron (Zofran, Zuplenz and others), palonsetron (Aloxi).

Oral fluids will be administered as tolerated once a patient has not vomited for 30 minutes after dosing with study medication (second dose for those patients receiving 2 doses in the ED).

Patients tolerating oral fluids will be discharged once deemed stable by the attending physician but not prior to 2 hours after dosing. On discharge, patients will be given 3 additional doses of study medication to take once daily if necessary.

Patients who do not tolerate oral fluids may receive parenteral hydration.

Data will be collected daily for up to 4 days following study initiation (until symptoms have resolved) to ascertain whether the patient had further vomiting, other sequelae of the acute gastroenteritis or required further medical care for the gastroenteritis. Data may be collected by entry by the patient or a caregiver into a web-based system or on paper, or by telephone contact daily from a study staff member. If during the follow-up period, symptoms progress or worsen or new symptoms develop, the patient may be asked to return for further evaluation. If by day 4 after discharge (i.e., the day after the last dose of study medication), the patient still notes gastroenteritis symptoms, he or she will be instructed to return for further evaluation.

Endpoints Efficacy:

Primary:

Absence of vomiting from 30 minutes after the first dose of study medication through release from the emergency department without receipt of rescue medication.

Secondary:

Incidence and frequency of vomiting through 4 days following first dose of study Requirement for rescue antiemetic Treatment with intravenous hydration Hospital admission Return to emergency department/urgent care department for gastrointestinal symptoms Severity and time to resolution of nausea Severity of nausea will be measured on a 5-point Likert scale Incidence and frequency of diarrhea Time to resumption of normal activities Pharmacokinetics: Incidence and severity of adverse events through time of last follow-up call Safety: Statistics Successful treatment is absence of further vomiting while in the emergency department on the day of study entry 30 minutes after initial administration of study administration without use of rescue antiemetic. It is expected that 40% of the placebo group and 20% of the ondansetron group will fail therapy. To demonstrate a statistically significant difference with two-tailed p value=0.01 and power=90%, 320 patients will be entered into the study, 192 randomized to Study drug and 128 to placebo.

Patients will be stratified by age (< or ≥age 18) at baseline.

Patient demographics and disease characteristics will be summarized with descriptive statistics.

Safety and efficacy analyses will be based on all patients who receive any study medication.

The incidence of treatment failure (vomiting AO minutes after initial administration of study medication and while patient is still in the emergency/urgent care department) will be compared by Mantel-Haenszel test.

No interim analysis will be conducted.

Study Assessments

| Day | 1 | 1 | 1 | 2 | 3 | 4 | 5 |
|---|---|---|---|---|---|---|---|
| Time, hours | −1 to 0 | 0 | 0-T | NA | NA | NA | NA |
| Baseline assessments[a] | X | | | | | | |
| Study drug administration | | X[e] | | X[f] | X[f] | X[f] | |
| Observation[b] | | | X | | | X[c] | X[c] |
| Patient reported events[c] | | | | X | X | X | X |

| | | | | | | | |
|---|---|---|---|---|---|---|---|
| Concomitant medications[d] | X | X | X | X | X | X | X |
| Adverse events | | X | X | X | X | X | X |

Notes:

[a]History, physical including VS (pulse, respiratory rate, blood pressure, temperature and, at baseline only height and weight), informed consent. For all patients ≥age 50, optional for patients <age 50: CBC with platelet count, biochemical profile, urinalysis. Blood and urine specimens should be taken expeditiously at the beginning of assessment, but patient entry into the study and treatment need not wait for lab results (other than pregnancy test when required) unless clinically indicated. After phlebotomy, a saline lock may be placed so that the patient will not require an additional needle stick should he/she require intravenous fluids subsequently. History of present illness should include questioning regarding precipitating/causative factors, as well as recording of number and character of emetic and diarrheal episodes. Patients with diet-controlled type 2 diabetes mellitus are to have a finger stick blood glucose.

For women of childbearing potential, as defined in the exclusion criteria: urine or serum pregnancy test. Negative pregnancy test result must be obtained prior to treating a patient on study.

[b]Patients are to be observed in the emergency department for a minimum of 2 hours, with VS at least once every hour and recording of intake (both oral and parenteral) and number of voidings. All episodes of vomiting and diarrhea are to be recorded, and severity of nausea at baseline and every hour while in the ED noted. At a minimum of 2 hours after initial administration of study medication, patients may be discharged when clinically appropriate.

[c]Patients will complete a diary either online or on paper or be contacted each day following treatment to a maximum of 4 days to determine whether they had further nausea and vomiting after leaving the emergency department, whether they required further care for the acute gastroenteritis, and details regarding the continuation, if any, of the illness. If symptoms persist for 3 or more days after study entry, the patient is to be instructed to return for further evaluation.

[d]To include all medications taken within 7 days prior to study entry, all treatments (including parenteral fluids) on the day of study entry, and all medication, including rescue medications, from the time of study entry through last follow-up.

[e]Patients are to receive the first dose of study medication within one hour of signing informed consent.

[f]Patients may take study medication daily for up to 3 days after study entry (maximum total of 4 doses, plus one additional if patient vomits within 15 minutes of first dose) if symptoms persist. Patients should stop taking study medication if symptoms have resolved, though they may resume study medication once daily if symptoms recur after discontinuation. Patients are not to take any remaining study medication after day 4. They will be given mailers to return any unused study medication.

Example 21—(Prophetic) Ways to Measure the Reduction of Prolonged Gastroenteritis Induced Vomiting after Administration of Solid Dosage Forms of the Present Invention To evaluate the reduction of gastroenteritis induced vomiting after administration of solid oral dosage forms of the present invention, vomiting symptoms, such as frequency, duration, volume, severity and distress will be measured. Frequency may be measured, for example, by the number of vomiting episodes in a specified period, duration may be measured, for example, by the number of hours of vomiting), volume may be measured, for example, in cups of vomit), severity may be measured, for example, by quantifying physical symptoms, and distress that the patient is experiencing may be measured, for example, by the resulting stress and psychological symptoms).

To evaluate the frequency and distress associated with vomiting, the Index of Nausea, Vomiting, and Retching (INVR) may be used. INVR has questions regarding the number of retching episodes in the previous 12 hours and the distress felt by these episodes.

Patients will be administered either a solid oral dosage form of the present invention (a 24 mg bimodal tablet as described above) or placebo, and the reduction in gastroenteritis induced vomiting will be assessed by looking at one or more vomiting symptoms, such as frequency, duration, volume, severity and distress.

Example 22—(Prophetic) Interventional Study to Assess the Severity of Vomiting after Administration of Solid Dosage Forms of the Present Invention to Women with Hyperemesis Gravidarum Desired Study Type: Interventional
Desired Study Design: Allocation: Randomized
Desired Endpoint Classification: Safety/Efficacy Study
Desired Intervention Model: Crossover Assignment
Desired Masking: Double Blind (Subject, Caregiver, Investigator, Outcomes Assessor)
Desired Primary Purpose: Treatment
Desired Primary Outcome Measures:
PUQE score for assessment of severity in Hyperemesis Gravidarum. PUQE in an acronym for Pregnancy Unique Quantification of Emesis, the only validated clinical score for assessment of severity of emesis. The range varies from 3 (best) to 15 (worst).
  Participants will be followed for the whole duration of hospital stay comparing the change from baseline in a first time period with a second time period
VAS score for assessment of severity in Hyperemesis Gravidarum
  VAS is a Visual Analogic Scale formulated of 5 items. The range swings from 0 (best) to 50 (worst).
  Participants will be followed for the whole duration of hospital comparing a first time period and a second time period
Desired Secondary Outcome Measures:
  Number of doses of standard antiemetic drugs (Zofran 8 mg tablet) required in the two different time periods.
  Pregnancy outcome measures: birth weight.
    Birth weight adjusted for gestational age at delivery is a measure of pregnancy outcome after treatment of HG.
  Pregnancy outcome measure: APGAR score.
    APGAR score is the most common indicator of neonatal status immediately after delivery.
Desired Other Outcome Measures:
  Morning urine ketonuria
    Morning urine ketonuria is a simple direct marker of starving associated to nausea and vomiting.
$1^{st}$ Arm: solid dosage form of the present invention first—placebo second
in this group patients will be treated with a solid ondansetron dosage form of the present invention for a first period of time then switch to placebo for a second period of time
$2^{nd}$ Arm: placebo first—solid dosage form of the present invention second
in this group patients will be treated with placebo for a first period of time then with a solid ondansetron dosage form of the present invention for a second period of time
Desired Criteria
Desired Inclusion Criteria:
  Gestational age 6-12 weeks and a major grade of HG clinical severity defined as follows:
  a PUQE score index ≥13 associated to one or more of the following conditions:
  weight loss >5% of pre-pregnancy weight,
  electrolyte disturbances,
  dehydration,
  duration of symptoms >10 days,
  inadequate food and drink intake Example 23—(Prophetic) Randomized, Placebo-Controlled Trial of Solid Dosage Forms of the Present Invention for Diarrhea Predominant Irritable Bowel Syndrome (IBS-D)

The Following Trial is Contemplated

Study drug 1 Ondansetron 24 mg bimodal tablets
Study drug 2 Ondansetron 12 mg bimodal tablets
Comparator Placebo
Rationale Irritable bowel syndrome (IBS) is a functional bowel disorder in which abdominal pain or discomfort is associated with disordered defecation. One of the major types of IBS is diarrhea predominant, IBS-D. 5-HT3 antagonists have been shown to slow intestinal transit time in animals and humans.
  The study drugs are bimodal release formulations of ondansetron. It provides an initial release similar to immediate release ondansetron and then extended release over 24 hours. Because of its extended release properties, it would appear to be an excellent candidate for treatment of IBS-D.
Objectives Proportion of patients with improvement in stool consistency
Primary/Secondary: Decrease in abdominal pain
  Transit time
  Decrease in abdominal discomfort
  Decrease in frequency of defecation
  Incidence and safety of adverse events
  Improvement in stool consistency
  Fewer days with urgency
Population Patients who meet Rome III criteria for IBS-D and do not have evidence of other gastrointestinal diseases which may be responsible for their symptomatology
Inclusion Criteria: 1. Male and female patients age ≥18 years
  2. Patient meets Rome III criteria for IBS-D:
    a. Recurrent abdominal pain or discomfort over ≥6 months, with frequency ≥3 days/month in the last 3 months associated with ≥2 of the following:
      i. Improvement with defecation
      ii. Onset associated with a change in frequency of stool
      iii. Onset associated with a change in the form of stool
    b. Loose or watery stools (Bristol stool form scale 6 or 7) ≥25% and hard or lumpy stools <25% of bowel movements
  3. Major laboratory parameters within the following limits (no worse than grade 1 abnormalities per NCI-CTCAE v4):
    a. Adequate hematologic function, as demonstrated by
      i. Hemoglobin 10 g/dL
      ii. ANC 1.5-10×10$^9$/L
      iii. Platelets 100×10$^9$/L
    b. Adequate liver and renal function as demonstrated by
      i. AST and ALT each ≤3.0×ULN
      ii. Total bilirubin 0.5×ULN
      iii. Creatinine 0.5×ULN
  4. C-reactive protein wnl for lab
  5. All patients must sign informed consent.
  6. Patients of childbearing potential and male partners of females of childbearing potential must utilize acceptable contraceptive measures
    a. Women of childbearing potential are women who have menstruated in the past 12 months, with the exception of women who have undergone surgical sterilization
  7. And optionally one or more negative stool cultures
Exclusion criteria: 1. Evidence of other cause for bowel disease:
    a. Colonoscopy with biopsy within 3 months of study entry
    b. Positive serologic test for celiac disease
    c. Lactose intolerance
  2. History of abdominal surgery other than appendectomy or cholecystectomy
  3. Use of SSRI, SNRT, or tricyclic antidepressant within 6 weeks of study entry
  4. Use of any 5-HT$_3$ antagonist within 4 weeks of study entry
  5. Uses of any investigational agent for any indication within 4 weeks of study entry
  6. Pregnant or lactating
  7. Patients with other major illnesses, either physical or psychiatric, which may interfere with participation in the study or interpretation of results
  8. And optionally IBS medication(s)
Design This is a 3-arm randomized, placebo-controlled study. After qualifying for the study, patients will undergo a one-week observation period during which stool and symptom data will be collected. Patients will then be randomized 1:1:1 to RHB-102 24 mg: RHB-102 12 mg: placebo to be taken once daily for 4 weeks
Methodology All patients will undergo baseline evaluation including full history and physical, with particular attention to gastrointestinal symptomatology and findings, a standard set of safety laboratory examinations (CBC and platelet count, biochemical profile, urinalysis), and 12-lead ECG. In addition, the following studies will be performed to exclude other causes of gastrointestinal symptoms:
  Serum testing for C-reactive protein and gluten sensitivity
  Colonoscopy if not performed within 3-6 months prior to study consent
  test for lactose intolerance if not performed within the past 6 months
  During the baseline observation phase, all patients will undergo assessment of stool transit time and keep diaries of symptomatology and stool frequency and consistency. Stool consistency will be assessed according to the Bristol Stool Form scale.
  Patients will keep diaries of stool frequency and consistency, symptoms, study medication compliance, and use of rescue medications throughout the study.
  Stool transit time will be measured every 2 weeks on study and 4 weeks after treatment is completed or otherwise discontinued.
  Safety laboratory examinations will be performed at the end of each treatment period and at the 4-week follow-up visit after discontinuation of treatment.
  Patients will be questioned periodically regarding concomitant medication use and the occurrence of adverse events.
Endpoints Efficacy: Stool consistency each stool, per Bristol Stool Form scale
  Worst abdominal pain intensity per 24-hour period, on an 11-point Likert scale
  Frequency of bowel movements
  Worst discomfort per 24-hour period, on an 11-point Likert scale
  Interference of IBS with general functioning, on a 5-point Likert scale
Pharmacodynamics: Stool transit time using Metcalf s radiopaque marker technique Safety Statistics: Occurrence of adverse events, both clinical and laboratory Study Populations Safety assessments will be based on results from all patients who receive any study medication, either active or placebo.

Pharmacodynamic results will be calculated using all patients who undergo baseline and at least one on-study measurement of transit time.

Efficacy data will be calculated, for intent to treatment, based on all patients randomized and who receive at least one dose of any study medication, either active or placebo. Per protocol analysis will include all patients who receive at least 75% of the planned study medication during at least the first treatment period and have baseline and at least one full week (at least 6 days of data) on study, or discontinue before that due to documented lack of efficacy.

Pharmacodynamics

Changes from baseline to measurements during each of the treatment periods, as well as on-treatment comparisons between each of the treatment groups will be calculated.

Efficacy

A responder is a patient who, during the second two weeks of the first treatment period or during the last two weeks of the second treatment period meets the following criteria (FDA Guidance re: IBS):
1. Stool consistency: ≥50% reduction in number of days per week as compared to baseline with ≥1 stool with Type 6 or 7 consistency, and Changes from baseline to the latter two weeks of each of treatment period will be calculated for each of these parameters, as well as for each of the secondary efficacy parameters.

Adverse events will be tabulated by system organ class (SOC) and preferred term (PT) using MedDRA version 13. Adverse events will be graded 1-4 according to NCI-CTCAE v4 criteria.

Example 24—(Prophetic) Randomized, Double-Blind, 3 Arm, Trial of Solid Dosage Forms of the Present Invention for Diarrhea Predominant Irritable Bowel Syndrome (IBS-D)

The Following Trial is Contemplated

| | |
|---|---|
| Study drug | Ondansetron 12 mg bimodal tablets |
| Comparator 1 | Ondansetron 4 mg tablets |
| Comparator 2 | Placebo |
| Rationale | Irritable bowel syndrome (IBS) is a functional bowel disorder in which abdominal pain or discomfort is associated with disordered defecation. One of the major types of IBS is diarrhea predominant, IBS-D. 5-HT3 antagonists have been shown to slow intestinal transit time in animals and humans<br>The Study drug is a bimodal release formulation of ondansetron. It provides an initial release similar to immediate release ondansetron as well as extended release over 24 hours. Because of its extended release properties, it would appear to be an excellent candidate for treatment of IBS-D. |
| Objectives Primary: | Proportion of patients with improvement in stool consistency during weeks 3 and 4 as compared to baseline:<br>A stool consistency responder is defined as a patient who experiences a 50 percent or greater reduction in the number of days per week with at least one stool that has a consistency of Bristol stool form type 6 or 7 compared with baseline, and abdominal pain is unchanged or improved in comparison with baseline |
| Secondary: | Decrease in abdominal pain<br>Decrease in abdominal discomfort<br>Decrease in frequency of defecation<br>Incidence and severity of adverse events |
| Population | Patients who meet Rome III criteria for IBS-D and do not have evidence of other gastrointestinal diseases which may be responsible for their symptomatology |
| Key Inclusion criteria: | 7. Male and female patients age≥18 years (with a minimum of 33% males in the study)<br>8. Patient meets Rome III criteria for IBS-D:<br>   a. Recurrent abdominal pain or discomfort over ≥6 months, with frequency ≥3 days/month in the last 3 months associated with ≥2 of the following:<br>      i. Improvement with defecation<br>      ii. Onset associated with a change in frequency of stool<br>      iii. Onset associated with a change in the form of stool<br>   b. Loose or watery stools (Bristol stool form scale 6 or 7) ≥25% and hard or lumpy stools <25% of bowel movements<br>9. Major laboratory parameters within the following limits (no worse than grade 1 abnormalities per NCI-CTCAE v4):<br>   a. Adequate hematologic function, as demonstrated by<br>      i. Hemoglobin ≥10 g/dL<br>      ii. ANC ≥1.5-10 × $10^9$/L<br>      iii. Platelets ≥100 × $10^9$/L<br>   b. Adequate liver and renal function as demonstrated by<br>      i. AST and ALT each ≤3.0 × ULN<br>      ii. Total bilirubin ≤1.5 × ULN<br>      iii. Creatinine ≤1.5 × ULN |

| | |
|---|---|
| | 10. C-reactive protein wnl for lab<br>11. All patients must sign informed consent.<br>12. Patients of childbearing potential and male partners of females of childbearing potential must utilize acceptable contraceptive measures<br>    a. Women of childbearing potential are women who have menstruated in the past 12 months, with the exception of women who have undergone surgical sterilization |
| Key Exclusion criteria: | 9. Evidence of other cause for bowel disease:<br>    a. Colonoscopy with biopsy within [6] months of start of screening<br>    b. Positive serologic test for celiac disease<br>    c. Lactose intolerance objectively documented by lactose breath hydrogen test<br>10. History of abdominal surgery other than appendectomy or cholecystectomy<br>11. Use of SSRI, SNRI, or tricyclic antidepressant within 6 weeks of study entry<br>12. Use of any 5-$HT_3$ antagonist within 4 weeks of study entry<br>13. Uses of any investigational agent for any indication within 4 weeks of study entry<br>14. Pregnant or lactating<br>15. Patients with other major illnesses, either physical or psychiatric, which may interfere with participation in the study or interpretation of results |
| Design | This is a randomized double-blind, 3 arm parallel group study. After qualifying for the study, patients will undergo a two-week observation period during which stool consistency and frequency data and symptom data will be collected. Patients will then be randomized 1:1:1 Study drug, Comparator 1 or Comparator 2. Patients will continue on treatment for 4 weeks. Each medication will be given once daily.<br>Group    Treatment<br>A    Study drug<br>B    Comparator 1<br>C    Comparator 2 |
| Methodology | All patients will undergo baseline evaluation including full history and physical, with particular attention to gastrointestinal symptomatology and findings, a standard set of safety laboratory examinations (CBC and platelet count, biochemical profile, urinalysis), and 12-lead ECG. In addition, the following studies will be performed to exclude other causes of gastrointestinal symptoms:<br>    Serum testing for C-reactive protein and gluten sensitivity<br>    Colonoscopy if not performed within [6] months prior to study consent<br>    Lactose hydrogen breath test if not performed within the past 6 months<br>    Starting during the baseline observation phase, all patients will keep diaries of symptomatology and stool frequency and consistency. Stool consistency will be assessed according to the Bristol Stool Form scale.<br>Patients will keep diaries of stool frequency and consistency, symptoms, study medication compliance, and use of rescue medications throughout the study.<br>Safety laboratory examinations will be performed at the end of the 4 week treatment period and at a follow-up visit 2 weeks after discontinuation of treatment.<br>Patients will be questioned periodically regarding concomitant medication use and the occurrence of adverse events. |
| Endpoints<br>Efficacy: | Stool consistency each stool, per Bristol Stool Form scale<br>Worst abdominal pain intensity per 24-hour period, on an 11-point Likert scale<br>Frequency of bowel movements<br>Worst discomfort per 24-hour period, on an 11-point Likert scale<br>Interference of IBS with general functioning, on a 5-point Likert scale |
| Safety: | Occurrence of adverse events, both clinical and laboratory |
| Statistics<br>Sample size<br>calculation | The following parameter represent the expected therapeutic effect of each treatment arm:<br>Group A (Study drug) - 80% responders<br>Group B (Comparator 1) - 65% responders<br>Group C (Comparator 2) - 40% responders |
| Study<br>populations: | Sample size will be calculated based on expected change in primary endpoint between groups A and C using 90% power, $p \leq 0.05$.<br>Group B will be evaluated for dose response trends but is not used to power the study for statistical significance. |

-continued

| | |
|---|---|
| Efficacy: Primary endpoint | Safety assessments will be based on results from all patients who receive any study medication, either active or placebo. Efficacy data will be calculated, for intent to treatment, based on all patients randomized and who receive at least one dose of any study medication, either active or placebo. Per protocol analysis will include all patients who receive at least 75% of the planned study medication and have baseline and at least one full week (at least 6 days of data) on study, or discontinue before that due to documented lack of efficacy. A stool consistency responder (FDA Guidance re: IBS) is defined as a patient who experiences during treatment weeks 3 and 4 a 50 percent or greater reduction in the number of days with at least one stool that has a consistency of Type 6 or 7 compared with baseline, and abdominal pain is unchanged or improved in comparison with baseline. A responder is a patient who, during the second two weeks of the treatment period meets the following criteria (FDA Guidance re: IBS): Abdominal pain intensity weekly responder: patient who experiences a decrease in the weekly average of worst abdominal pain in the past 24 hours score of at least 30 percent compared with baseline during weeks 3 and 4. AND Stool consistency responder, as defined above. Changes from baseline to the latter two weeks of each for these parameters, as well as for each of the secondary efficacy parameters. Adverse events will be tabulated by system organ class (SOC) and preferred term (PT) using MedDRA version 13. Adverse events will be graded 1-4 according to NCI-CTCAE v4 criteria. |

Ondansetron extended release solid oral dosage form for treating either nausea, vomiting, or diarrhea symptoms are disclosed herein.

According to aspects illustrated herein, a method of treating a patient comprises orally administering, to a patient, a solid oral dosage form comprising a core comprising a non-ionic polymer matrix, a first amount of ondansetron dispersed within the matrix, and a salt dispersed within the matrix, wherein the first amount of ondansetron ranges from about 9 mg to about 28 mg; a first seal coat surrounding the core, wherein the first seal coat is comprised of a non-ionic polymer matrix; and an immediate release drug layer surrounding the first seal coat and comprising a non-ionic polymer and a second amount of ondansetron dispersed therein, wherein the second amount of ondansetron ranges from about 3 mg to about 8 mg, wherein release of ondansetron from the solid oral dosage form provides exposure to ondansetron for a minimum period of 16 hours so as to result in a reduction in frequency of vomiting, nausea, diarrhea, or a combination thereof.

Extended release solid dosage forms are disclosed herein for reducing, treating, or preventing either nausea, vomiting or diarrhea in a subject, symptoms that can be caused by a variety of conditions. In an embodiment, nausea, vomiting or diarrhea are side effects of viral gastroenteritis in a subject. In an embodiment, nausea, vomiting or diarrhea are side effects of bacterial gastroenteritis in a subject. In an embodiment, nausea, vomiting or diarrhea are side effects of gastritis (inflammation of the gastric wall) in a subject. In an embodiment, nausea, vomiting or diarrhea are side effects of inflammatory bowel disease in a subject. In an embodiment, nausea, vomiting or diarrhea are side effects of irritable bowel syndrome in a subject. In an embodiment, nausea, vomiting or diarrhea are side effects of cholecystitis in a subject. In an embodiment, nausea, vomiting or diarrhea are side effects of dyspepsia in a subject. In an embodiment, nausea, vomiting or diarrhea are side effects of pancreatitis in a subject. In an embodiment, nausea, vomiting or diarrhea are side effects of appendicitis in a subject. In an embodiment, nausea, vomiting or diarrhea are side effects of a surgical procedure in a subject. In an embodiment, nausea, vomiting or diarrhea are side effects of hepatitis in a subject. In an embodiment, nausea, vomiting or diarrhea are side effects of peritonitis in a subject. In an embodiment, nausea, vomiting or diarrhea are side effects of gastroesophageal reflux disease in a subject. In an embodiment, nausea, vomiting or diarrhea are side effects of bowel obstructive in a subject. In an embodiment, nausea, vomiting or diarrhea are side effects of food poisoning in a subject. In an embodiment, nausea, vomiting or diarrhea are side effects of a tumor in a subject.

According to aspects illustrated herein, there is disclosed a solid oral dosage form that includes a core comprising a non-ionic polymer matrix, a first amount of a first antiemetic drug or a pharmaceutically acceptable salt thereof dispersed within the matrix, and a salt dispersed within the matrix; a first seal coat surrounding the core, wherein the first seal coat is comprised of a non-ionic polymer matrix; and an immediate release drug layer surrounding the first seal coat, wherein the immediate release drug layer comprises a non-ionic polymer and a second amount of a second antiemetic drug or a pharmaceutically acceptable salt thereof dispersed therein, wherein the drug layer is sufficiently designed to release the second amount of the antiemetic drug over a period of at least 1 hour, wherein the solid oral dosage form is sufficiently designed to release the first amount of the first antiemetic drug and the second amount of the second antiemetic drug over a minimum period of 16 hours. In an embodiment, the solid oral dosage form further includes an enteric coating surrounding the first seal coat. In an embodiment, the solid oral dosage form further includes a second seal coat surrounding the immediate release drug layer, wherein the second seal coat is comprised of a non-ionic polymer. In an embodiment, the first seal coat further comprises a coating additive such as plasACRYL™ In an embodiment, the salt in the core is dispersed in the matrix at a concentration in the range of 50% to 100% by weight of the matrix. In an embodiment, upon exposure of the solid dosage form to an aqueous medium, the salt causes a hardened boundary around the periphery of the matrix, the boundary sequentially progressing inwardly toward the center thereof as the aqueous medium permeates the matrix, the hardened boundary limiting the rate at which the antiemetic drug in the matrix is released from the tablet. In an embodiment, the solid oral dosage form is sufficiently designed to release the first amount of the antiemetic drug and the second amount of the antiemetic drug over a minimum period of 20 hours. In an embodiment, the solid oral dosage form is sufficiently designed to release the first amount of the antiemetic drug and the second amount of the antiemetic drug over a minimum period of 24 hours. In an embodiment, the first antiemetic drug and the second antiemetic drug are the same drug. In an embodiment, the first antiemetic drug and the second antiemetic drug are each ondansetron or an equivalent amount of an ondansetron salt thereof.

According to aspects illustrated herein, there is disclosed a solid oral dosage form that includes a core comprising hypromellose, 18 mg of ondansetron or an equivalent amount of an ondansetron salt thereof, and sodium citrate anhydrous; a first seal coat surrounding the core and comprising hypromellose; and an immediate release drug layer surrounding the first seal coat and comprising hypromellose and 6 mg of ondansetron or an equivalent amount of an ondansetron salt thereof, the immediate release drug layer sufficient to release the ondansetron over a period of at least 1 hour, wherein the total amount of ondansetron in the dosage form is released over 24 hours. In an embodiment, the solid oral dosage form further includes an enteric coating surrounding the first seal coat. In an embodiment, the solid oral dosage form further includes a second seal coat surrounding the immediate release drug layer, wherein the second seal coat is comprised of a non-ionic polymer. In an embodiment, the first seal coat further comprises a coating additive such as plasACRYL™. In an embodiment, the sodium citrate anhydrous in the core is dispersed in the hypromellose at a concentration in the range of 50% to 100% by weight of the hypromellose. In an embodiment, upon exposure of the solid oral dosage form to an aqueous medium, the sodium citrate anhydrous causes a hardened boundary around the periphery of the hypromellose, the boundary sequentially progressing inwardly toward the center thereof as the aqueous medium permeates the hypromellose, the hardened boundary limiting the rate at which the ondansetron in the hypromellose is released from the tablet. In an embodiment, when the solid oral dosage form is administered to a patient in a fasting state, achieves a $C_{max}$ of at least 50 ng/ml. In an embodiment, when the solid oral dosage form is administered to a patient in a fasting state, achieves AUC of at least 700 nghr/ml.

According to aspects illustrated herein, there is disclosed a solid oral dosage form that includes a core comprising a non-ionic polymer matrix, a first amount of ondansetron or an equivalent amount of an ondansetron salt thereof dispersed within the matrix, and a salt dispersed within the matrix; a first seal coat surrounding the core, wherein the first seal coat is comprised of a non-ionic polymer matrix; and an immediate release drug layer surrounding the first seal coat, wherein the immediate release drug layer comprises a non-ionic polymer and a second amount of ondansetron or an equivalent amount of an ondansetron salt thereof dispersed therein, wherein the solid oral dosage form results in an in vitro ondansetron dissolution profile when measured in a type 2 paddle dissolution apparatus at 37° C. in aqueous solution containing distilled water at 50 rpm that exhibits: a) from about 15% to 30% of the total ondansetron is released after two and a half hours of measurement in the apparatus; b) from about 30% to 50% of the total ondansetron is released after five hours of measurement in the apparatus; and c) no less than about 75% of the total ondansetron is released after fifteen hours of measurement in the apparatus. 26. In an embodiment, when the solid oral dosage form is administered to a patient in a fasting state at a dose of 24 mg ondansetron, achieves a $C_{max}$ of at least 50 ng/ml. In an embodiment, when the solid oral dosage form is administered to a patient in a fasting state at to dose of 24 mg ondansetron, achieves AUC of at least 700 nghr/ml.

According to aspects illustrated herein, there is disclosed a packaged pharmaceutical preparation that includes a plurality of any of the solid oral dosage forms of the present invention in a sealed container and instructions for administering the dosage forms orally to effect prevention of nausea.

According to aspects illustrated herein, there is disclosed a packaged pharmaceutical preparation that includes a plurality of any of the solid oral dosage forms of the present invention in a sealed container and instructions for administering the dosage forms orally to effect prevention of vomiting.

According to aspects illustrated herein, there is disclosed a packaged pharmaceutical preparation that includes a plurality of any of the solid oral dosage forms of the present invention in a sealed container and instructions for administering the dosage forms orally to effect prevention of diarrhea.

According to aspects illustrated herein, there is disclosed a pharmaceutical preparation that includes a plurality of any of the solid oral dosage forms of the present invention each in a discrete sealed housing, and instructions for administering the dosage forms orally to effect prevention of nausea.

According to aspects illustrated herein, there is disclosed a pharmaceutical preparation that includes a plurality of any of the solid oral dosage forms of the present invention each in a discrete sealed housing, and instructions for administering the dosage forms orally to effect prevention of vomiting.

According to aspects illustrated herein, there is disclosed a pharmaceutical preparation that includes a plurality of any of the solid oral dosage forms of the present invention each in a discrete sealed housing, and instructions for administering the dosage forms orally to effect prevention of diarrhea.

According to aspects illustrated herein, there is disclosed a unit dosage form for preventing nausea and/or vomiting for oral administration to a patient that includes a combination of: an immediate release ondansetron component containing a unit dosage of ondansetron or a pharmaceutically acceptable salt thereof in the range of 4 mg to 8 mg; and a controlled release ondansetron component containing a unit dosage of ondansetron or a pharmaceutically acceptable salt thereof in the range of 16 mg to 28 mg, the controlled release ondansetron component comprising a non-ionic polymer matrix, the ondansetron within the matrix, and a salt dispersed within the matrix, and wherein the unit dosage form exhibits a maximum plasma concentration (Cmax) at about 2 to about 5 hours (Tmax) after administration and exhibits a comparable Cmax to a non-controlled release ondansetron formulation administered three times per day without decreasing total drug exposure defined by the area under the concentration-time curve (AUC), thereby enabling reduction of concentration-dependent side effects without a decrease in efficacy.

According to aspects illustrated herein, there is disclosed a unit dosage form for preventing diarrhea for oral administration to a patient that includes a combination of: an immediate release ondansetron component containing a unit dosage of ondansetron or a pharmaceutically acceptable salt thereof in the range of 4 mg to 8 mg; and a controlled release ondansetron component containing a unit dosage of ondansetron or a pharmaceutically acceptable salt thereof in the range of 16 mg to 28 mg, the controlled release ondansetron component comprising a non-ionic polymer matrix, the ondansetron within the matrix, and a salt dispersed within the matrix, and wherein the unit dosage form exhibits a maximum plasma concentration ($C_{max}$) at about 2 to about 5 hours (Tmax) after administration and exhibits a comparable $C_{max}$ to a non-controlled release ondansetron formulation administered three times per day without decreasing total drug exposure defined by the area under the concentration-time curve (AUC), thereby enabling reduction of concentration-dependent side effects without a decrease in efficacy.

A packaged pharmaceutical preparation that includes a plurality of the unit dosage forms of the present invention can be contained within a sealed container and include instructions for administering the dosage forms orally to effect prevention of nausea.

A packaged pharmaceutical preparation that includes a plurality of the unit dosage forms of the present invention can be contained within a sealed container and include instructions for administering the dosage forms orally to effect prevention of vomiting.

A packaged pharmaceutical preparation that includes a plurality of the unit dosage forms of the present invention can be contained within a sealed container and include instructions for administering the dosage forms orally to effect prevention of diarrhea.

A packaged pharmaceutical preparation that includes a plurality of the unit dosage forms of the present invention can be contained within a discrete sealed housing and include instructions for administering the dosage forms orally to effect prevention of nausea.

A packaged pharmaceutical preparation that includes a plurality of the unit dosage forms of the present invention can be contained within a discrete sealed housing and include instructions for administering the dosage forms orally to effect prevention of vomiting.

A packaged pharmaceutical preparation that includes a plurality of the unit dosage forms of the present invention can be contained within a discrete sealed housing and include instructions for administering the dosage forms orally to effect prevention of diarrhea.

A method for preventing nausea includes the step of administering a therapeutically-effective amount of a solid oral dosage form or a unit dosage form of the present invention to a patient.

A method for preventing vomiting includes the step of administering a therapeutically-effective amount of a solid oral dosage form or a unit dosage form of the present invention to a patient.

A method for preventing diarrhea includes the step of administering a therapeutically-effective amount of a solid oral dosage form or a unit dosage form of the present invention to a patient.

According to aspects illustrated herein, there is disclosed a once-a-day composition that includes: (a) a core comprising a non-ionic polymer matrix, a first amount of ondansetron or an equivalent amount of an ondansetron salt dispersed within the matrix, and a salt dispersed within the matrix; (b) a first seal coat surrounding the core, wherein the first seal coat is comprised of a non-ionic polymer matrix; and (c) an immediate release drug layer surrounding the enteric coating, wherein the immediate release drug layer comprises a non-ionic polymer and a second amount of ondansetron or an equivalent amount of an ondansetron salt dispersed therein, wherein the immediate release drug layer is sufficiently designed to release the second amount of ondansetron over a period of at least 1 hour, wherein the immediate release drug layer releases the second amount of ondansetron in the upper gastrointestinal tract of a human patient, wherein the core releases the first amount of ondansetron in the lower gastrointestinal tract of a human patient, wherein the composition is a tablet or capsule that contains 24 to 40 mg of ondansetron or an equivalent amount of an ondansetron salt, and provides an in vivo plasma profile selected from: (a) a mean $C_{max}$ of at least 50.0 ng/ml; (b) a mean $AUC_{0-24}$ of greater than 550.0 nghr/ml; and (c) a mean $T_{max}$ of between approximately 2.0 hours and 5.0 hours based upon a single dose administration of a composition containing 24 mg of ondansetron. In an embodiment, the once-a-day composition, when administered once-a-day to a human in a fasted state, is bioequivalent to administration to a human in a fasted state, three-times-a-day, a unit dosage form comprising 8 mg ondansetron. In an embodiment, the bioequivalency is established by a 90% Confidence Interval of between 0.80 and 1.25 for both $C_{max}$ and AUC, when administered to a human. In an embodiment, solubility and dissolution characteristics are pH-independent. In an embodiment, the core has a pH-independent dissolution release profile over a pH range of 1.2-6.8. In an embodiment, each of the core and the immediate release drug layer have a pH-independent dissolution release profile over a pH range of 1.2-6.8. In an embodiment, each of the core and the immediate release drug layer are surrounded by a seal coat comprised of a non-ionic polymer which increases hydrophilicity of the composition and as a result the dissolution profile of the composition is pH-independent.

All patents, patent applications, and published references cited herein are hereby incorporated by reference in their entirety. It will be appreciated that several of the above-disclosed and other features and functions, or alternatives thereof, may be desirably combined into many other different systems or application. Various presently unforeseen or unanticipated alternatives, modifications, variations, or improvements therein may be subsequently made by those skilled in the art.

What is claimed is:

1. A kit comprising:
    at least a four week supply of bimodal release ondansetron tablets suitable to treat diarrhea predominant irritable bowel syndrome (IBS-D), wherein each tablet provides drug release over 24 hours and comprises:
        a drug core, the drug core comprising a hydrophilic swellable polymer matrix in which is dispersed sodium citrate anhydrous and ondansetron or an ondansetron salt thereof, wherein the sodium citrate anhydrous has properties that allow it to form a hardened boundary around the periphery of the polymer matrix upon exposure to an aqueous medium so as to limit the rate at which the ondansetron is released from the core;
        a non-functional seal coat surrounding the core and comprising hypromellose, wherein the non-functional seal coat has the property to not substantially affect the release of the ondansetron from the tablet; and an immediate release drug layer surrounding the seal coat, the immediate release drug layer comprising hypromellose and ondansetron or an ondansetron salt thereof, wherein the immediate release drug layer provides an immediate burst release of ondansetron after oral administration, and wherein the drug core provides a zero-order sustained release of ondansetron immediately after completion of the burst release of ondansetron from the immediate release drug layer, wherein there is no lag in release of ondansetron from the tablet; and a label indicating to take one tablet orally from the supply each day so as to result in an improvement in stool consistency.

2. The kit of claim 1, wherein the tablet when administered to a subject in need thereof decreases abdominal pain.

3. The kit of claim 1, wherein the tablet when administered to a subject in need thereof decreases abdominal discomfort.

4. The kit of claim 1, wherein the tablet when administered to a subject in need thereof decreases frequency of defecation.

5. The kit of claim 1, wherein the drug core comprises 9 mg ondansetron or an equivalent amount of an ondansetron salt thereof, and wherein the immediate release drug layer comprises 3 mg ondansetron or an equivalent amount of an ondansetron salt thereof.

* * * * *